(12) United States Patent  (10) Patent No.: US 8,460,608 B2
Strano et al.  (45) Date of Patent: Jun. 11, 2013

(54) SYSTEMS AND METHODS RELATED TO OPTICAL NANOSENSORS COMPRISING PHOTOLUMINESCENT NANOSTRUCTURES

(75) Inventors: Michael S. Strano, Lexington, MA (US); Daniel A. Heller, Rye Brook, NY (US); George W. Pratt, Melrose, MA (US); Jingqing Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 22 days.

(21) Appl. No.: 12/967,563

(22) Filed: Dec. 14, 2010

(65) Prior Publication Data

US 2011/0269243 A1   Nov. 3, 2011

Related U.S. Application Data

(60) Provisional application No. 61/309,840, filed on Mar. 2, 2010, provisional application No. 61/286,324, filed on Dec. 14, 2009.

(51) Int. Cl.
*G01N 21/64* (2006.01)
(52) U.S. Cl.
USPC .................. 422/82.07; 422/82.08; 422/82.11; 422/400; 422/405

(58) Field of Classification Search
None
See application file for complete search history.

(56) References Cited

FOREIGN PATENT DOCUMENTS

WO   WO2011/022677   2/2011

OTHER PUBLICATIONS

Arnold, et al., "Encapsulation of carbon nanotubes by self-assembling peptide amphiphiles," Langmuir, 20050510, American Chemical Society US, vol. 21, No. 10, May 10, 2005, pp. 4705-4709.
Liu, et al., "Modifications of carbon nanotubes with polymers," European Polymer Journal, Pergamon Press, Ltd., Oxford, GB, vol. 41, No. 11, Nov. 1, 2005, pp. 2693-2703.
Medintz, et al., "Designer variable repeat length polypeptides as scaffolds for surface immobilization of quantum dots," Journal of Physical Chemistry, American Chemical Society US, vol. 110, No. 22, Jun. 8, 2006, pp. 10683-10690.
Barone, et al., "In vivo fluorescence detection of glucose using a single-walled carbon nanotube optical sensor: design, fluorophore properties, advantages, and disadvantages," Analytical Chemistry, American Chemical Society US, vol. 77, No. 23, Dec. 1, 2005, pp. 7556-7562.
International Search Report and Written Opinion, PCT/US2010/060092, mailed on May 23, 2011.
International Preliminary Report on Patentability dated Jun. 28, 2012 for PCT/US2010/060092.

*Primary Examiner* — Robert Xu
(74) *Attorney, Agent, or Firm* — Steptoe & Johnson LLP

(57) ABSTRACT

Systems and methods related to optical nanosensors comprising photoluminescent nanostructures are generally described.

16 Claims, 41 Drawing Sheets

SYSTEMS AND METHODS RELATED TO OPTICAL NANOSENSORS COMPRISING PHOTOLUMINESCENT NANOSTRUCTURES

CLAIM OF PRIORITY

This application claims priority to provisional U.S. Patent Application No. 61/309,840, filed Mar. 2, 2010, and to provisional U.S. Patent Application No. 61/286,324, filed Dec. 14, 2009, each of which is incorporated by reference in its entirety.

This application also references PCT application no. PCT/US2010/60092, filed Dec. 13, 2010, which is incorporated by reference in its entirety.

GOVERNMENT SPONSORSHIP

This invention was made with government support under Grant No. CBET 0753036 awarded by the National Science Foundation. The government has certain rights in this invention.

TECHNICAL FIELD

Systems and methods related to optical nanosensors comprising photoluminescent nanostructures are generally described.

BACKGROUND

The detection of compounds containing cyclic rings and nitrogen atoms can be desirable for a variety of applications. For example, nitroaryl-containing compounds are used in many relatively dangerous products such as, for example, pesticides, explosives, and the like. The detection of nitroaryl-containing compounds can be useful, for example, in locating land mines, searching for explosive materials at security checkpoints, analyzing pesticide levels at clean-up sites, and the like. Determination of such compounds can pose several challenges. For example, it can be difficult, in some instances, to determine the quantity and/or identity of such compounds while maintaining the safety of the person making the measurement. In addition, real-time determination can be difficult, with chemical analyses often requiring complicated, time-consuming, and expensive laboratory procedures.

SUMMARY

Systems and methods related to optical nanosensors comprising photoluminescent nanostructures are generally described. The subject matter described herein involves, in some cases, interrelated products, alternative solutions to a particular problem, and/or a plurality of different uses of one or more systems and/or articles.

In one aspect, a nanosensor for determining an analyte includes a photoluminescent nanostructure, and a polymer associated with the photoluminescent nanostructure, where the nanosensor emits a first emission of electromagnetic radiation in the absence of the analyte, and the nanosensor emits a second emission of electromagnetic radiation, distinguishable from the first emission, upon interacting with the analyte.

In another aspect, a method of determining an analyte includes exposing a first nanosensor including a first photoluminescent carbon-based nanostructure and a first polymer interacting with the first photoluminescent carbon-based nanostructure to a first analyte, where the first analyte interacts with the first nanosensor to produce a first emission of electromagnetic radiation, and determining the first analyte based at least in part upon the first emission of electromagnetic radiation.

The polymer can include a polypeptide. The polypeptide can be selected from the group consisting of: an amphiphilic helical polypeptide; a polypeptide including between about 5 and about 50 amino acid residues; and a polypeptide with a molecular weight of between about 400 g/mol and about 10,000 g/mol. In some cases, the polymer can include a polypeptide including between about 5 and about 30 amino acid residues, or can include a polypeptide with a molecular weight of between about 400 g/mol and about 6,000 g/mol.

The polymer can include a polypeptide sequence, or derivative thereof, observed in the venom of a member of the Insecta class; a member of the Hymenoptera order; or a member of the Vespidae or Apidae families. The polymer can include a polypeptide, or derivative thereof, from the Mastoparan or Bombolitin peptide families. The polymer can include a polypeptide comprising at least one of KKAAAV-LLPVLLAAP (SEQ ID NO: 1), EEEECCCCHSSYW-YAFNNKT (SEQ ID NO: 2), INLKALAALAKKIL (SEQ ID NO: 3), INLKALAALAKALL (SEQ ID NO: 4), INWK-GIAAMAKKLL (SEQ ID NO: 5), IKIMDILAKLGKV-LAHV (SEQ ID NO: 6), INIKDILAKLVKVLGHV (SEQ ID NO: 7), IKITTMLAKLGKVLAHV (SEQ ID NO: 8), or SKITDILAKLGKVLAHV (SEQ ID NO: 9).

The polymer can include polyvinylpyrrolidone, polyvinyl alcohol, collagen, or phenylated dextran.

The polymer can include an oligonucleotide. The polymer can include a single-stranded DNA oligonucleotide. The single-stranded DNA oligonucleotide can include at least 5 repeating units, in succession, of at least one of (GT), (AT), (AAAAT), or (GGGGT). The single-stranded DNA oligonucleotide can include at least 10 repeating units, or at least 15 repeating units, in succession, of at least one of (GT) or (AT).

The nanosensor can emit a third emission of electromagnetic radiation, distinguishable from the first emission and the second emission, upon interacting with a second analyte.

The photoluminescent nanostructure can include a carbon nanotube; a single-walled carbon nanotube; or a semiconducting single-walled carbon nanotube.

The analyte can include at least one $NO_2$ group, and/or can include a cyclic compound; for example, the analyte can include a nitroaryl group. The analyte can include at least one of a pesticide or an explosive. For example, the analyte can include at least one of 2,4-dinitrophenol, 4-nitro-3-(trifluoromethyl)phenol, picric acid, trinitrotoluene, or cyclotrimethylenetrinitramine.

The method of determining an analyte can further include exposing the first nanosensor to a second analyte, wherein the second analyte interacts with the first nanosensor to produce a second emission of electromagnetic radiation, distinguishable from the first emission. The first emission can have a first average intensity, and the second emission can have a second average intensity, where the first and second average intensities are different. The first emission can have at least one peak wavelength, and the second emission can have a second peak wavelength, where the first and second peak wavelengths are different. The first emission can occur at a first wavelength with a first intensity, and the second emission can occur at the first wavelength at a second intensity that is different from the first intensity.

The method can further include exposing a second nanosensor include a second photoluminescent carbon-based nanostructure and a second polymer interacting with the second photoluminescent carbon-based nanostructure to the first analyte, where the first analyte interacts with the second nanosensor to produce a second emission of electromagnetic radiation, distinguishable from the first emission.

The method can still further include exposing the first nanosensor and the second nanosensor to a second analyte, where the second analyte interacts with the first nanosensor to produce a third emission of electromagnetic radiation, and the second analyte interacts with the second nanosensor to produce a fourth emission of electromagnetic radiation, distinguishable from the third emission, and determining the second analyte based at least in part upon the third or fourth emissions of electromagnetic radiation.

The method can include filtering at least one of the first, second, third, and/or fourth emissions of electromagnetic radiation such that wavelengths within a specified range are transmitted. At least one of the first emission, the second emission, the third emission, and the fourth emission of electromagnetic radiation can include near-infrared electromagnetic radiation. The overall intensity of the second emission of electromagnetic radiation can be different than the overall intensity of the first emission of electromagnetic radiation.

In the method, the first nanosensor, the second nanosensor, or both, can be simultaneously exposed to the first and second analytes. Determining the first analyte, determining the second analyte, or both, can include using principal component analysis. Determining an analyte can include determining the identity and/or concentration of the analyte.

When two or more photoluminescent nanostructures are present, the first photoluminescent nanostructure and the second photoluminescent nanostructure can have different chiralities, different diameters, and/or different optical bandgaps. In particular, two or more different carbon nanotubes, single-walled carbon nanotubes, or semiconducting single-walled carbon nanotubes, can have different chiralities, different diameters, and/or different optical bandgaps.

Other advantages and novel features will become apparent from the following detailed description of various non-limiting embodiments when considered in conjunction with the accompanying figures.

BRIEF DESCRIPTION OF THE DRAWINGS

FIGS. 20A-20B are time traces of single molecule detection in two different wavelength channels. FIGS. 20C-20D are histograms depicting correlated and anticorrelated steps in the time traces, respectively.

DETAILED DESCRIPTION

Figure 1A:
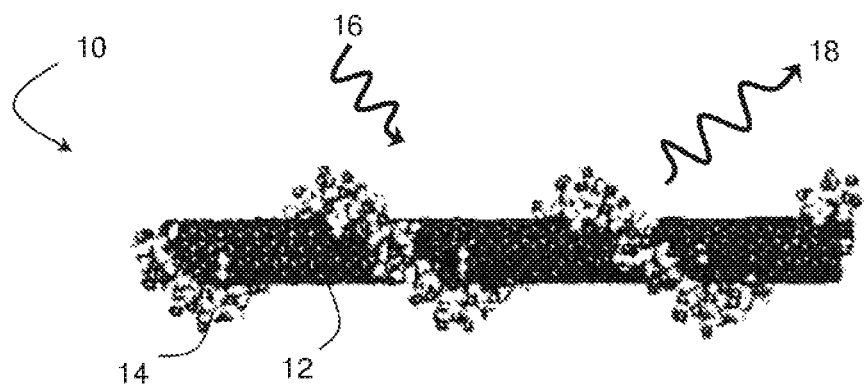
FIGS. 1A-1C include schematic illustrations of nanosensors, according to one set of embodiments.

Systems and methods related to optical nanosensors comprising photoluminescent nanostructures are generally described. Generally, the nanosensors comprise a photoluminescent nanostructure and a polymer that interacts with the photoluminescent nanostructure. In some cases, the interaction between the polymer and the nanostructure can be non-covalent (e.g., via van der Waals interactions). A nanosensor may emit a first emission of electromagnetic radiation in the presence of a first analyte. In some cases, the presence of a second analyte may cause the nanosensor to emit a second emission of electromagnetic radiation that is different from the first emission. In some embodiments, the first and/or second emissions can be different than an emission of electromagnetic radiation that is observed from the nanosensor in the absence of the first and/or second analyte. An analyte may comprise, in some embodiments, a compound comprising a cyclic ring and at least one nitrogen atom. For example, in some cases, the compound can be a nitroaryl-containing compound (e.g., explosives, pesticides, and the like).

The nanosensors described herein may exhibit one or more advantageous properties relative to traditional sensors. The nanosensors can determine an analyte via a direct interaction between the analyte and a component of the nanosensor (e.g., the photoluminescent nanostructure), rather than via an interaction between a by-product of a reaction involving an analyte and a component of the nanosensor. The ability to determine an analyte based upon such a direct interaction can be useful in reducing or effectively eliminating unwanted interference between the analyte of interest and a background species. The nanosensors described herein can also exhibit relatively low amounts of undesired photobleaching, which can reduce or effectively eliminate distortions in the signal produced by the photoluminescent nanosensor. The nanosensors can also exhibit little or no overlapping with auto-fluorescence from, for example, endogenous fluorophores. Moreover, the nanosensors described herein can emit and/or respond to wavelengths capable of penetrating human tissue (e.g., near-infrared radiation), making the nanosensors particularly suitable, for example, for in vivo testing in humans. In addition, as mentioned, the nanosensors described herein can be capable of determining analytes at very low concentrations.

In some embodiments, the nanosensors described herein can be used to determine analytes comprising one or more $NO_2$ groups. In some embodiments, the nanosensors described herein can be used to determine analytes comprising one or more cyclic rings and at least one nitrogen atom (e.g., an $NO_2$ group). In some embodiments, the nanosensors described herein can be used to determine analytes comprising one or more nitroaryl groups. As used herein, the term "nitroaryl" is given its ordinary meaning in the art, and generally refers to a group comprising an aromatic ring and at least one $NO_2$ group. Exemplary aromatic rings include, but are not limited to, phenyl, thiophene, indolyl, tolyl, xylyl, and the like. A "nitroaryl-containing compound" or a "nitroaryl-containing analyte" is a compound or analyte that includes at least one nitroaryl group. In some cases, the nanosensors described herein can be used to determine an explosive or a pesticide. Exemplary analytes that can be determined include, but are not limited to, 2,4-dinitrophenol, 4-nitro-3-(trifluoromethyl)phenol, picric acid, trinitrotoluene (TNT), cyclotrimethylenetrinitramine, 1,3,5-Trinitro-1,3,5-triazacyclohexane (RDX), and the like.

The ability to determine analytes (e.g., analytes comprising nitroaryl groups) can be useful in a variety of applications. In some cases, the nanosensors may be used to determine the presence of an explosive. For example, the nanosensors can be used to inspect an area suspected of containing land mines or other explosives, or to detect explosives at a security checkpoint. In some cases, the nanosensors may be used to detect pollutants containing nitroaryl containing compounds (e.g., pesticides).

In one set of embodiments, nanosensors comprising photoluminescent nanostructures, and methods for determined analytes are provided. As used herein, the term "nanostructure" refers to articles having at least one cross-sectional dimension between opposed boundaries of less than about 1 micron. In some embodiments, nanostructures can have at least one cross-sectional dimension between opposed boundaries of less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings, the atomic rings comprising a plurality of double bonds.

A "photoluminescent nanostructure," as used herein, refers to a class of nanostructures that are capable of exhibiting photoluminescence. In some embodiments, photoluminescent nanostructures exhibit fluorescence. In some instances, photoluminescent nanostructures exhibit phosphorescence. Examples of photoluminescent nanostructures suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, or graphene, among others. In some embodiments, the photoluminescent nanostructures can be a semi-conductive single-walled carbon nanotube.

In some embodiments, the systems and methods described herein may allow for selective determination of an analyte. The term "selective" is used to indicate an interaction that is sufficiently specific that it can be used to distinguish the analyte in practice from other chemical species in the system in which the nanosensor is to be employed. For example, in some cases, the nanosensors described herein can determine the presence of a nitroaryl containing compound (e.g., trinitrotoluene (TNT)) or a compound including one or more $NO_2$ groups (e.g., 1,3,5-Trinitro-1,3,5-triazacyclohexane (RDX)) without substantial interference from other compounds. In some embodiments, the target analyte may produce a change in photoluminescence of a nanostructure that is at least about 2 times, at least about 5 times, at least about 10 times, at least about 50 times, or at least about 100 times greater than the largest change in photoluminescence produced by another entity (e.g., a background molecule).

Figure 1B:
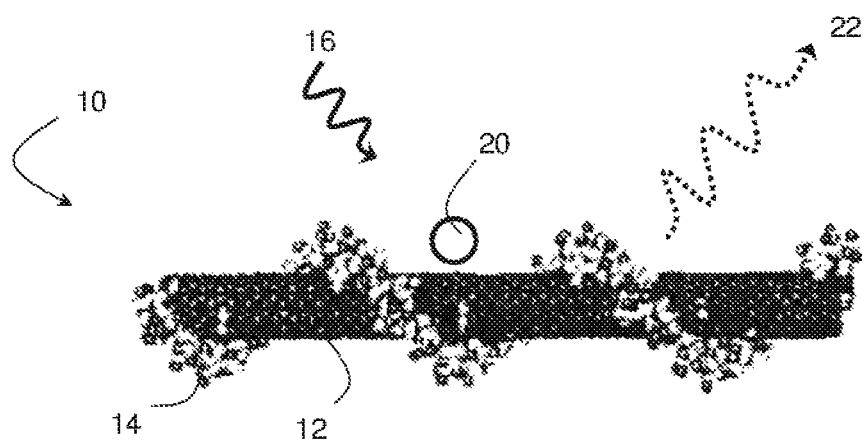
Figure 1C:
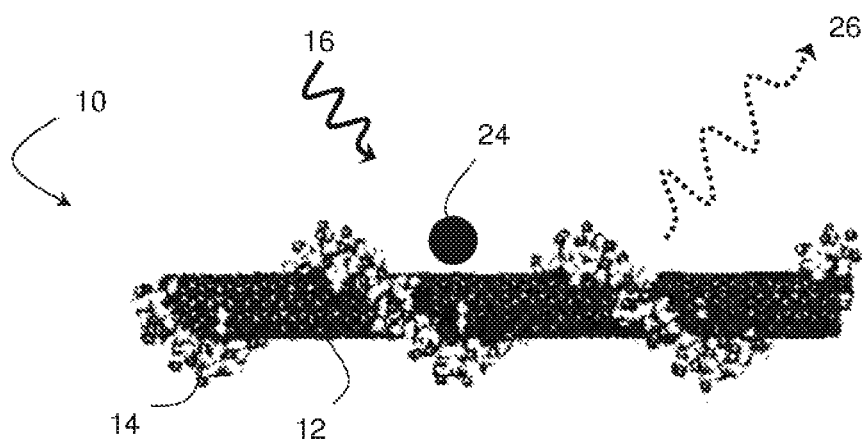

FIGS. 1A-1C include schematic diagrams of a nanosensor, according to one set of embodiments. In FIG. 1A, nanosensor 10 comprises photoluminescent nanostructure 12 and polymer 14 that interacts with the photoluminescent nanostructure. The photoluminescent nanostructure and the polymer can interact with each other, in some embodiments, via van der Waals forces (e.g., physisorption). In some embodiments, the photoluminescent nanostructure and the polymer are not covalently bonded to each other.

In some embodiments, the polymer may be capable of participating in a pi-pi interaction with the nanostructure. A pi-pi interaction (a.k.a., "pi-pi stacking") is a phenomenon known to those of ordinary skill in the art, and generally refers to a stacked arrangement of molecules adopted due to interatomic interactions. Pi-pi interactions can occur, for example, between two aromatic molecules. If the polymer comprises relatively large groups, pi-pi interaction can be reduced or eliminated due to steric hindrance. Hence, in certain embodiments, the polymer may be selected or altered such that steric hindrance does not inhibit or prevent pi-pi interactions. One of ordinary skill in the art can determine whether a polymer is capable or participating in pi-pi interactions with a nanostructure.

While polymer 14 is shown in FIGS. 1A-1C as being helically wrapped around nanostructure 12, it should be understood that the polymer may assume any suitable shape or conformation when interacting with the nanostructure. In some embodiments, the polymer may at least partially surround the nanostructure. A first entity is said to "at least partially surround" a second entity if a closed loop can be drawn around the second entity through only the first entity. In some cases, the polymer may be positioned proximate to the nanostructure such that it completely surrounds the nanostructure with the exception of relatively small volumes. The presence of these small volumes may allow for the passage of an analyte such that the analyte and the photoluminescent nanostructure can interact (e.g., via van der Waals forces, via electrical communication, etc.) while optionally preventing non-analyte entities from interacting with the photoluminescent nanostructure. A first entity is said to "completely surround" a second entity if closed loops going through only the first entity can be drawn around the second entity regardless of direction.

In some embodiments, the nanosensor may emit a first emission of electromagnetic radiation in the absence of an analyte. The first emission may be, in some cases, emitted in response to exposure of the nanosensor to electromagnetic radiation. For example, in the set of embodiments illustrated in FIG. 1A, incident electromagnetic radiation 16 interacts with the photoluminescent nanostructure, in the absence of an analyte, and the nanosensor emits a first emission of electromagnetic radiation 18. The emission of radiation can be a result of, for example, photo-induced band gap fluorescence.

For example, single-walled carbon nanotubes (e.g., semi-conductive single-walled carbon nanotubes) can exhibit band gap fluorescence when photo-induced by electromagnetic radiation. In some embodiments, the emission of radiation from a nanostructure can occur despite the substantial absence of a dopant or the substantial absence of a p-n junction within the nanostructure. For example, semi-conductive single-walled carbon nanotubes can exhibit photo-induced band gap fluorescence despite comprising no p-n junction or dopants.

One or more analytes may interact with the photoluminescent nanosensor, in some cases. For example, in the set of embodiments illustrated in FIG. 1B, first analyte 20 interacts with photoluminescent nanostructure 12 and/or polymer 14. Analytes can, in some cases, interact with photoluminescent nanosensor such that no covalent bonds are formed between the analyte and the photoluminescent nanostructure and/or between the analyte and the polymer. For example, in some embodiments, an analyte and the photoluminescent nanostructure and/or the polymer may interact via van der Waals forces.

In some embodiments, the nanosensor may emit a second emission of electromagnetic radiation upon interacting with an analyte (e.g., first analyte 20 in FIG. 1A). In some cases, the second emission may be distinguishable from an emission in the absence of any analyte or in the presence of a second, different analyte. A property of the electromagnetic radiation (e.g., intensity, wavelength, etc.) in the presence of an analyte may result due to an interaction between the analyte and the photoluminescent nanostructure and/or due to an interaction between the analyte and the polymer, in some cases. For example, in FIG. 1B, incident electromagnetic radiation 16 can interact with the nanosensor (e.g., via the photoluminescent nanostructure, via the polymer) to emit a second emission of radiation 22, which can be distinguishable from first emission of radiation 18.

In some embodiments, the nanosensor may emit a third emission of electromagnetic radiation upon interacting with a second analyte. For example, in the set of embodiments illustrated in FIG. 1C, second analyte 24 interacts with photoluminescent nanostructure 12 and/or polymer 14. In some cases, the third emission may be distinguishable from an emission in the absence of any analyte or from an emission (e.g., the second emission 22 in FIG. 1B) in the presence of the first analyte. For example, in FIG. 1C, incident electromagnetic radiation 16 can interact with the nanosensor (e.g., via the photoluminescent nanostructure, via the polymer) to emit a third emission of radiation 26, which can be distinguishable from first emission of radiation 18 and/or second emission of radiation 22.

In some cases, at least one wavelength within the second emission (in the presence of the first analyte) and/or the third emission (in the presence of the second analyte) is different (e.g., less intense, more intense) relative to the intensity of that wavelength in the first emission (in the absence of any analyte). The emission of a specific wavelength from a nanosensor can be determined, for example, by filtering the electromagnetic radiation such that one or more specific wavelengths of interest (or a band of wavelengths of interest) are separated from the other wavelengths. In some embodiments, the intensity of a plurality of or substantially all of the wavelengths within the second emission (in the presence of the first analyte) and/or the third emission (in the presence of the second analyte) are different than the intensities of the wavelengths in the first emission (in the absence of the analyte). For example, in some cases, the nanostructure may exhibit photoluminescence bleaching (i.e., a decrease in photoluminescent intensity) when associated with an analyte. In some embodiments, substantially no electromagnetic radiation is emitted by the nanostructure (e.g., after interacting with incident electromagnetic radiation) when it is interacting with an analyte. In addition, in some instances, at least one or substantially all of the wavelength(s) within the third emission (in the presence of the second analyte) can be different (e.g., less intense, more intense) relative to the corresponding wavelength(s) in the second emission (in the presence of the first analyte).

In some embodiments, the overall intensity of the first emission (in the absence of an analyte), second emission (in the presence of the first analyte), and/or third emission (in the presence of the second analyte) of electromagnetic radiation may be different. One of ordinary skill in the art would be capable of calculating the overall intensity by, for example, taking the sum of the intensities of the emissions over a range of wavelengths emitted by the sensor. In some cases, the nanosensor may have a first overall intensity in the absence of an analyte, and a second, lower overall intensity in the presence of a first analyte. In some cases, the nanosensor may emit a first emission of a first overall intensity in the presence of a first analyte, and a second emission of a second overall intensity that is different from the first overall intensity (e.g., larger, smaller) in the presence of a second analyte.

The nanosensor may, in some cases, emit an emission of radiation with one or more distinguishable peaks in the presence of an analyte. One of ordinary skill in the art would understand a peak to refer to a local maximum in the intensity of the electromagnetic radiation, for example, when viewed as a plot of intensity as a function of wavelength. In some embodiments, the nanosensor may, in the absence of an analyte, emit electromagnetic radiation with a specific set of peaks. In some cases, the presence of an analyte may cause the nanosensor to emit electromagnetic radiation comprising one or more peaks such that the peaks (e.g., the frequencies of the peaks, the intensity of the peaks) are distinguishable from one or more peaks observed in the absence of the analyte. In some cases, the presence of an analyte may cause the nanosensor to emit electromagnetic radiation comprising one or more peaks such that peaks (e.g., the frequencies of the peaks, the intensity of the peaks) are distinguishable from the one or more peaks observed in the presence of one or more other analytes. The frequencies and/or intensities of the peaks may, in some instances, allow one to determine the analyte interacting with the nanosensor by, for example, producing a signature that is unique to the particular analyte that is interacting with the nanosensor. Determination of the analyte can be accomplished, for example, by comparing the properties of the peaks emitted in the presence of the analyte to a set of data (e.g., a library of peak data for a predetermined list of analytes).

In some embodiments, a nanosensor can be simultaneously exposed to a plurality of analytes. This may result in the production of a multiplexed emission of electromagnetic radiation. In some cases, the multiplexed emission of electromagnetic radiation can be analyzed using principal component analysis (PCA) to determine each of the analytes. One of ordinary skill in the art would be familiar with PCA, which is described generally in Jolliffe I. T., *Principal Component Analysis*, Series: Spring Series in Statistics, $2^{nd}$ ed., Springer, N.Y., 2002, XXIX 487 p. 28 illus., ISBN 978-0-387-95442-4, which is incorporated by reference in its entirety.

In some instances, determining a compound may comprise the use of more than one photoluminescent nanostructure. For example, in some cases, a first photoluminescent nanostructure (e.g., a first single-walled carbon nanotube with a first chirality) may be exposed to at least one analyte, and a second photoluminescent nanostructure (e.g., a second single-walled carbon nanotube with a second chirality) may be exposed to the at least one analyte. Each of the analytes may interact with each of the nanostructures and/or a polymer interacting with the nanostructure to produce an emission of electromagnetic radiation. In some cases, the emissions of electromagnetic radiation can comprise one or more peaks, the properties of which may be used to determine an analyte. In some cases, the emissions of electromagnetic radiation can comprise distinguishable intensities, which may be used to determine an analyte. In some embodiments, the first photoluminescent nanostructure may have a first property (e.g., a first chirality, a first diameter, and/or a first optical bandgap) while the second photoluminescent nanostructure has a corresponding second property that is different from the first property (e.g., a second, different chirality; a second, different diameter; and/or a second, different optical bandgap).

The use of multiple nanosensors can be useful in distinguishing three or more analytes, in some cases. For example, in some embodiments, a first nanosensor may emit substantially identical emissions of electromagnetic radiation in the presence of first and second analytes, but a substantially different emission of electromagnetic radiation in the presence of a third analyte. Thus, the first nanosensor can be used to distinguish the third analyte from the first and second analytes. In some cases, the first and second analytes may subsequently be exposed to a second nanosensor. Upon interacting with the first and second analytes, the second nanosensor may produce first and second emissions of electromagnetic radiation, respectively. These first and second emissions may be sufficiently different such that the first and second analytes can be determined using the second nanosensor. It should be understood that such schemes can be used to determine any number of analytes (e.g., at least 3, at least 5, at least 10, at least 50, at least 100, or more) using any suitable number of nanosensors (e.g., at least 2, at least 3, at least 5, at least 10, at least 50, at least 100, or more).

In some embodiments, multiple nanosensors can be simultaneously exposed to multiple analytes, and the resulting multiplexed emissions of electromagnetic radiation can be analyzed to determine each of the analytes. In some embodiments, the analytes can be simultaneously determined using principal component analysis (PCA). In some such embodiments, each of the simultaneously exposed nanosensors can have a property (e.g., chirality, diameter, optical bandgap, etc.) that is different than the corresponding property in each of the rest of the plurality of simultaneously exposed nanosensors. As a specific example, in one set of embodiments, a first nanosensor can include a first single-walled carbon nanotube with a first chirality, and a second nanosensor can include a second single-walled carbon nanotube with a second chirality. The first and second nanosensors can be simultaneously exposed to first and second analytes to produce a change in the emissions of electromagnetic radiation from the nanosensors. The changes in the emissions from each of the nanosensors can then be processed using PCA to determine the first and second analytes using primary component analysis.

A variety of polymers may be used in association with the embodiments described herein. In some cases, the polymer may be a polypeptide such as, for example, an amphiphilic polypeptide. In some cases, the polypeptide may be a helical polypeptide. A "helical" polypeptide, as used herein describes a polypeptide in the substantial shape of a helix. One of ordinary skill in the art would be able to distinguish helical polypeptides from non-helical polypeptides. In some embodiments, the helical polypeptide may comprise a longitudinal axis that spans the length of the helix and is drawn through the hollow center of the helix. In some cases, every tangent line drawn from the polypeptide backbone may form an angle with the longitudinal axis that is within about a 10° range. Polypeptides may be useful for determining, for example, RDX, picric acid, 2,4-dinitrophenol, 4-nitro-3-(trifluoromethyl)phenol (TFM), and the like.

In some embodiments, the length and/or weight of the polypeptide may fall within a specific range. For example, the polypeptide may include, in some embodiments, between about 5 and about 50, or between about 5 and about 30 amino acid residues. In some cases, the polypeptide may have a molecular weight of between about 400 g/mol and about 10,000 g/mol, or between about 400 g/mol and about 600 g/mol.

The polypeptide may, in some instances, include a peptide sequence observed in the venom of an animal or a derivative thereof. In some cases, the polymer may include a polypeptide sequence (or derivative thereof) observed in the venom of a member of the Insecta class, the Hymenoptera order, or the Vespidae or Apidae families. In some embodiments, the polypeptide may be a member the Mastoparan or Bombolitin (e.g., Bombolitin II, Bombolitin III) families of polypeptides, or derivatives of those polypeptides. Exemplary polypeptides suitable for use herein include, but are not limited to, KKAAAVLLPVLLAAP (SEQ ID NO: 1), EEEECCCCHSSYWYAFNNKT (SEQ ID NO: 2), INLKALAALAKKIL (SEQ ID NO: 3), INLKALAALAKALL (SEQ ID NO: 4), INWKGIAAMAKKLL (SEQ ID NO: 5), IKIMDILAKLGKVLAHV (SEQ ID NO: 6), INIKDILAKLVKVLGHV (SEQ ID NO: 7), IKITTMLAKLGKVLAHV (SEQ ID NO: 8), or SKITDILAKLGKVLAHV (SEQ ID NO: 9). Amino acid residues are generally referred to herein using the following standard 1-letter abbreviations: Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V).

In some embodiments, the polymer may include an oligonucleotide. The oligonucleotide can be, in some cases, a single-stranded DNA oligonucleotide. The single-stranded DNA oligonucleotide can be, in some cases, at least 5 repeating units, in succession, of (GT), (AT), (AAAAT), or (GGGGT). As an illustrative example, a single-stranded DNA oligonucleotide including 5 repeating units of GGGGT would include the nucleobase sequence GGGGTGGGGTGGGGTGGGGTGGGGT (SEQ ID NO: 12), and is abbreviated herein as d(GGGGT)$_5$. In some embodiments, the single-stranded DNA oligonucleotide can be, in some cases, at least 5, at least 10, at least 15, between 5 and 25, between 5 and 15, or between 5 and 10 repeating units, in succession, of (GT) or (AT). The nucleobases described herein are given their standard one-letter abbreviations: cytosine (C), guanine (G), adenine (A), and thymine (T). Oligonucleotides can be particularly useful in determining, in some cases, TNT.

In some embodiments, the polymer may comprise a polysaccharide such as, for example, dextran, amylose, chitin, or cellulose. In some embodiments, the polymer may comprise a protein. Examples of suitable proteins include, but are not limited to glucose oxidase, bovine serum albumin and alcohol dehydrogenase. The polymer may also comprise a synthetic polymer (e.g., polyvinyl alcohol, poly(acrylic acid), poly(ethylene oxide), poly(vinyl pyrrolidinone), poly(allyl amine), poly(2-vinylpyridine), poly(maleic acid), and the like), in some embodiments.

In some cases, the polymer can adopt a shape such that it allows the analyte to interact with the photoluminescent nanostructure, but inhibits other molecules from interacting with the photoluminescent nanostructure. For example, after the polymer adopts the shape, interactions between the analyte and the photoluminescent nanostructure can be relatively energetically favored, while interactions between the photoluminescent nanostructure and non-analyte entities can be relatively energetically disfavored (e.g., due to steric hindrance). In some cases, the polymer may comprise pendant groups that, upon interacting with the photoluminescent nanostructure, transform the shape of the polymer relative to the shape the polymer would possess in the absence of the interaction with the photoluminescent nanostructure, such that the polymer at least partially surrounds the photoluminescent nanostructure. The transformed shape of the polymer may comprise openings through which the analyte can pass (e.g., due to being energetically favored) and interact with the photoluminescent nanostructure, in some cases. Also, in some embodiments, the openings may reduce or eliminate interaction between the photoluminescent nanostructure and at least one or substantially all background entities (e.g., due to being energetically disfavored). In some cases, the polymer can comprise pendant groups that enhance the selective passage of the analyte described above (e.g., via steric effects) without interacting with the photoluminescent nanostructure.

In some embodiments, the photoluminescent nanostructure may be substantially free of covalent bonds with other entities (e.g., other nanostructures, a current collector, the surface of a container, a polymer, an analyte, etc.). The absence of covalent bonding between the photoluminescent nanostructure and another entity may, for example, preserve the photoluminescent character of the nanostructure. In some cases, single-walled carbon nanotubes or other photoluminescent nanostructures may exhibit modified or substantially no fluorescence upon forming a covalent bond with another entity (e.g., another nanostructure, a current collector, a surface of a container, and the like).

In some embodiments, the interaction between an analyte and a nanosensor may be reversible. Not wishing to be bound by any theory, the reversibility of the interaction between an analyte and a nanosensor may be due, in some cases, to the non-covalent interaction between the analyte and the nanosensor. In some embodiments, the interaction between an analyte and a nanosensor can be reversed without breaking any covalent bonds between the analyte and the nanosensor. For example, in some cases, the interaction between the nanosensor and the analyte can be reversed via dialysis of the analyte-adsorbed nanosensor. One of ordinary skill in the art would be familiar with the process of dialysis, which generally refers to the process of separating entities (e.g., analyte and nanosensor) in a fluid (e.g., in solution) based upon differences in their rates of diffusion through a membrane (e.g., a semipermeable membrane). The ability to reverse the interaction between the analyte and the nanosensor can allow for re-use of the nanosensor after it has been exposed to an analyte.

An analyte and/or polymer can be, in some cases, in electrical communication with the photoluminescent nanostructure. In some embodiments, the analyte and/or polymer can be in direct electrical communication with the photoluminescent nanostructure. As used herein, two entities are said to be in "direct electrical communication" with each other when they are capable of directly exchanging electrons with each other, without the electrons passing through a third entity. In contrast, "indirect electrical communication" refers to situations in which first and second entities are capable of exchanging electrons with each other only via a third entity. In some cases, the polymer and/or analyte may donate electrons to the photoluminescent nanostructure, producing excess electrons on the nanostructure. Such electron transfer may alter the way in which the nanostructure participates in direct electrical communication with an analyte. For example, in some embodiments, the analyte and/or polymer may comprise lone pairs of electrons on a pendant group which can be transferred to the nanostructure and subsequently transferred to the analyte. Such electron transfer from the nanostructure to the analyte can produce, in some embodiments, a change in the luminescent nature of the nanostructure (e.g., photoluminescent bleaching).

In some embodiments, the systems and methods described herein may be capable of determining relatively low concentrations of an analyte. The ability to determine low concentrations of an analyte may be useful, for example, in detecting trace pollutants or trace amounts of toxins within a subject. In some embodiments, nanosensors can determine analyte concentrations of less than about 100 micromolar, less than about 10 micromolar, less than about 1 micromolar, less than about 100 nanomolar, less than about 10 nanomolar, or less than about 1 nanomolar. In some cases, nanosensors can be used to determine a single molecule of an analyte.

In some embodiments, the nanosensor may be exposed to electromagnetic radiation. In some cases, the electromagnetic radiation can be near-infrared radiation. Sources of electromagnetic radiation that can be used include, but are not limited to, a lamp (e.g., an infrared lamp, ultraviolet lamp, etc.), a laser, LED, or any other suitable source. In addition, the method may further comprise sensing electromagnetic radiation (e.g., the intensity and/or wavelength) or the absorption of electromagnetic radiation, for example, emitted by the nanosensor. Sensing can be performed using, for example, a UV-vis-nIR spectrometer, a florometer, a fluorescence microscope, visual inspection (e.g., via observation by a person) or any other suitable instrument or technique.

In yet another aspect, a method of making a photoluminescent nanosensor is provided. The method of making the nanosensor may comprise, in some cases, exposing a photoluminescent nanostructure to a polymer capable of interacting with the photoluminescent nanostructure (e.g., via any of the mechanisms described above). In some embodiments, the photoluminescent nanostructure, the polymer or both may be provided within a fluid (e.g., a liquid). For example, exposing a photoluminescent nanostructure to the polymer can comprise adding the polymer to a fluid containing a photoluminescent nanostructure. Exposing a photoluminescent nanostructure to a polymer can also comprise adding a photoluminescent nanostructure to a fluid containing a polymer, in some cases. One of ordinary skill in the art will be able to identify other suitable methods for exposing a photoluminescent nanostructure to a polymer.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles (e.g., cells, vesicles, etc.), viscoelastic fluids, and the like. In some embodiments, the fluid may comprise water, chloroform, acetonitrile, N-methyl pyrrolidone (NMP), or any other suitable fluid in which nanostructures (e.g., carbon nanotubes) can be suspended. In some embodiments, a fluid may be selected that is capable of forming a stable suspension of photoluminescent nanostructures (e.g., single-walled carbon nanotubes).

The term "determining," as used herein, generally refers to the analysis or measurement of a species (e.g., an analyte), for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. For example, in some embodiments, determining a species (e.g., an analyte) comprises determining the identity of the species. In some cases, determining the species comprises determining the concentration of the species, instead of or in addition to determining the identity of the species.

As described above, a variety of nanostructures can be used in association with the nanosensors described herein. In some embodiments, carbon-based nanostructures can be used. As used herein, a "carbon-based nanostructure" comprises a fused network of aromatic rings wherein the nanostructure comprises primarily carbon atoms. In some instances, the nanostructures have a cylindrical, pseudo-cylindrical, or horn shape. A carbon-based nanostructure can comprises a fused network of at least about 10, at least about 50, at least about 100, at least about 1000, at least about 10,000, or, in some cases, at least about 100,000 aromatic rings. Carbon-based nanostructures may be substantially planar or substantially non-planar, or may comprise a planar or non-planar portion. Carbon-based nanostructures may optionally comprise a border at which the fused network terminates. For example, a sheet of graphene comprises a planar carbon-containing molecule comprising a border at which the fused network terminates, while a carbon nanotube comprises a nonplanar carbon-based nanostructure with borders at either end. In some cases, the border may be substituted with hydrogen atoms. In some cases, the border may be substituted with groups comprising oxygen atoms (e.g., hydroxyl). In other cases, the border may be substituted as described herein.

In some embodiments, the nanostructures described herein may comprise nanotubes. As used herein, the term "nanotube" is given its ordinary meaning in the art and refers to a substantially cylindrical molecule or nanostructure comprising a fused network of primarily six-membered rings (e.g., six-membered aromatic rings). In some cases, nanotubes may resemble a sheet of graphite formed into a seamless cylindrical structure. It should be understood that the nanotube may also comprise rings or lattice structures other than six-membered rings. Typically, at least one end of the nanotube may be capped, i.e., with a curved or nonplanar aromatic group. Nanotubes may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may comprise a carbon nanotube. The term "carbon nanotube" refers to nanotubes comprising primarily carbon atoms. Examples of carbon nanotubes include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like.

In some embodiments, the carbon nanotube is a single-walled carbon nanotube. In some cases, the carbon nanotube is a multi-walled carbon nanotube (e.g., a double-walled carbon nanotube).

In some embodiments, the nanostructures comprise non-carbon nanotubes. Non-carbon nanotubes may be of any of the shapes and dimensions outlined above with respect to carbon nanotubes. The non-carbon nanotube material may be selected from polymer, ceramic, metal and other suitable materials. For example, the non-carbon nanotube may comprise a metal such as Co, Fe, Ni, Mo, Cu, Au, Ag, Pt, Pd, Al, Zn, or alloys of these metals, among others. In some instances, the non-carbon nanotube may be formed of a semiconductor such as, for example, Si. In some cases, the non-carbon nanotubes may be Group II-VI nanotubes, wherein Group II consists of Zn, Cd, and Hg, and Group VI consists of O, S, Se, Te, and Po. In some embodiments, non-carbon nanotubes may comprise Group III-V nanotubes, wherein Group III consists of B, Al, Ga, In, and Tl, and Group V consists of N, P, As, Sb, and Bi. As a specific example, the non-carbon nanotubes may comprise boron-nitride nanotubes.

In some embodiments, the nanotube may comprise both carbon and another material. For example, in some cases, a multi-walled nanotube may comprise at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and is used to refer to semi-conducting nanostructures that exhibit quantum confinement effects. Generally, energy (e.g., light) incident upon a quantum dot will excite the quantum dot to an excited state, after which, the quantum dot will emit energy corresponding to the energy band gap between its excited state and its ground state. Examples of materials from which quantum dots can be made include PbS, PbSe, CdS, CdSe, ZnS, or ZnSe, among others.

The photoluminescent nanostructures described herein can be, in some cases, substantially free of dopants, impurities, or other non-nanostructure atoms. For example, in some embodiments, the nanostructure can comprise a carbon nanostructure that is substantially free of dopants. As a specific example, in some embodiments, the nanostructures may comprise single-walled carbon nanotube that contain only aromatic rings (each of which contains only carbon atoms) within the shell portion of the nanotube.

In some embodiments, the photoluminescent nanostructures described herein may emit radiation within a desired range of wavelengths. For example, in some cases, the photoluminescent nanostructures may emit radiation with a wavelength between about 750 nm and about 1600 nm, or between about 900 nm and about 1400 nm (e.g., in the near-infrared range of wavelengths). In some embodiments, the photoluminescent nanostructures may emit radiation with a wavelength within the visible range of the spectrum (e.g., between about 400 nm and about 700 nm).

In some embodiments, a kit including one or more of the compositions previously discussed (e.g., a kit including a nanosensor, a kit including a polymer and a photoluminescent nanostructure from which a nanosensor can be produced, etc.) that can be used to produce and/or employ a nanosensor, is described. A "kit," as used herein, typically defines a package or an assembly including one or more of the compositions of the invention, and/or other compositions associated with the invention, for example, as previously described. Each of the compositions of the kit may be provided in liquid form (e.g., a suspension of nanosensors, etc.), or in solid form. In certain cases, some of the compositions may be constitutable or otherwise processable, for example, by the addition of a suitable solvent, other species, or source of energy (e.g., electromagnetic radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

EXAMPLES

The following examples are intended to illustrate certain embodiments of the present invention, but do not exemplify the full scope of the invention.

Example 1

Polymer-encapsulated nanotube complexes were used to detect and identify analytes containing nitroaryl groups, including two pesticide compounds and three explosives. The encapsulating polymers included polyvinylpyrrolidone (PVP), a single-stranded DNA oligonucleotide, and polypeptides. The peptide sequences were three variants of mastoparan, a 14-residue peptide derived from wasp venom with the sequences INLKALAALAKKIL-NH$_2$, INLKA- LAALAKALL-NH$_2$, and INWKGIAAMAKKLL-NH$_2$, as well as bombolitin II, a 17-residue mast cell degranulating peptide with the sequence SKITDILAKLGKVLAHV (SEQ ID NO: 9). The oligonucleotide was the 30-nucleobase single-stranded repeating DNA sequence d(GT)$_{15}$ (SEQ ID NO: 10).

The nanotubes were encapsulated in peptides and DNA coatings by mixing them with raw HiPCO SWNT (Rice University) in a polymer:nanotube mass ratio of 2:1 in 1 mL of Tris buffer containing 20 mM Tris and 0.1 M NaCl (or 0.1 M NaCl for the DNA) in a microcentrifuge tube and applying high-intensity ultrasonication with a ⅛" probe-tip for 10 minutes at 10 W in a 4° C. ice bath. The solutions were then centrifuged twice at 16,000 g for 90 minutes where the pellet was discarded after centrifugation, resulting in stable biopolymer-SWNT complexes. Nanotubes were encapsulated in PVA by first suspending them in 2% sodium cholate via cup-horn sonication for 10 minutes and ultracentrifugation for 4 hours at 100,000 g. This solution was mixed with PVA in a PVA:SWNT mass ratio of 200:6. The mixture was dialyzed overnight against water.

The complexes were tested against the target analytes in a solution of Tris buffer, 1-2 mg/L of the nanotube-polymer complex, and the analyte. Analyte concentrations tested were: RDX: 180 micromolar, 2,4,-dinitrophenol: 308 micromolar, TNT: 4.4 micromolar, picric acid: 56.7 micromolar, and 4-nitro-3(trifluoromethyl)phenol: 197 micromolar. The photoluminescence of the nanotubes under 785 nm laser excitation was detected via an Acton SP-150 spectrograph coupled to a Princeton Instruments OMA V InGaAs detector.

Figure 2:
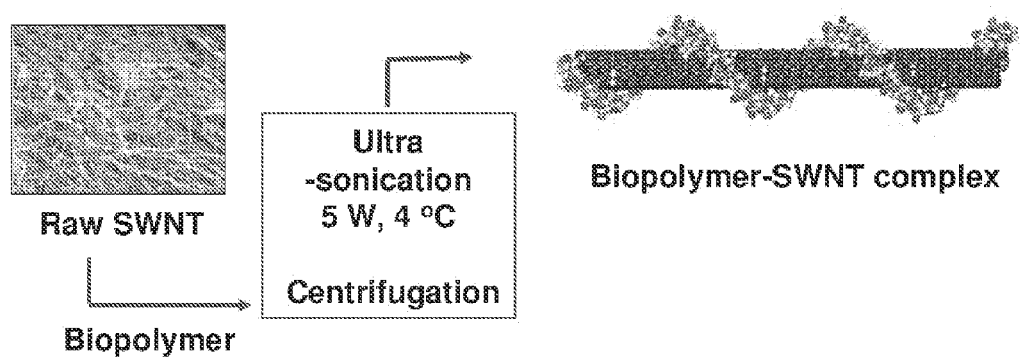
FIG. 2 is a schematic diagram of a general method of preparing a biopolymer-SWNT complex.

Near-infrared spectra of the polymer-bound nanotubes showed multiple emission bands with each one accorded to a single SWNT species (FIG. 2). Upon interaction with a nitroaryl compound, the spectra exhibited wavelength shifts and intensity variations which differed depending on the analyte/wrapping combination. The figure illustrates the response of mastoparan and mastoparan-7 encapsulated SWNT to pesticides 2,4-dinitrophenol and 4-nitro3(trifluoromethyl)phenol, as well as to the explosive picric acid. Although the same encapsulating polymer may allow nanotubes to respond to multiple analytes, the analyte polymer interactions resulted in different response behaviors of the nanotube emission bands. The unique responses of each analyte-wrapping interaction can permit analyte identification based on spectral signature.

Figure 3:
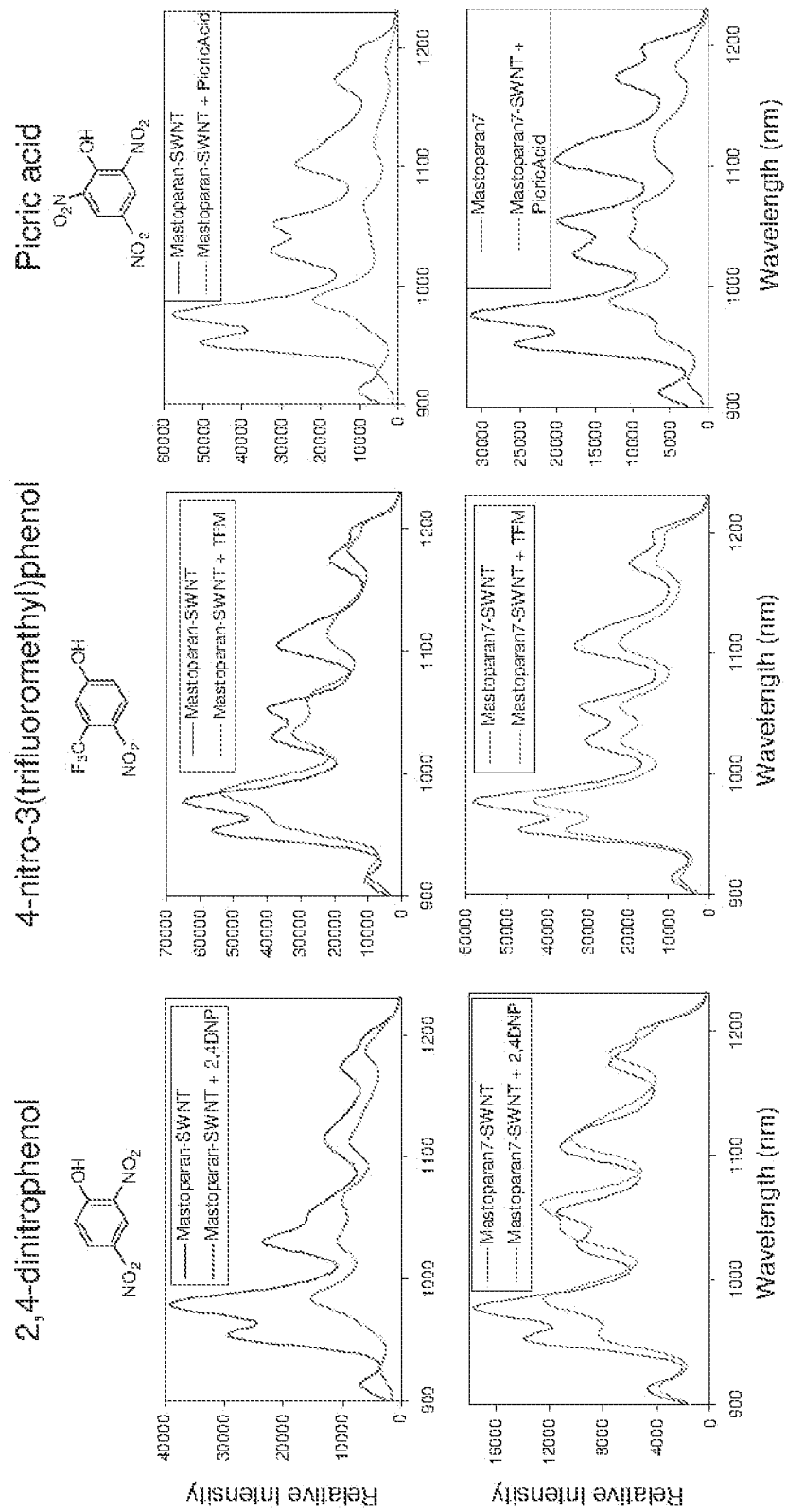
FIG. 3 presents near-infrared spectra of polymer-bound nanotubes in the prescence or absence of different nitroaryl compounds.

The nitroaryl compound 2,4-dinitrophenol exhibited strong wavelength responses to the exclusion of 53 other compounds (listed in Table 1) which did not contain nitroaryl groups, upon interaction with mastoparan-7 bound SWNT (FIG. 3). This demonstrates the ability of the sensors to avoid false positive incidences.

TABLE 1

List of analyte screening compounds used in FIG. 2.

| # | Compound | Conc (mM) | # | Compound | Conc (mM or %) |
|---|---|---|---|---|---|
| 1 | Control | 0 | 30 | Mannose | 5 |
| 3 | 2,4-dinitrophenol | 0.31 | 31 | Melatonin | 0.1 |
| 4 | Acetylcholine chloride | 5 | 33 | Pesticides mix | 0.5 |
| 5 | Adenosine | 1 | 34 | Potassium carbonate | 5 |
| 6 | Alpha tocopherol | 0.1 | 35 | Potassium chloride | 5 |
| 7 | Ascorbic acid | 5 | 36 | Quinine sulfate dihydrate | 0.5 |
| 8 | ATP | 5 | 37 | Riboflavin | 0.06 |
| 9 | β-NAD | 5 | 38 | Salicylic acid | 1 |
| 10 | Calcium chloride | 5 | 39 | Serotonin creatinine sulfate complx | 1 |
| 11 | cAMP | 5 | 40 | Sodium azide | 5 |
| 12 | Citrulline | 5 | 41 | Sodium bicarbonate | 5 |
| 14 | Creatinine | 5 | 42 | Sodium chloride | 5 |
| 15 | Cytidine | 5 | 43 | Sodium citrate | 5 |
| 16 | D-Aspartic Acid | 1 | 44 | Sodium nitrate | 5 |
| 18 | Dopamine hydrochloride | 5 | 45 | Sodium nitrite | 5 |
| 19 | Glucose | 5 | 46 | Sodium pyruvate | 5 |
| 20 | Glutamine | 5 | 48 | Tryptophan | 1 |
| 21 | Glycine | 5 | 49 | Tyramine | 5 |
| 22 | Guanosine | 0.29 | 50 | Uracil | 5 |
| 23 | Histamine | 5 | 51 | Urea | 5 |
| 24 | Histidine | 5 | 52 | Galactose | 5 |
| 25 | Hydrogen peroxide | 5 | 53 | Frucose | 5 |
| 26 | L-deoxy-D-glucose | 5 | 54 | DMSO | 50% |
| 27 | Lithium chloride | 5 | 55 | Ethanol | 50% |
| 28 | L-thyroxine | 0.026 | 56 | Methanol | 50% |
| 29 | Magnesium chloride | 5 | 57 | Control 2 | 0 |

Skipped numbers contain no analyte in the corresponding plot.

Seven nitroaryl compounds elicited spectroscopically differentiable signals when introduced to the encapsulated SWNT. These include the explosives TNT and RDX (FIG. 4), whose wavelength and intensity responses to 12 different nanotube/wrapping combinations (for list see Table 2) show unique combinations of shift and intensity variations. Thus, several important explosives can be detected and identified in real time.

TABLE 2

Figure 4:
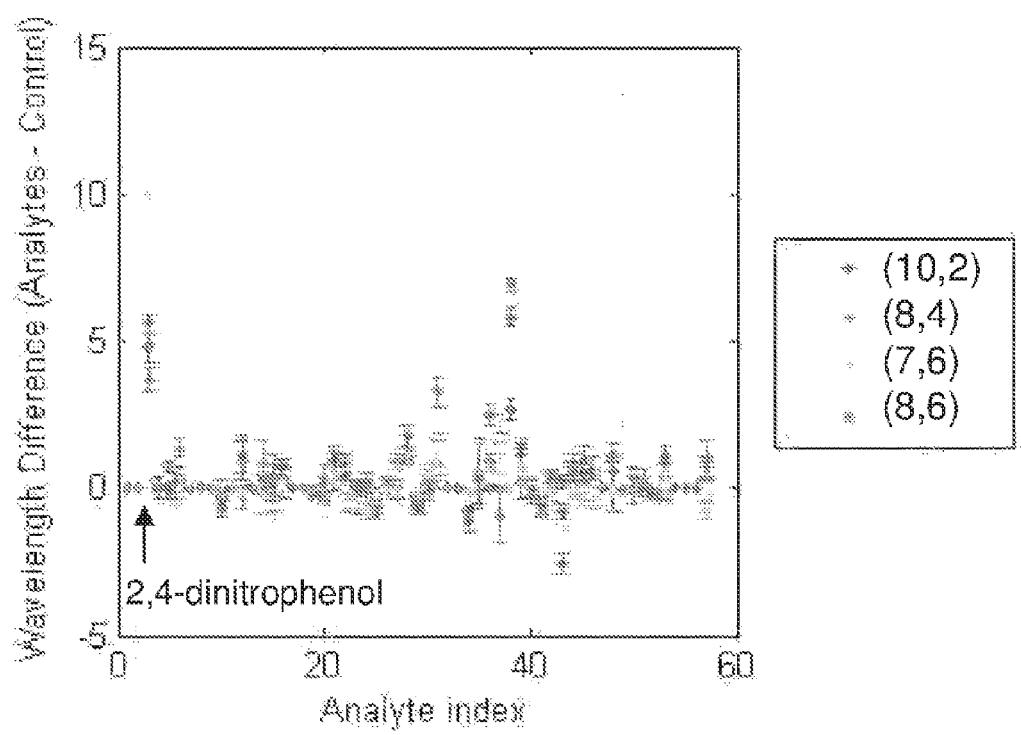
FIG. 4 is a graph depicting wavelength response for each of several different nanotubes with various analytes.
Figure 5:
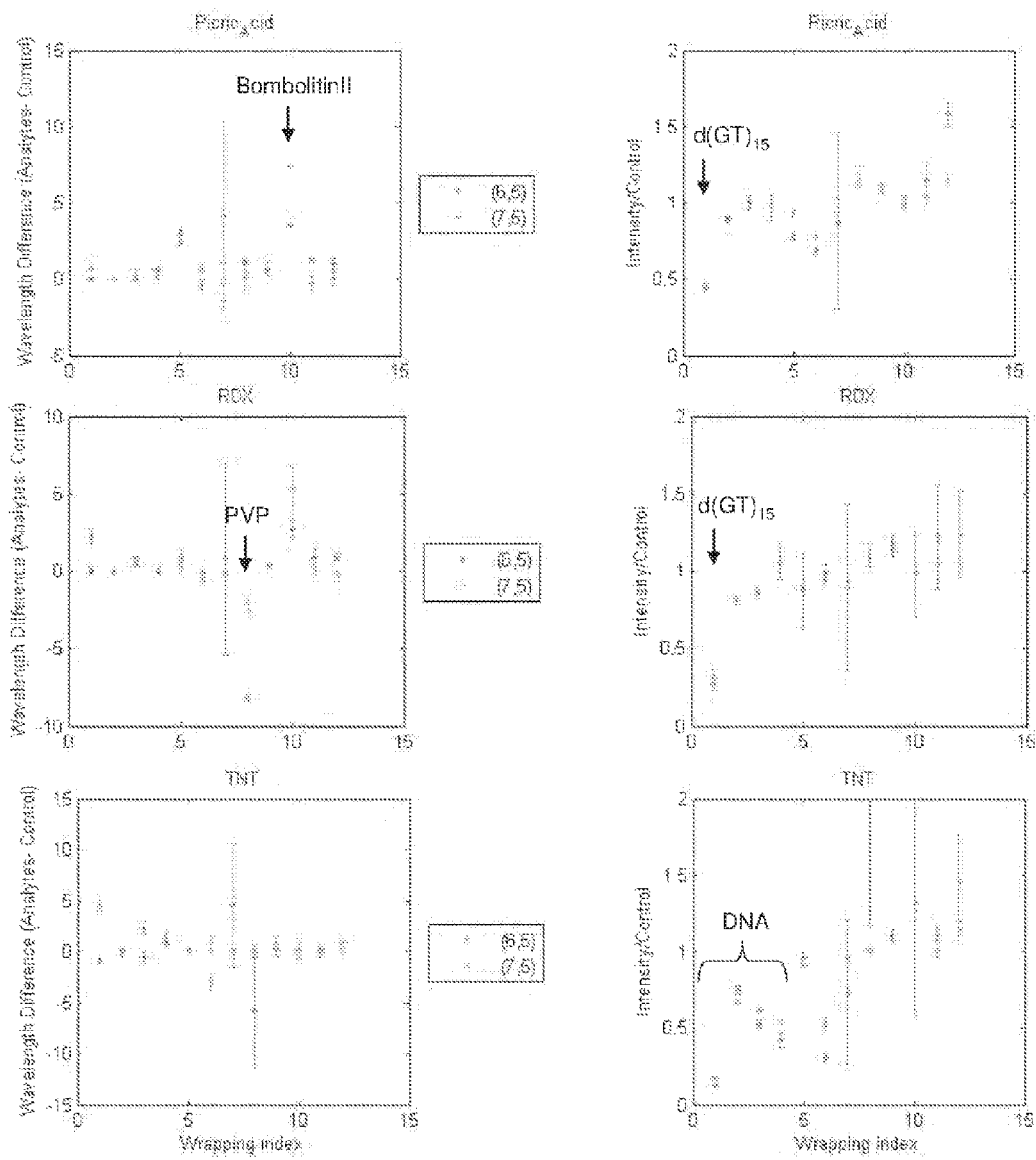
FIG. 5 presents a series of graphs summarizing changes to the near-IR spectra of various SWNT wrappings when exposed to different analytes (e.g., picric acid, RDX, and TNT).

List of SWNT wrappings used in FIG. 4.

| | |
|---|---|
| 1 | d(GT)$_{15}$ (SEQ ID NO: 10) |
| 2 | d(AT)$_{15}$ (SEQ ID NO: 11) |
| 3 | d(AAAAT)$_6$ (SEQ ID NO: 19) |
| 4 | d(GGGGT)$_6$ (SEQ ID NO: 20) |
| 5 | Phenylated Dextran |
| 6 | Peptide Sequence: EEEECCCC HSSYWYAFNNKT (SEQ ID NO: 2) |
| 7 | Collagen |
| 8 | PVP |
| 9 | PVA |
| 10 | Bombolitin II |
| 11 | Bombolitin III |
| 12 | Peptide Sequence: KKAAAVLLPVLLAAP (SEQ ID NO: 1) |

Example 2

In this example, a series of polymers and biopolymers were used to encapsulate SWNT for nitro compound detection, including polyvinyl alcohol (PVA) and the $d(GT)_{15}$ DNA oligonucleotide (SEQ ID NO: 10), as well as peptides, which selectively detected and transduced the binding of nitro group-containing compounds. The bombolitin family of oligopeptides contains five species with 17-residue sequences derived from bumblebee venom. The sequences of the variants used here are bombolitin I: IKITTMLAKLGKVLAHV (SEQ ID NO: 8), bombolitin II: SKITDILAKLGKVLAHV (SEQ ID NO: 9), bombolitin III: IKIMDILAKLGKVLAHV (SEQ ID NO: 6), and bombolitin IV: INIKDILAKLVKV-LGHV (SEQ ID NO: 7). Their conformations can be largely disordered in aqueous solution; in the presence of bilipid membranes, they can take on a more ordered, alpha helical structure according to circular dichorism studies. At high concentrations, above 2.5 mM for bombolitin III for instance, and higher for other sequences, the peptides can form aggregates with an anti-parallel alpha-helical conformation.

This example investigates two mechanisms for nitro-containing species to be selectively recognized by biopolymer-encapsulated SWNT. Trinitrotoluene (TNT) was detected via redox-induced bleaching while other nitro compounds, including RDX, picric acid, and two pesticides, were recognized and identified by a class of helix-coil peptides which underwent a conformational change upon binding to the analyte compound, resulting in a solvatochromic shift of the nanotube photoluminescence (PL). The work constitutes an optical sensor for real-time explosives detection, with the abilities of analyte fingerprinting and single-molecule sensitivity. This example also demonstrates carbon nanotube-based optical sensor which detects a peptide secondary structure change.

Wrapping-Mediated Responses to Redox-Active Compounds

It was found that altering the polymer or peptide wrapping around a single walled carbon nanotube modulateed analyte responsiveness. A comparison was performed between the spectral fluorescent intensity and wavelength changes of several polymer and peptide wrapped SWNT upon exposure to an array of various analytes.

Figure 6:
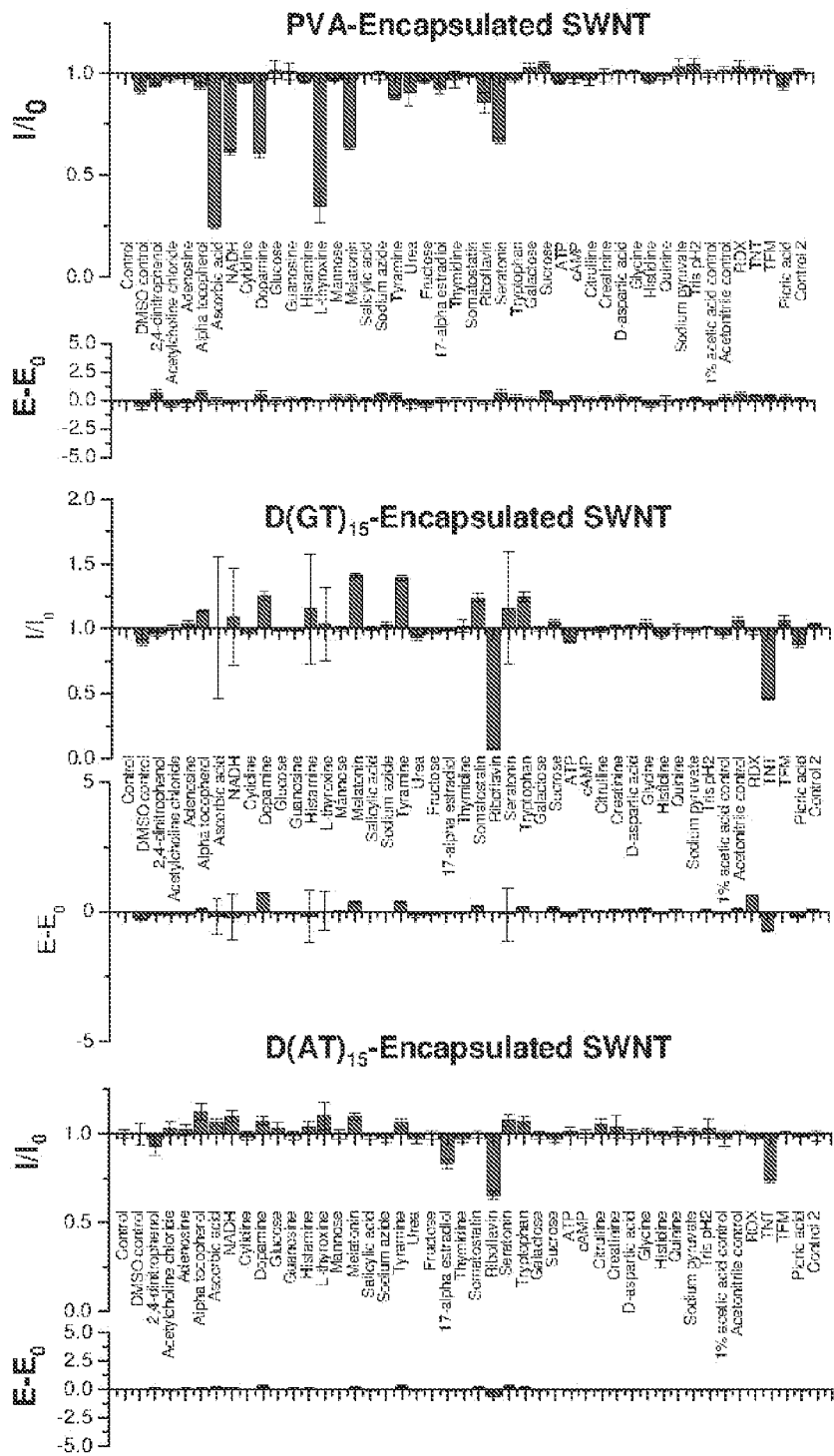
FIG. 6 presents a series of graphs summarizing changes in the near-IR spectra of PVP- or $d(GT)_{15}$-encapsulated SWNTs when exposed to various redox-active analytes.

Measurements were conducted on nanotubes solubilized with several polymers, which highlighted the polymer's role in permitting detection specificity. Solvatochromic shifts from a particular analyte can be rare. The (7,5) nanotube, solubilized by polyvinyl alcohol (PVA-SWNT), experienced intensity attenuation upon exposure to certain analytes (ascorbic acid, NADH, dopamine, L-thyroxine, melatonin, and seratonin) (FIG. 6, top).

Upon introduction of the analytes to nanotubes encapsulated by the $d(GT)_{15}$ oligonucleotide (SEQ ID NO: 10) (FIG. 6, middle), many of the same compounds caused intensity changes as with PVA-SWNT, with the addition of tyramine, riboflavin, tryptophan, and trinitrotoluene (TNT). Some analytes induced a signal increase, with the exceptions of riboflavin and TNT, which induced the sole quenching effects on this nanotube complex. Introduction of the analyte set to nanotubes encapsulated by the $d(AT)_{15}$ oligonucleotide (SEQ ID NO: 11) ($d(AT)_{15}$-SWNT) (FIG. 6, bottom) results in a different profile, with riboflavin, alpha tocopherol, and trinitrotoluene (TNT) exhibiting a quenching response and concomitantly preventing others.

We find that encapsulation of SWNT by $d(AT)_{15}$ (SEQ ID NO: 11) allows selective molecular recognition of TNT among nitroaromatics. Upon probing the complex with 13 nitro group compounds (FIG. 7A), the PL exhibits quenching in response to TNT and attenuates slightly in response to 2,4-dinitrotoluene and 2-nitrophenol, to the exclusion of the other analytes.

Figure 7:
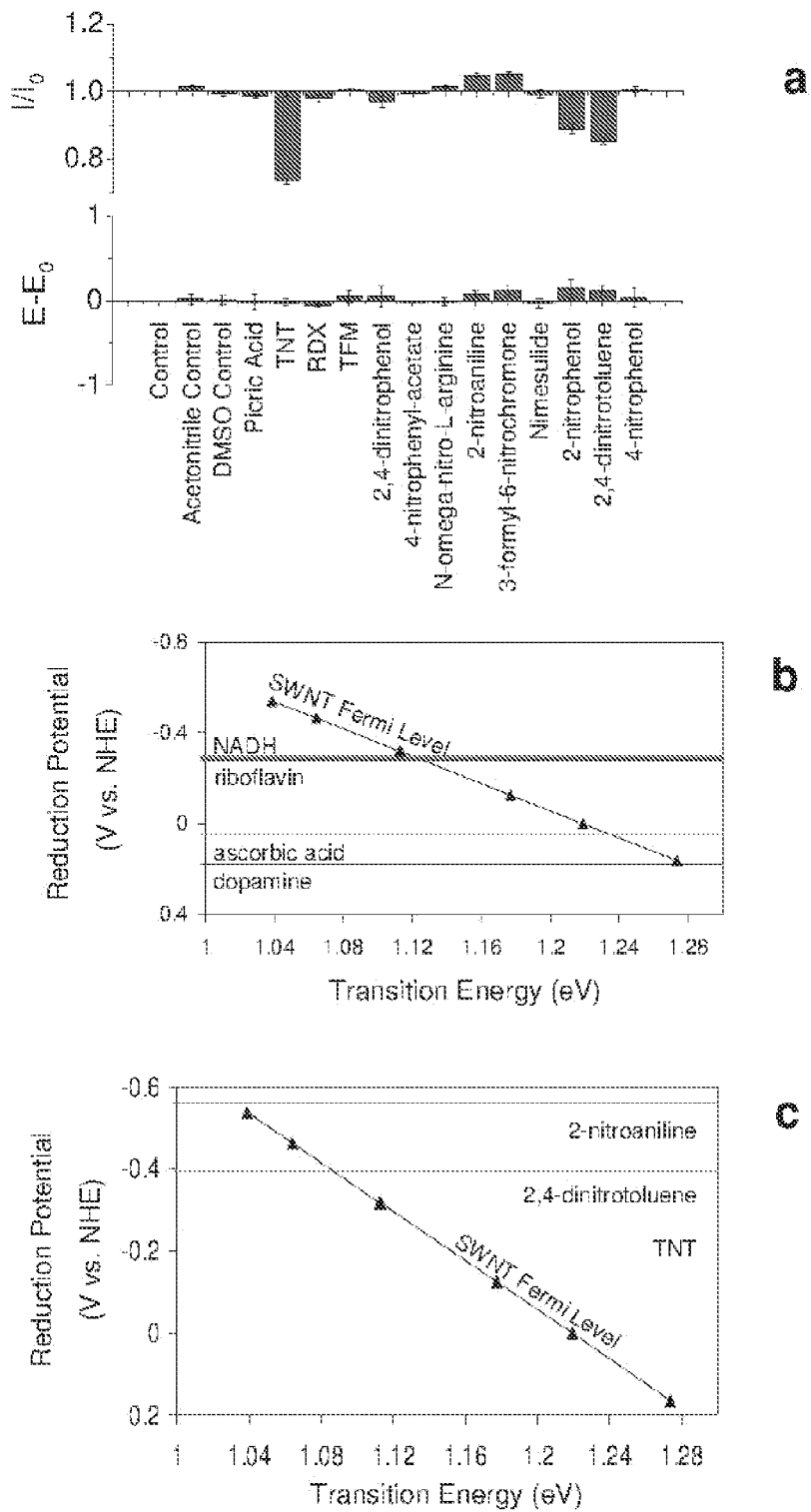
FIG. 7A summarizes changes to the near-IR spectra of SWNTs when exposed to different nitroaryl compounds.
FIGS. 7B-7C plot the relative position of the Fermi level for different carbon nanotube species.

Photoluminescence intensity attenuation responses to redox-active compounds may have been due, in some cases, to electron transfer events which shift the Fermi level of the nanotube, resulting in spectral bleaching. This mechanism may explain the PVA and $d(GT)_{15}$ DNA (SEQ ID NO: 10) encapsulated SWNT analyte responses. FIG. 7 plots the relative position of the Fermi level for each carbon nanotube species. Reduction potentials of several analytes vs. the normal hydrogen electrode (NHE) were obtained from the literature and appear as horizontal lines. Attenuating analytes dopamine, riboflavin, 3-hydroxytyramine, ascorbic acid, and NADH exhibited higher reduction potentials than the Fermi levels of several nanotube species, signifying the possibility of charge transfer to the nanotube. Nanotubes encapsulated by the $d(GT)_{15}$ oligonucleotide (SEQ ID NO: 10) responded selectively to TNT, which elicited a quenching response (FIG. 8). 2,4-dinitrotoluene and 2-nitrophenol also quenched to lesser degrees. There were also few wavelength shifting responses. The reduction potentials of three nitro compound-containing analytes are shown as horizontal lines in FIG. 7C to compare to the SWNT Fermi level. The relative reduction potentials follow the analyte responses, as TNT and 2,4-dinitrotoluene are positioned to withdraw electron density from several SWNT species, while 2-nitroanaline is not. The non-bleaching analyte salycilic acid exhibited a reduction potential well below the SWNT Fermi level.

Absorption spectroscopy of $d(AT)_{15}$-SWNT interacting with TNT does not exhibit attenuation of the SWNT absorption bands (FIG. 8A), as compared to a significant drop in PL emission on exposure to the same conditions (FIG. 8A inset), denoting a lack of spectral bleaching. We thus infer the sensing mechanism to be excitonic PL quenching of SWNT and conclude that doping of the adsorbed oligonucleotide modulates the exciton quenching. The response fits a $1^{st}$ order Langmuir adsorption isotherm (FIG. 8B), suggesting reversible behavior.

Stochastic, single-molecule detection of TNT is achieved by real-time PL measurement of $d(AT)_{15}$-SWNT adhered to a glass surface. The time-trace of the emission of one SWNT (FIG. 9A) exhibits discrete quenching and de-quenching steps with quantized step heights, signifying single-molecule adsorption and desorption events, and confirming sensor reversibility. A histogram of step heights (FIG. 9B) from one trace illustrates quantization—three separate regions of probability density occur due to single, double, and triple exciton quenching/de-quenching events occurring within the time resolution of the experiment (500 ms), denoted by integer multiple step heights.

A Solvatochromic Chaperone Sensor for Nitro Compounds

Figure 10:
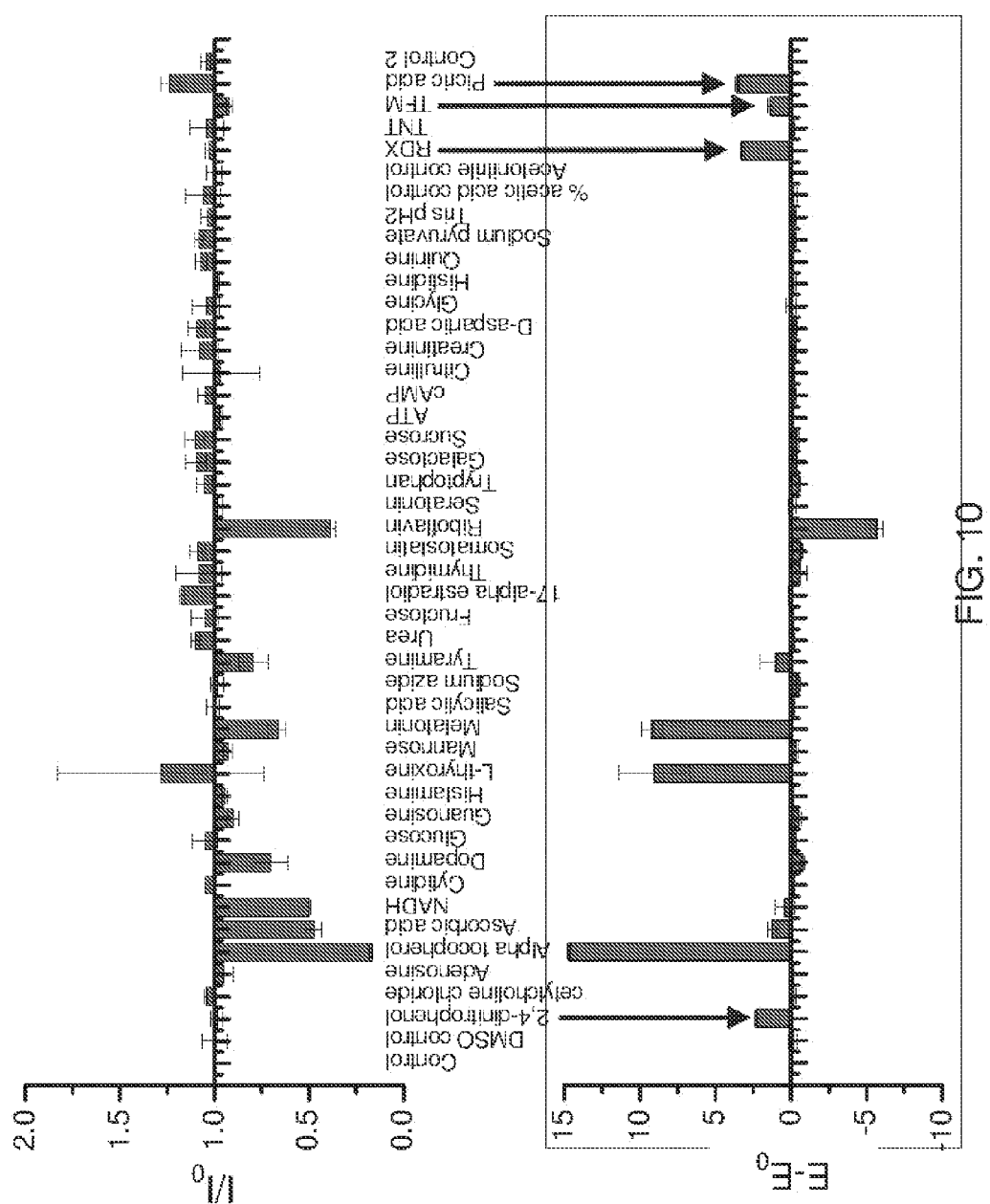
FIG. 10 presents graphs summarizing changes in the near-IR spectra of SWNTs exposed to various analytes.

Nanotubes solubilized by the peptide bombolitin II experienced wavelength shifts and slight concomitant intensity variation in response to four compounds containing nitro groups: RDX, picric acid, 2,4-dinitrophenol, and 4-nitro-3 (trifluoromethyl)phenol (TFM) (FIG. 10). Redox-active analytes induced intensity reductions, perhaps due to the bleaching interactions explained above. Some compounds which induce precipitous attenuation in the SWNT PL intensity also induced apparent wavelength shifts.

Figure 11:
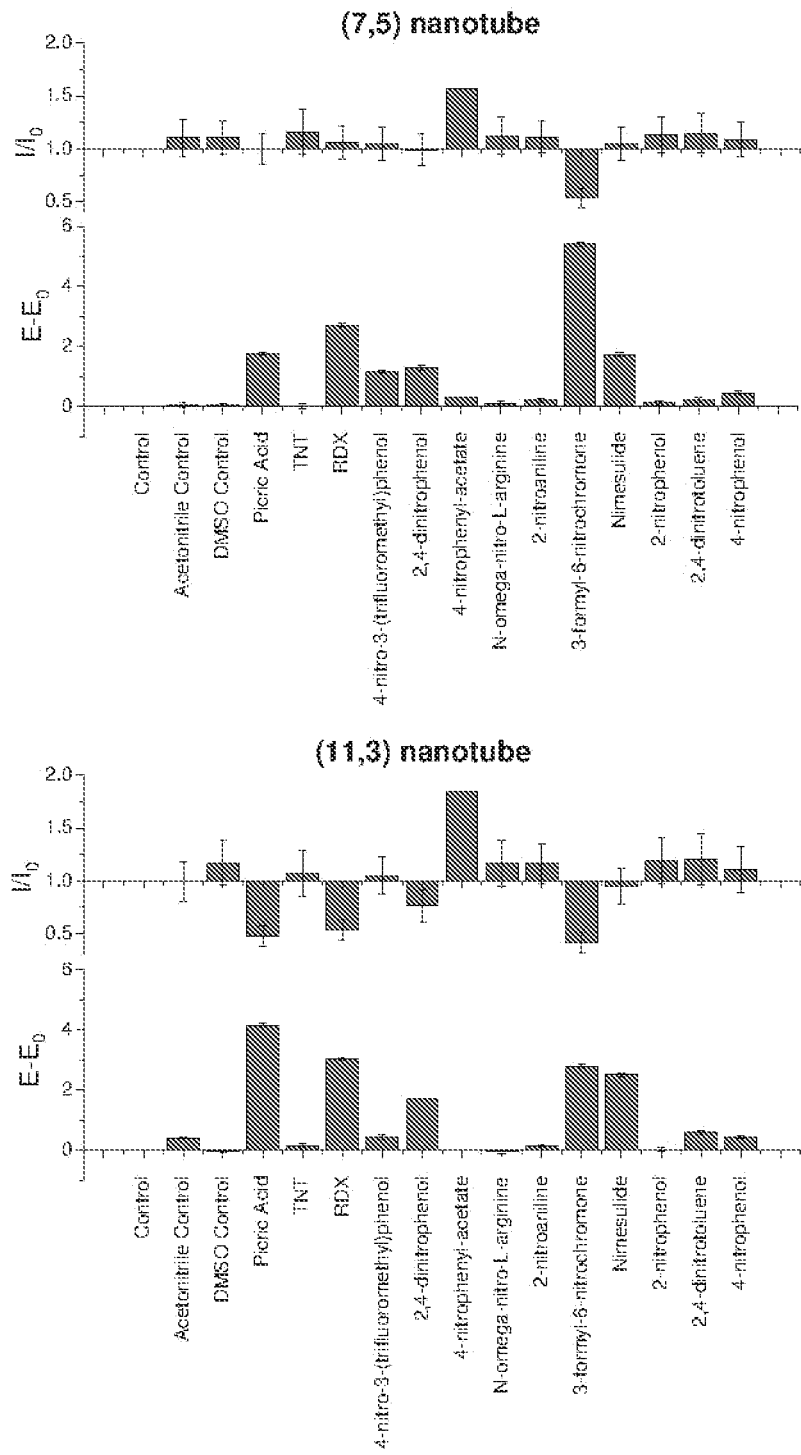
FIG. 11 presents graphs summarizing changes in the near-IR spectra of SWNTs exposed to various analytes.

Further investigation of nitro group-containing compounds with bombolitin II-SWNT found that 6 of 13 such compounds analyzed exhibited significant wavelength shifts (FIG. 11). It was also found that different (n,m) nanotube species exhibited different detection signatures, where the intensity and wavelength changes varied across SWNT species. This variation was demonstrated here for the (7,5) and (11,3) species, which possessed different diameters (0.829 nm vs. 1.014 nm), chiral angles (24.5° vs.) 11.74°), and optical bandgaps (1.211 eV vs. 1.036 eV). Principal components analysis (PCA) performed on the detection data, from eight different SWNT (n,m) species, confirmed unique signatures of the 6 analytes, denoted by their segregation into separate regions of the plot (FIG. 12), allowing identification of the analytes by their responses. The analysis was conducted by compiling all eight nanotubes' intensity change and wavelength shifting data for each analyte. The first three principal component scores, which account for a total of 99.5% of the total data variance, are shown. Table 7.1 contains the loadings for the first three principal components listed by input variable. All SWNT responses resulted from ring-structured compounds containing nitro groups. (FIG. 13).

TABLE 7.1

Loadings for the first three principal components listed by input variable.

| Input | Variable | PC1 | PC2 | PC3 |
|---|---|---|---|---|
| (8, 3) | Intensity | 0.0247 | 0.022 | −0.0049 |
| (6, 5) | Intensity | 0.0133 | 0.017 | −0.001 |
| (7, 5) | Intensity | 0.0197 | 0.0257 | 0.009 |
| (10, 2) | Intensity | 0.0176 | 0.0247 | −0.0397 |
| (8, 4) | Intensity | 0.0212 | 0.0163 | −0.0128 |
| (7, 6) | Intensity | 0.0245 | 0.0262 | −0.0323 |
| (8, 6) | Intensity | 0.0197 | −0.0033 | 0.0104 |
| (11, 3) | Intensity | 0.0346 | −0.0649 | 0.0105 |
| (8, 3) | Wavelength | −0.2348 | 0.0212 | −0.0073 |
| (6, 5) | Wavelength | −0.0851 | 0.2712 | −0.1581 |
| (7, 5) | Wavelength | −0.1972 | 0.0048 | −0.6714 |
| (10, 2) | Wavelength | −0.4291 | −0.0853 | 0.4189 |
| (8, 4) | Wavelength | −0.3753 | 0.0957 | 0.4816 |
| (7, 6) | Wavelength | −0.6703 | −0.4663 | −0.2561 |
| (8, 6) | Wavelength | −0.3095 | 0.6836 | −0.1913 |
| (11, 3) | Wavelength | −0.1567 | 0.4664 | 0.1071 |

The PCA inputs consist of the intensity and wavelength changes for eight SWNT species.

RDX Detection

The bombolitin-SWNT response to RDX was dependent on the peptide sequence. Aqueous solutions of peptide-stabilized SWNT were made with three of four members of the bombolitin family. All were amphiphilic, helical, 17-residue peptides isolated from bumblebee venom (See methods for sequences). Bombolitins II, III, and IV made highly NIR photoluminescent, stable solutions via probe-tip sonication in the presence of SWNT (FIGS. 14A-14C). The NIR spectra of the solubilized nanotubes showed variations in relative initial emission intensities and wavelengths of the PL maxima of the (n,m) SWNT species present in the sample. Upon introduction of 90 uM RDX, the photoluminescence peaks of bombolitins II and III underwent distinct red-shifts of up to 13 meV, with the magnitude dependent on the (n,m) species (FIGS. 14A-14B). Circular dichroism (CD) measurements conducted on the peptides in the absence of nanotubes showed similar spectra for bombolitins II and III, but the bombolitin IV spectrum differed, more closely resembling the classical alpha helical spectrum (FIGS. 14D-14F). Upon introduction of RDX, the bombolitin II and III spectra exhibited a distinct blue shift of their 206 nm peak and significant increase in the negative ellipticity. This data suggested a specific binding of RDX to the bombolitin II and III peptides, inducing a conformational change upon binding.

Figure 15:
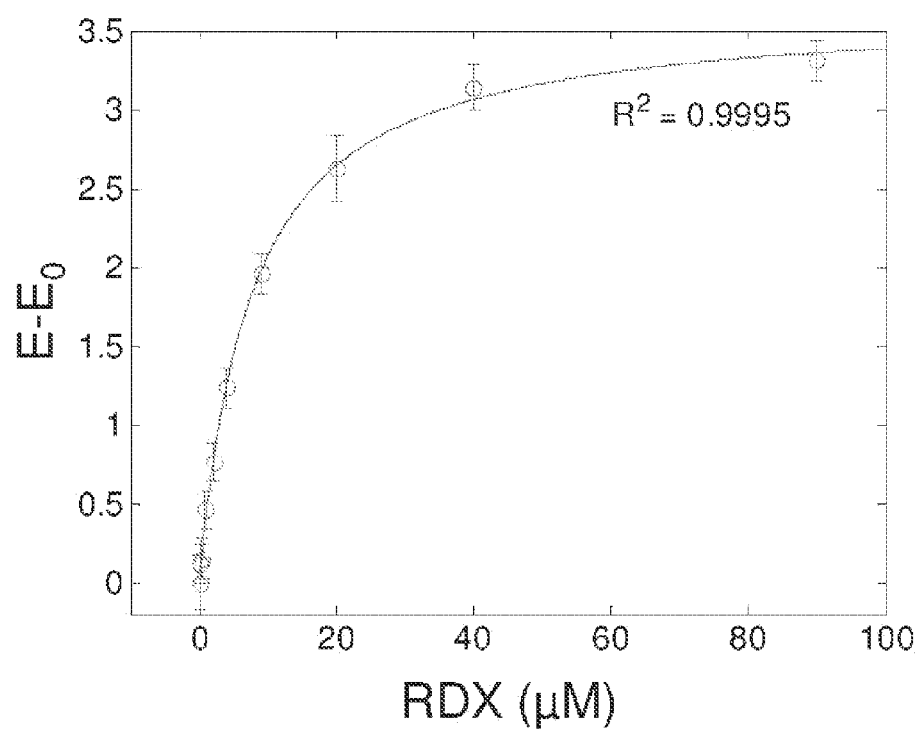
FIG. 15 is a graph illustrating the extent of wavelength shifting of a bombolitin II-solubilized SWNT in the prescence of varying amounts of RDX.

The wavelength shifting of bombolitin II-solubilized SWNT exhibited concentration dependence which fit well to a first-order Langmuir adsorption isotherm (FIG. 15), implying that the transition was reversible. The bombolitin II peptide was found to exhibit low affinity to SWNT, as it could be dialyzed away, causing aggregation of the nanotubes, evident from PL quenching in FIG. 16. Not wishing to be bound by any particular theory, this behavior suggests that the nanotube reports the conformation of the largely freely-suspended peptide. The nanotube, although solubilized by the peptide, acts as a "chaperone sensor," which indirectly detects the binding event by transducing changes to the native conformation of the bombolitin.

Figure 14:
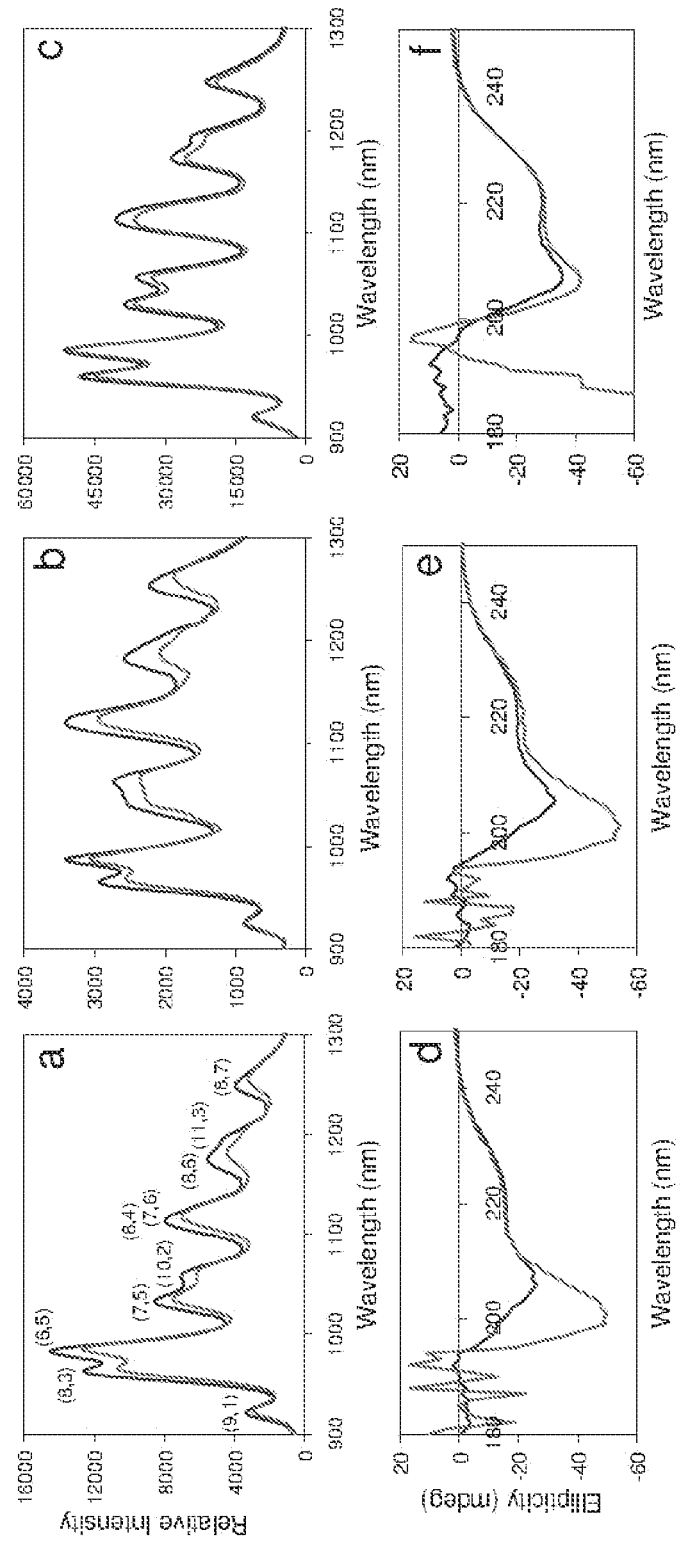
FIGS. 14A-14C are NIR spectra of SWNT-bombolitin preparations.
FIGS. 14D-14F are circular dichroism spectra of the same.
Figure 17:
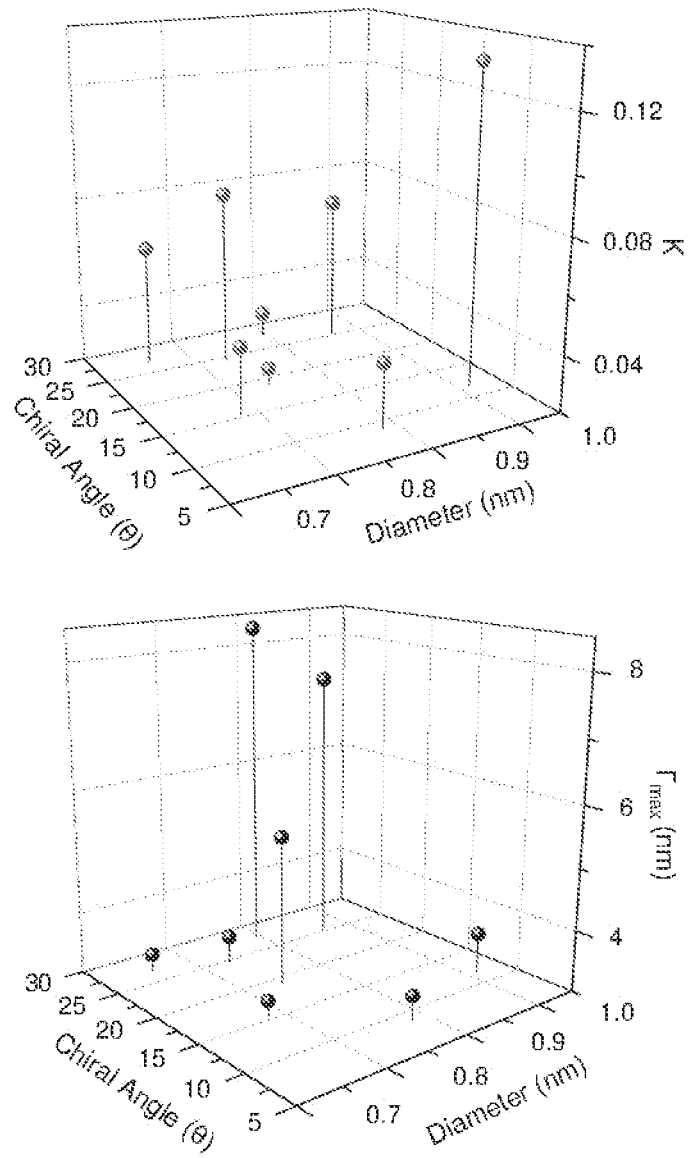
FIG. 17 presents graphs relating binding constant (top) or maximum wavelength shift (bottom) with diameter and chiral angle.

As seen in FIG. 14, different nanotube species did not respond equally to RDX-induced conformational changes of the peptide. Certain (n,m) species were more sensitive to RDX interrogation, and others exhibited a greater total degree of wavelength shifting. The Langmuir equilibrium constant, K, of RDX binding varied by nanotube species. The highest K's found were above 0.12 µM, on the order of the $K_d$ of a typical high affinity peptide binding interaction (0.11 µM for a VEGF-binding peptide). The maximum wavelength shift ($\Gamma_{max}$), exhibited a different dependence on SWNT species (FIG. 17). The $\Gamma_{max}$ was found to reach a maximum when the SWNT species diameter and chiral angle are greatest. Such a relationship would follow if the bombolitin II, in its RDX-bound conformation exhibited poorer stabilization of the larger, more chiral nanotubes as compared to the smaller SWNT with lower chiral angles.

Figure 18:
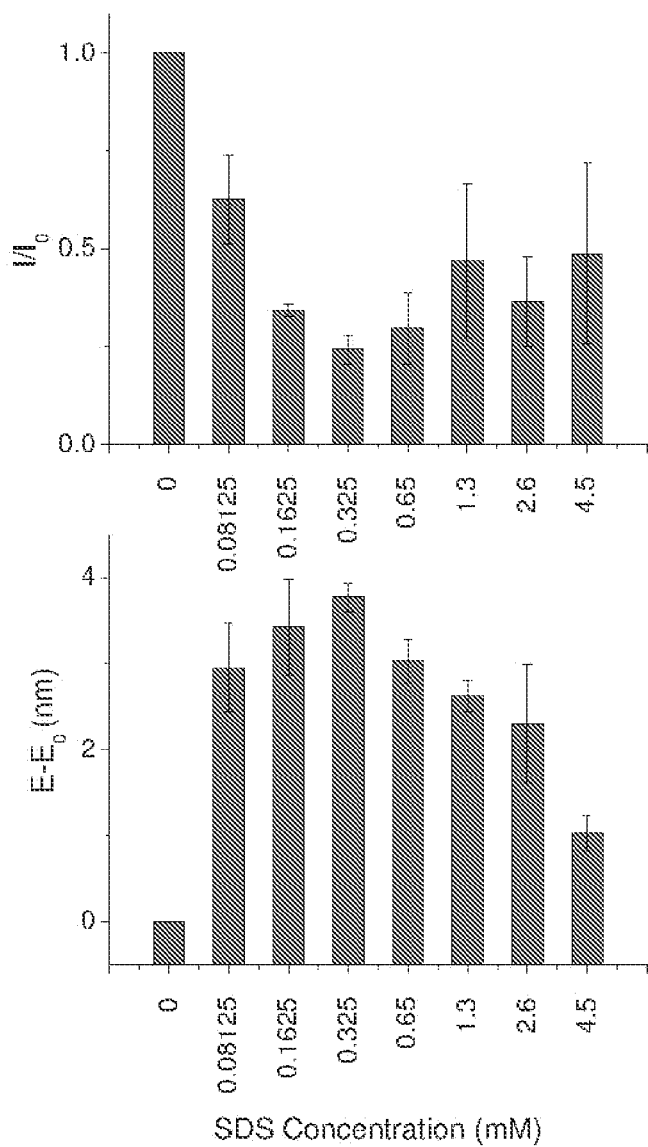
FIG. 18 presents graphs that summarize spectral changes in bombolitin II-SWNT preparations in the presence of varying amounts of SDS.

The native conformation of the bombolitin II peptide in aqueous solution appeared to be largely unordered although some structure may have existed given the broad shoulder at 222 nm in the circular dichroism spectrum. Upon introduction of low concentrations of sodium dodecyl sulfate (SDS) to the peptide, β-aggregates form in solution. At concentrations near the critical micelle concentration (CMC), the peptide suspended in solution and adopted an α-helical conformation. This was demonstrated in the presence of the nanotube by addition of SDS to the bombolitin II-SWNT suspension (FIG. 18). Upon addition of 80 uM SDS to 45 µM peptide, the nanotube PL fell and shifted, and precipitates were visible. The SWNT intensity increased and blue-shifted at higher SDS concentrations. These experiments demonstrated the high sensitivity of nanotube PL to the bombolitin II conformation.

Single-Molecule Analyte Detection

Figure 19:
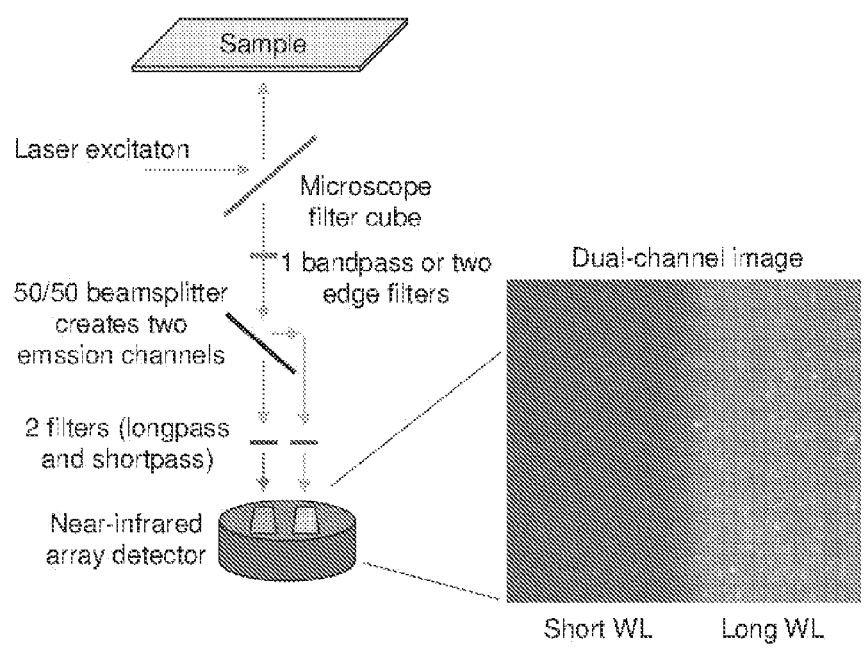
FIG. 19 schematically depicts a system for single molecule analyte detection, and a microscope image demonstrating such detection.
Figure 20:
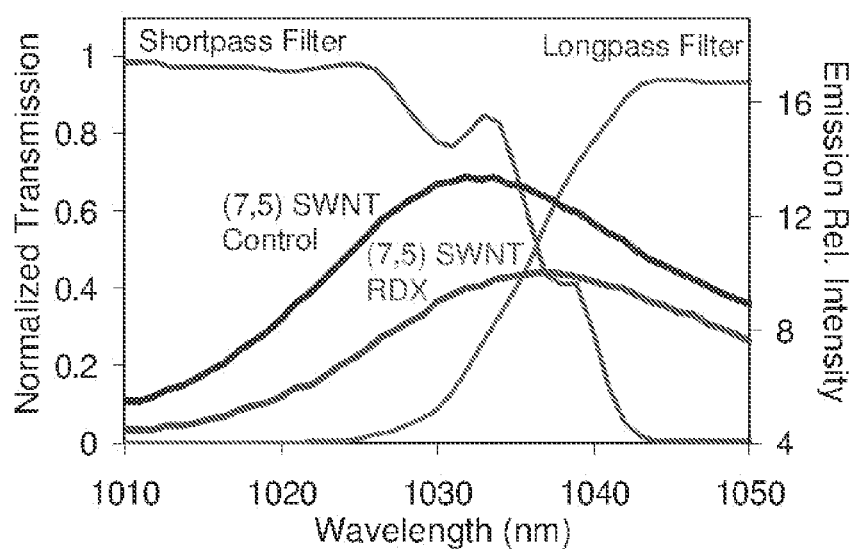
FIG. 20 is a graph showing NIR spectral properties of materials used in single molecule analyte detection.

A near-infrared dual-channel microscope for imaging spectral shifts of nanotube PL was also constructed (FIG. 19). The microscope allowed spectroscopic information to be elucidated by splitting the image into two channels which are adjacent in wavelength. The light from one nanotube emission band was split into two beams. The light from both beams was treated with filters to spectroscopically isolate one emission peak, and then to permit only half of the peak's emission to appear in each channel. One channel on the same near-infrared detector array showed the long wavelength half of the peak, and the other contained the short wavelength half. The filters used were designed to measure the (7,5) nanotube. The 50% cut-off/cut-on of the edge filters were at 1030 nm. A 1000 longpass and 1100 nm shortpass filter were placed in the emission beam before splitting to isolate the (7,5) peak and block all other SWNT emission (FIG. 20).

This microscope detected minute SWNT spectral shifts which signified RDX binding to bombolitin II. Nanotubes were immobilized on a glass surface and imaged in the presence of 8 µM of the peptide in Tris buffer. The emission of each PL spot in the detector was binned in a 2×2 pixel area and measured in each channel over the course of a 2000-second movie taken at one frame per second. The RDX was introduced to the peptide solution above the immobilized nanotubes during the course of the movie. The traces were fit by a hidden Markov algorithm. (See Jin, H., Heller, D. A., Kim, J. H. & Strano, M. S. Stochastic Analysis of Stepwise Fluorescence Quenching Reactions on Single-Walled Carbon Nanotubes: Single Molecule Sensors. *Nano Letters* 8, (2008) 4299-4304, which is incorporated herein by reference in its entirety).

The long-wavelength nanotube emission responded by exhibiting distinct upward steps, while the short-wavelength SWNT emission exhibited downward steps. This anti-correlated behavior denoted red-shifting of the surface-bound nanotubes' PL. Correlated downward and upward steps denoted excitonic quenching and de-quenching. An example pair of traces from the two channels (FIG. 21A-21B) exhibited stepwise correlated and anti-correlated behavior after introduction of RDX. A histogram of correlated steps (FIG. 21C) illustrates quantization of quenching/de-quenching step heights. Both channels are expected to exhibit greater downward step behavior than upwards, denoting stepwise attenuation which is visible in the spectral response of RDX. A histogram plotting only anti-correlated steps (FIG. 21D) demonstrates quantization of shifting steps. Downward steps (positive numbers on the graph) are more prevalent in the short wavelength channel and upward steps (negative numbers) are more prevalent in the long wavelength channel. This behavior is expected, as it denotes PL red-shifting. Quantization of step heights is also present, confirming the presence of single-molecule shifts. Histograms of correlated (FIG. 21E) and anti-correlated (FIG. 21F) steps from control time traces contain a wide distribution of step heights, no quantization, and similar behavior in long and short wavelength channels, signifying a lack of quantized shifting behavior.

Figure 21:
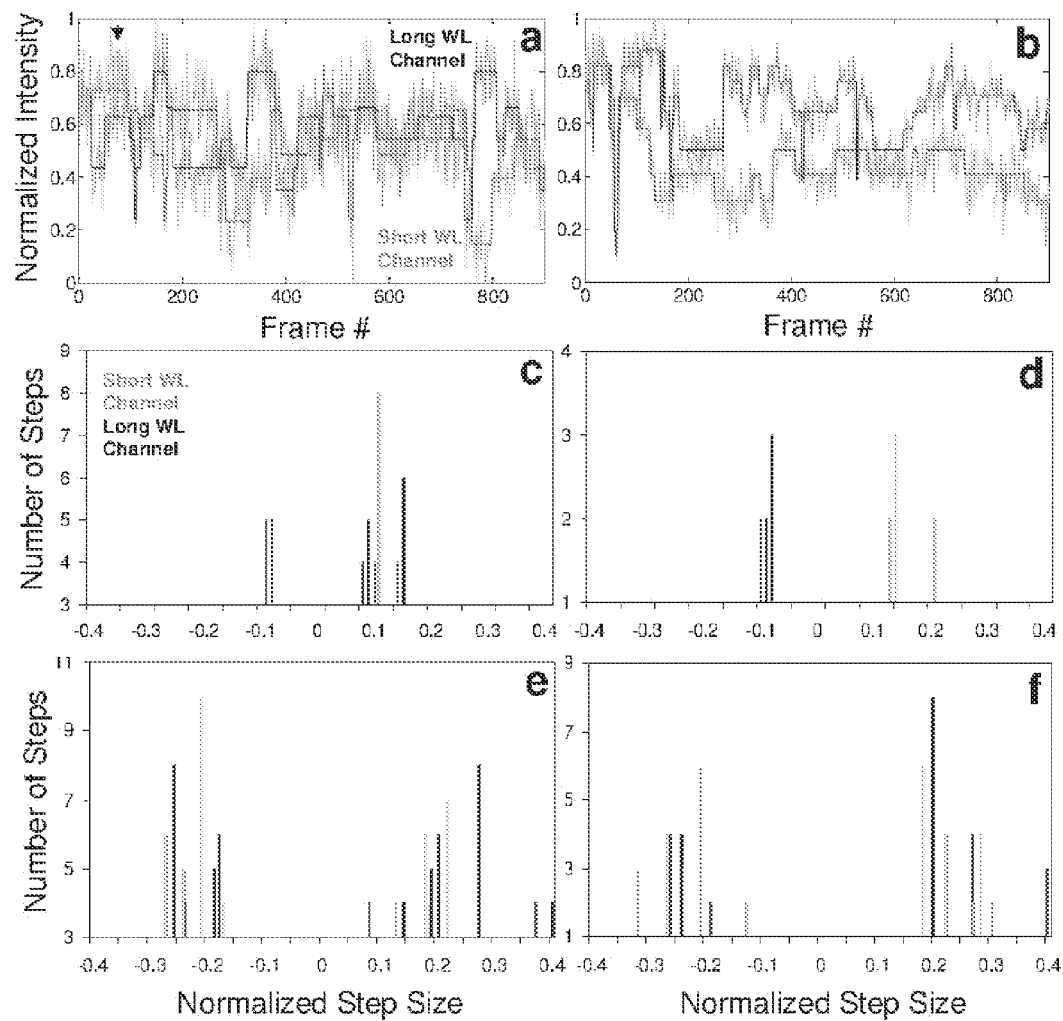
FIGS 21E-21F are histograms depicting correlated and anticorrelated steps in control time traces, respectively.

Such stepwise changes suggested that single molecules of RDX binding to the peptide, as well as un-binding events, would be detectable by this method. Later un-correlated events due to quenching steps present in the long WL channel may have been due to the RDX-induced quenching of the emission which has already shifted away from the short WL channel and therefore exhibits low relative intensity in that channel, as shown by plotting the absorption spectra of the edgepass filters with the SWNT PL spectra before and after RDX addition (FIG. 21).

Experimental Methods

Preparation of SWNT Suspensions

Single-walled carbon nanotubes synthesized by the HiPCO method (Unidym) were suspended in a 2:1 mass ratio of Bombolitin to SWNT in 20 mM Tris and 100 mM NaCl (henceforth known as Tris buffer) using a ⅛th inch probe-tip sonicator (Vibra-Cell) at 10 W for 10 min. The resulting bombolitin-SWNT solution was centrifuged twice for 90 minutes at 16,300 g and the pellet removed each time. Bombolitin sequences used were bombolitin I: IKITTMLAK-LGKVLAHV (SEQ ID NO: 8), bombolitin II: SKITDILAK-LGKVLAHV (SEQ ID NO: 9), bombolitin III: IKIMDILAKLGKVLAHV (SEQ ID NO: 6), and bombolitin IV: INIKDILAKLVKVLGHV (SEQ ID NO: 7), (AnaSpec).

DNA-encapsulated SWNT was prepared by sonicating nanotubes (Nano-C or Unidym) in the presence of $d(GT)_{15}$ DNA (SEQ ID NO: 10) (IDT) in a 2:1 DNA:SWNT ratio in a solution of 0.1 M NaCl using the same sonication and centrifugation steps as above.

DNA-encapsulated SWNT was prepared by sonicating nanotubes (Nano-C or Unidym) in the presence of $d(GT)_{15}$ DNA (IDT) in a 2:1 DNA:SWNT ratio in a solution of 0.1 M NaCl using the same sonication and centrifugation steps as above.

Suspensions of SWNT encapsulated by PVA were prepared by first sonicating nanotubes in the presence of a 2% aqueous solution of sodium cholate for 20 minutes in a 750 W cup-horn sonicator (Vibra-Cell) at 90% amplitude. Suspensions were ultra-centrifuged for 4 h at 100,000 g and the pellet removed. The resulting suspension was stirred with 2% PVA (31,000-50,000 MW) overnight at 70° C. then dialyzed against 2 L of water for 24 h.

Preparation of RDX Solutions

A mixture of 10:1 weight ratio sand to RDX was added to acetonitrile and filtered through a 0.45 micron syringe filter. The resulting solution was precipitated in excess water and filtered using a 0.22 micron millipore filter using a vacuum flask. The filtered solid RDX was dissolved in acetonitrile as a stock solution. An aqueous solution was prepared by adding 1% stock solution in acetonitrile to water and centrifuged twice at 16,300 g for 5 minutes and the pellet removed each time.

Analyte Screening and Spectroscopy

Analyte screening was conducted in a 96 well plate containing either a bombolitin-SWNT solution of 8 uM peptide or a PVA-SWNT solution of 2 mg/L SWNT. The SWNT solutions were interrogated by the analytes added separately to each well. The nanotubes and analytes were incubated for 1 hour. Near-infrared photoluminescence spectra were obtained using 785 nm excitation and an Acton SP-150 spectrograph coupled to a Princeton Instruments OMA V InGaAs detector. Bombolitin-SWNT prepared alternately with peptides bombolitin II, III, and IV and mixed with 90 uM RDX in 1% acetonitrile solution. The near-infrared photoluminescence spectra were obtained 1 h after mixing.

Circular Dichroism

Circular Dichroism measurements were obtained using an Aviv Model 202 Circular Dichroism Spectrometer in a 1 mm pathlength strain-free cuvette. Bombolitin solutions of 0.275 mM in Tris buffer were measured before and after the addition of 9 nM RDX solution in 1% acetonitrile while keeping the bombolitin concentration constant.

SDS Addition Experiment

Bombolitin-SWNT solutions of 44 µM in Tris buffer were mixed with varying concentrations of SDS in water. Near-infrared photolumincescence spectra were acquired 1 h after mixing.

Microscopy of SWNT Solvatochromic Shifts

As-produced Bombolitin II-SWNT was incubated on a glass coverslip-bottom petri dish (MatTek Corporation) for 30 minutes and subsequently rinsed 3× with Tris buffer. The glass surface was then covered with 100 µL Tris buffer including 8 µM of bombolitin II peptide. An aliquot of 100 µL of 180 µM RDX suspended in Tris buffer was added to the petri dish 100 seconds after data collection began. The glass surface was imaged by exciting with a 658 nm laser on a Zeiss Axio Observer D1 microscope whose light path was modified by the optical setup illustrated in FIG. 15 after the light passed through a 5 mm slit. Movies were collected at 1 frame/second. The movies were processed by averaging the signal over a spot size of 2×2 pixels and plotting the resulting intensity versus time. A SWNT photoluminescence spot on the left channel correlates to the one on the right channel by having the same y-axis value and being 160 pixels apart in the x-axis. Time traces of the average intensity of the 2×2 pixel spots were normalized to their initial values.

FIGURE DESCRIPTIONS

FIG. 6: Analyte screening results against PVA-solubilized SWNT (top), $d(GT)_{15}$-encapsulated SWNT (middle), and d(AT)$_{15}$-encapsulated SWNT (bottom). Intensity changes of the (7,5) nanotube species relative to the control (I/I$_0$), as well as the wavelength shift in nanometers relative to the control (E-E$_0$) are shown for each analyte. (All error bars indicate one standard deviation.)

FIG. 7: (a) Photoluminescence intensity and wavelength responses of the (7,5) SWNT species, encapsulated by d (AT)$_{1-5}$ (SEQ ID NO: 11), to nitro group compounds. (b) Carbon nanotube Fermi levels in V plotted against SWNT E11 transition energies. The reduction potentials of several analytes are shown (horizontal lines); most are higher than the SWNT Fermi level, portending electron withdrawal from the nanotube. (c) The reduction potentials of three nitroaryl compounds compared to the SWNT Fermi level. The reduction potentials of TNT and 2,4-dinitrotoluene suggest they will oxidize several SWNT species while 2-nitroanaline will not.

Figure 8:
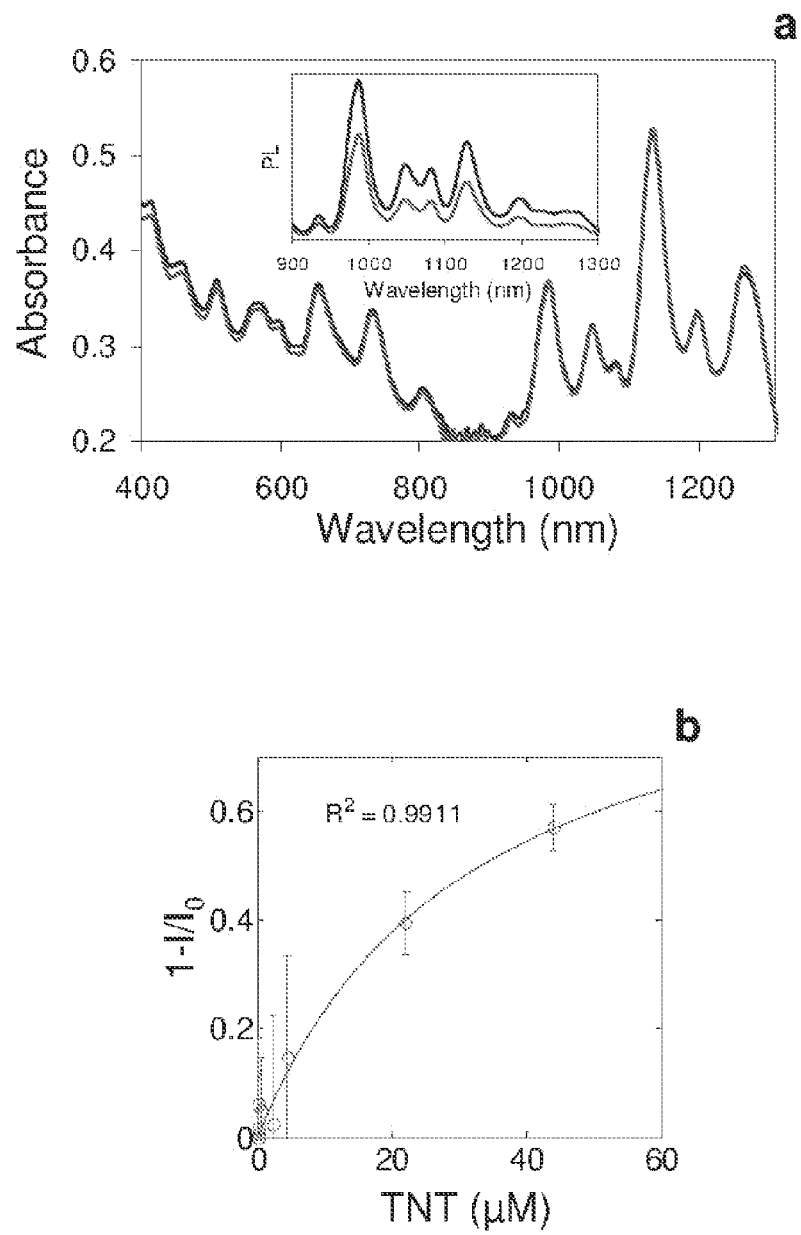
FIG. 8A shows spectra of $d(AT)_{15}$-SWNT interacting with TNT.
FIG. 8B is a graph demonstrating PL quenching of SWNT by TNT.

FIG. 8: (a) Absorption spectra of d(AT)15-SWNT before (blue) and after (red) introduction of 44 µM TNT. Inset: PL spectra under same conditions. (b) Langmuir adsorption isotherm of TNT binding to the d(AT)15-encapsulated (8,7) SWNT species.

Figure 9:
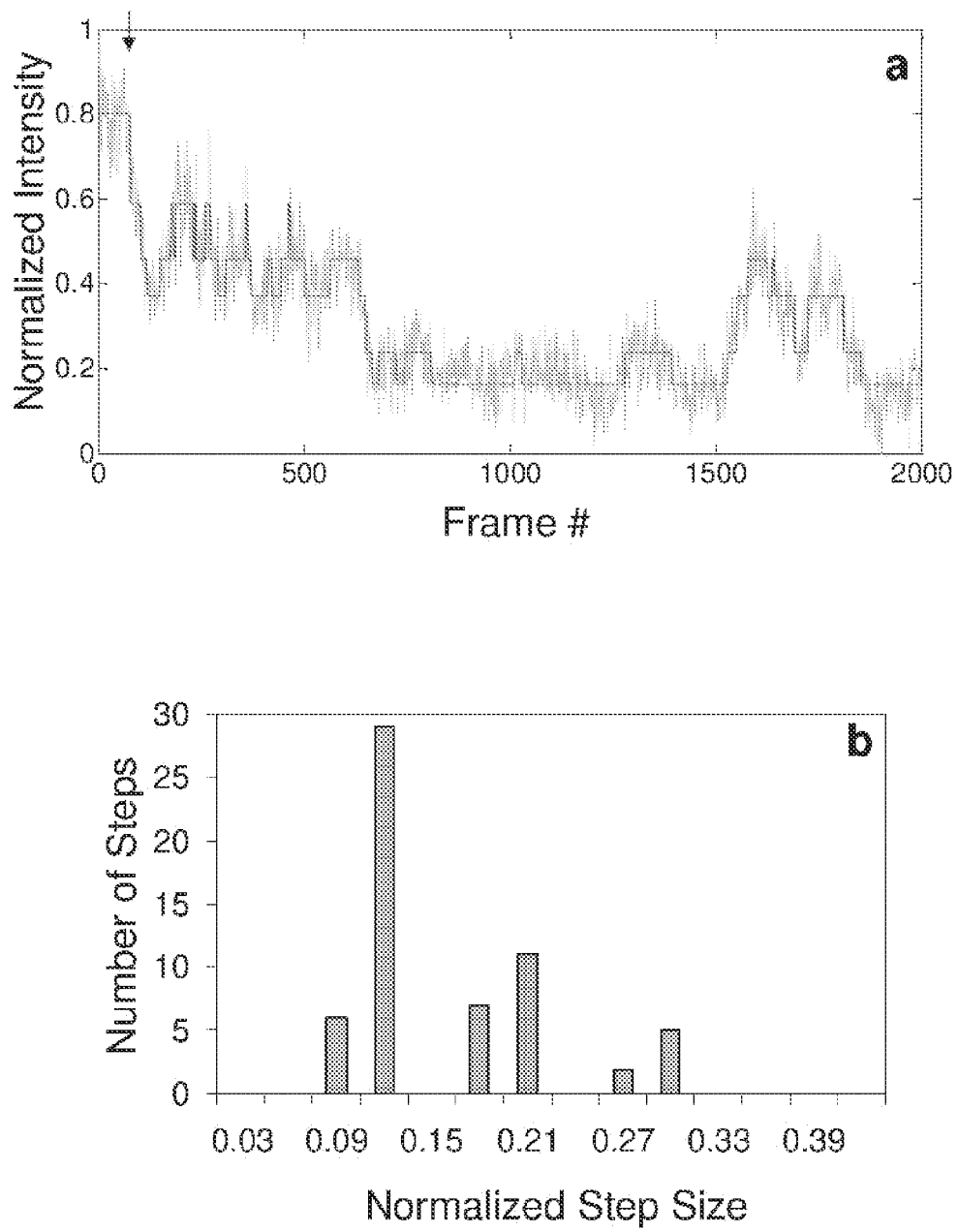
FIG. 9A is a time-trace of single-molecule detection of TNT by real-time PL measurement of $d(AT)_{15}$-SWNT adhered to a glass surface.
FIG. 9B is a histogram of step heights from one such trace.

FIG. 9 (a) Single-molecule TNT detection by d(AT)15-SWNT complexes bound to glass. The trace shows the PL of a single complex acquired under 658 nm excitation. TNT (220 nM) was added at frame 100 (red arrow); one frame was acquired every 500 ms. Intensity fluctuations were fit by a hidden Markov model (red). (b) A histogram of fitted intensity fluctuations from a single trace shows quantization into single, double, and triple steps.

FIG. 10: Bombolitin II-solubilized SWNT exhibits wavelength shifts and minimal intensity changes upon exposure to certain nitro compounds (blue arrows).

FIG. 11: Bombolitin II-solubilized nanotube responses to nitro compound responses. Intensity and wavelength responses of the (7,5) nanotube (top) and the responses of the (11,3) nanotube (bottom) differ. (Error bars indicate one standard deviation.)

Figure 12:
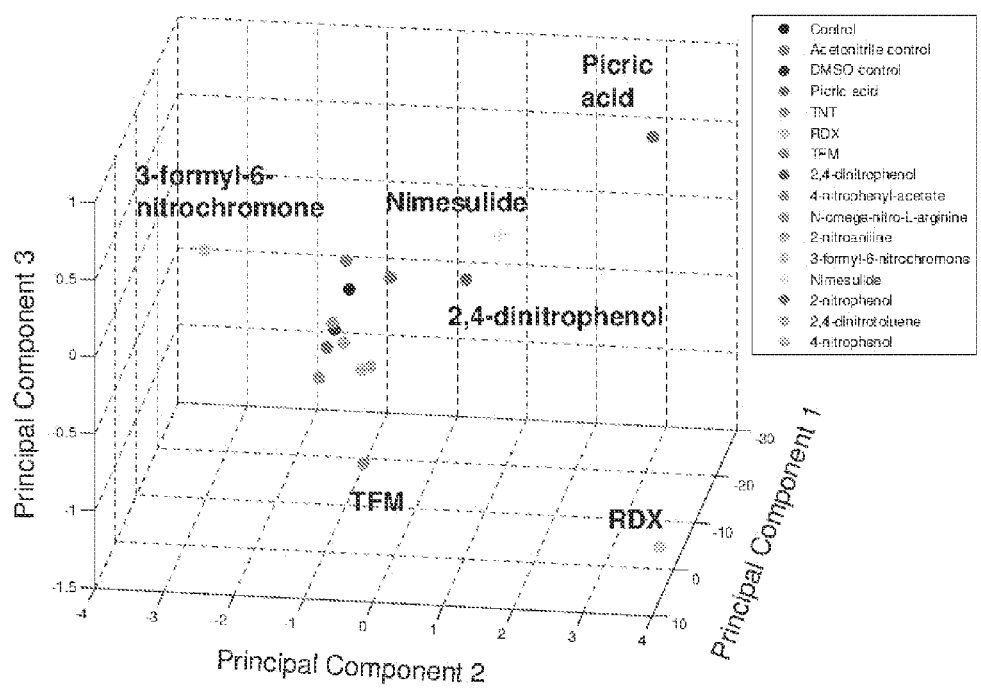
FIG. 12 illustrates prinicipal components analysis (PCA) on detection data from eight different SWNT (n, m) species and six different analytes.
Figure 13:
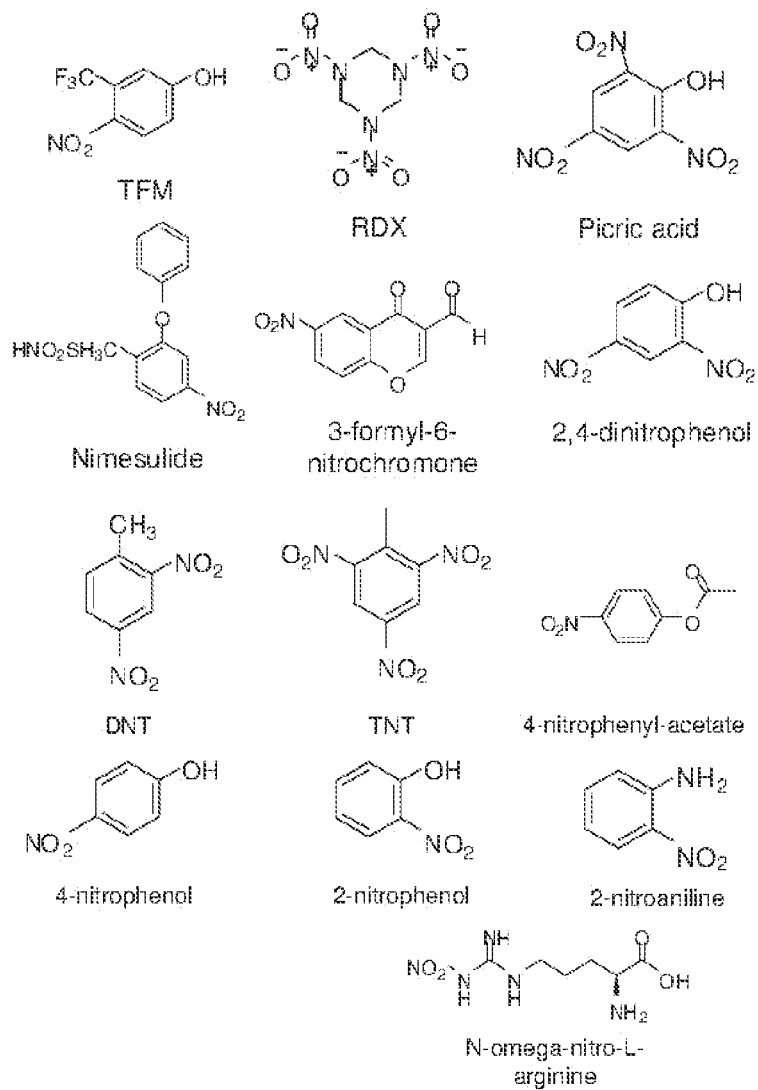
FIG. 13 illustrates structures of a variety of nitro-containing analytes.

FIG. 12: Principal components analysis plot using the intensity and wavelength spectral data from bombolitin II-solubilized SWNT responses to the 13 nitro compounds from FIG. 11. The first three principal component scores are plotted on three axes; data from eight nanotube species was used.

FIG. 13: Nitro group-containing compounds exposed to bombolitin II-SWNT.

FIG. 14: Photoluminescence spectra of peptide-suspended nanotubes before (blue) and after (red) addition of 90 µM RDX. (a) Spectra of nanotubes suspended by bombolitin II (b) bombolitin III (c) bombolitin IV. Circular dichroism spectra of the same peptides in the absence of nanotubes before (blue) and after (red) addition of RDX. (d) CD spectrum of bombolitin II, (e) bombolitin III, (f) bombolitin IV.

Figure 16:
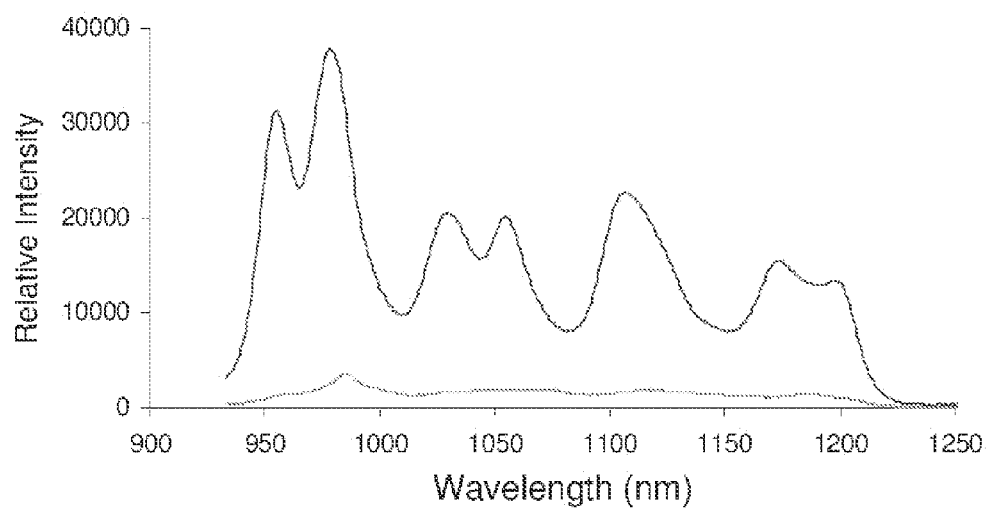
FIG. 16 presents NIR spectra of bombolitin II-solubilized SWNTs before and after dialysis.

FIG. 16: Center wavelength of the (11,3) nanotube peak of bombolitin II-solubilized SWNT plotted versus RDX concentration (red circles). The data is fit to a first-order Langmuir adsorption isotherm (blue curve).

FIG. 17: Photoluminescence spectrum of bombolitin II-solubilized SWNT before (blue) and after (pink) dialysis using a 20,000 MWCO membrane through which the free peptide, but not the nanotubes, can pass. Quenching of the PL denotes nanotube aggregation in the absence of other external factors.

FIG. 18: Langmuir isotherm parameters of individual SWNT species from RDX-induced shifting of bombolitin II-encapsulated SWNT. Langmuir equilibrium constant (top) and maximum wavelength shift (bottom) of eight nanotube species' responses, plotted versus nanotube chiral angle and diameter.

FIG. 19: Bombolitin II-SWNT photoluminescence changes upon addition of SDS. Variations in the intensity (top) and wavelength (bottom) of the (6,5) species after one hour of incubation. (Error bars indicate one standard deviation.)

FIG. 10: Near-infrared dual-channel microscope. Light leaving the sample passes through a bandpass or two edgepass filters to spectroscopically isolate one fluorescence band. This light reaches a 50/50 beamsplitter which creates two equal beam pathways. The resulting beams pass through edgepass filters (a longpass for one and a shortpass for the other) with a 50% cut-off or cut-on at the same wavelength. The beams are captured by two different regions of a near-infrared array detector. The image shows the same location of the microscope field on both the Short WL and Long WL channels, but the spectral region is different. The two red boxes encircle the same nanotube in both channels.

FIG. 20: Absorption curves of edgepass filters used in the dual-channel microscope measurements, plotted with the (7,5) SWNT photoluminescence curves before (blue) and after (red) introduction of 90 µM RDX.

FIG. 21: (a-b) Time traces of the intensity of a nanotube's photoluminescence in the short WL (green) and long WL (blue) channels fit by a hidden Markov algorithm. Addition of 9 µM RDX occurred at time=100 s (red arrow). (c) Histogram of correlated step heights and (d) anti-correlated step heights collected from 13 RDX response time traces. (e) Histograms from 13 control time traces of correlated steps and (f) anti-correlated steps.

Example 3

This example describes experiments in which a pair of single-walled carbon nanotubes provide at least four modes that can be modulated to uniquely fingerprint agents by the degree to which they alter either the emission band intensity or wavelength. The identification method was validated in vitro by demonstrating detection of six genotoxic analytes, including chemotherapeutic drugs and reactive oxygen species (ROS), which are spectroscopically differentiated into four distinct classes. Also demonstrated is the single-molecule sensitivity in detecting hydrogen peroxide, one of the most common genotoxins. Finally, the sensing and fingerprinting methods of these analytes is employed in real time within live 3T3 cells, demonstrating the first multiplexed optical detection from a nanoscale biosensor and the first label-free tool to optically discriminate between genotoxins.

Carbon nanotubes can be broadly functionalized and their 1D electronic structure is sensitive to molecular adsorption. The mechanisms of signal transduction can include charge transfer interactions, which alter the nanotubes' Fermi level, and solvatochromic shifts, which modify nanotubes' intrinsic photoluminescence signatures. The existence of multiple photoluminescent SWNT species suggests untapped potential for multi-modality as variations in their responses can be exploited to discern molecular properties and identify analytes within a mixture. In this example, such a sensor is employed by measuring the differing responses of the (6,5) and (7,5) SWNT species. Chemotherapeutic alkylating agents and reactive oxygen species (ROS) were detected and identified via unique spectral responses generated by their interaction with DNA-encapsulated nanotubes.

Active alkylating drugs and ROS are important biological analytes which can be difficult to measure in vivo or in real time. Alkylating chemotherapeutic drugs from the nitrogen mustard and cis-platinum families are essential in treatments for multiple types of cancer. These drugs function by alkylating DNA, which leads to eventual strand breakage and results in apoptosis of mammalian cells. The agents can degrade in the body within a few hours, impeding their measurement in live cells and tissues. Standard techniques, such as immunoassays, gel electrophoresis, and NMR typically cannot be performed in live cells or require preparation steps which inhibit real-time measurement. Nucleic acid damage due to ROS interaction with DNA is widely suspected to have a role in oncogenesis and Alzheimer's disease. Hydrogen peroxide, produced by mitochondria, can react catalytically to form multiple ROS, including hydroxyl radicals, singlet oxygen, and the superoxide anion. These species, with half-lives between a nanosecond and a millisecond in solution, can form DNA adducts, crosslinks, and strand-breaks but are difficult to observe due to their short lifetimes. A label-free sensor which converts chemical information immediately into a near-infrared signal would be a promising tool for studying these challenging bioanalytes.

Figures 22A, 22B, 22C, 22D, 22E:
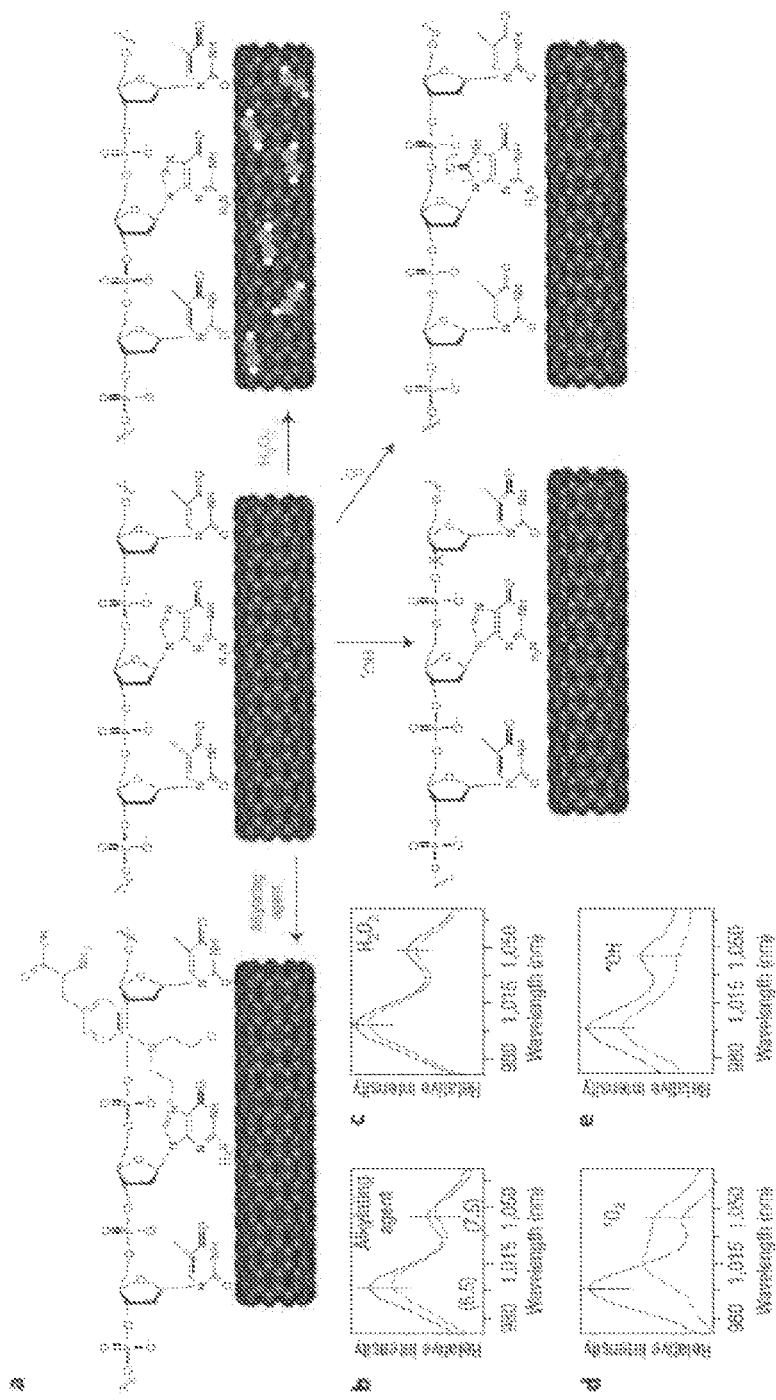
FIG. 22A outlines four reaction pathways which were measured via SWNT optical modulation.
FIGS. 22B-22E show NIR spectra that result from the four pathways.
Figure 26:
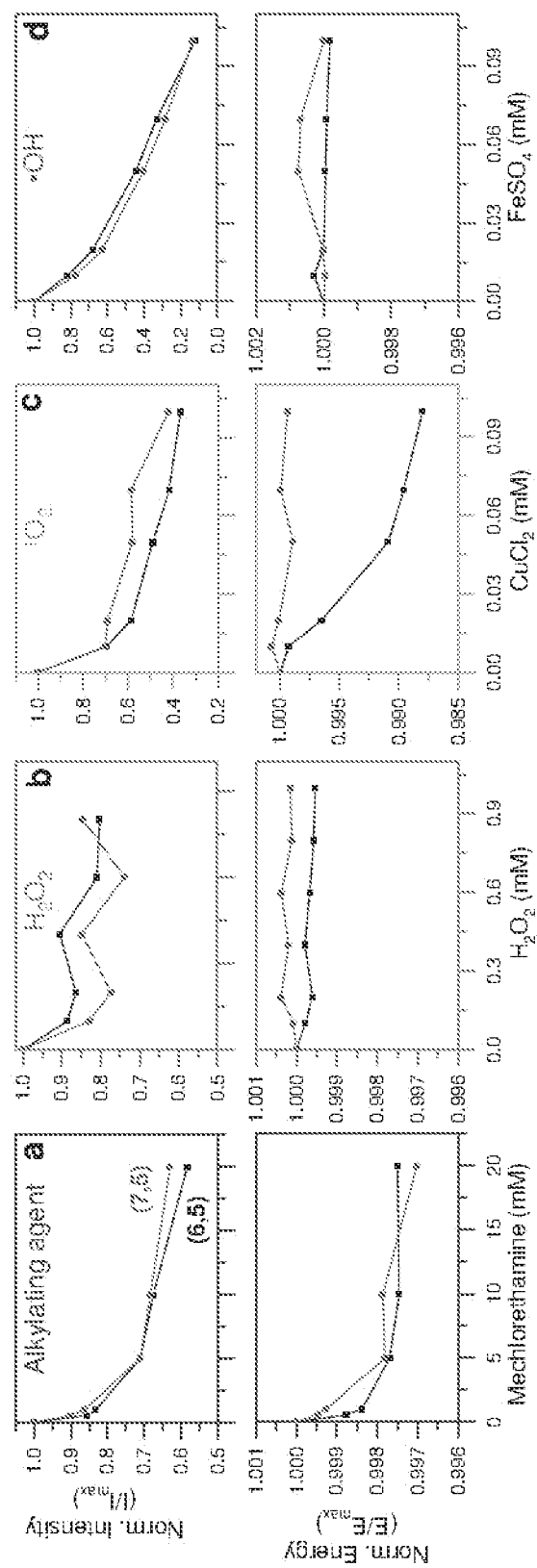
FIGS. 26A-26D are graphs summarizing spectral changes of DNA-SWNT complexes upon exposure to varying concentrations of DNA damaging agents.

FIG. 22A outlines four reaction pathways which were measured via SWNT optical modulation. In the first reaction, the $d(GT)_{15}$ oligonucleotide-bound nanotube (DNA-SWNT) was exposed to a chemotherapeutic alkylating agent (melphalan shown) which reacted with the guanine nucleobase. This resulted in a uniform red-shift in the photoluminescence bands of both (6,5) and (7,5) nanotubes (FIG. 22B). The second reaction shows direct adsorption of hydrogen peroxide with the nanotube which results in attenuation of both nanotubes' emission and a slight concomitant energy shift (FIG. 22C). Singlet oxygen, generated by exposing the nanotube complexes to $Cu^{2+}$ and $H_2O_2$, causes a pronounced red-shift of the (6,5) nanotube emission, but no corresponding shift in the (7,5) band (FIG. 22D). Finally, hydroxyl radicals, produced in the presence of SWNT by $Fe^{2+}$ and $H_2O_2$, damage the DNA backbone and attenuate both nanotubes' emission but preferentially affect the (7,5) emission, without energy shifts (FIG. 22E). These spectral changes can be monitored transiently, elucidating the dynamic behavior of each agent and the clear differences among them (FIGS. 22F-22I). The same trends are evident upon varying genotoxin concentration (FIG. 26).

Figure 27:
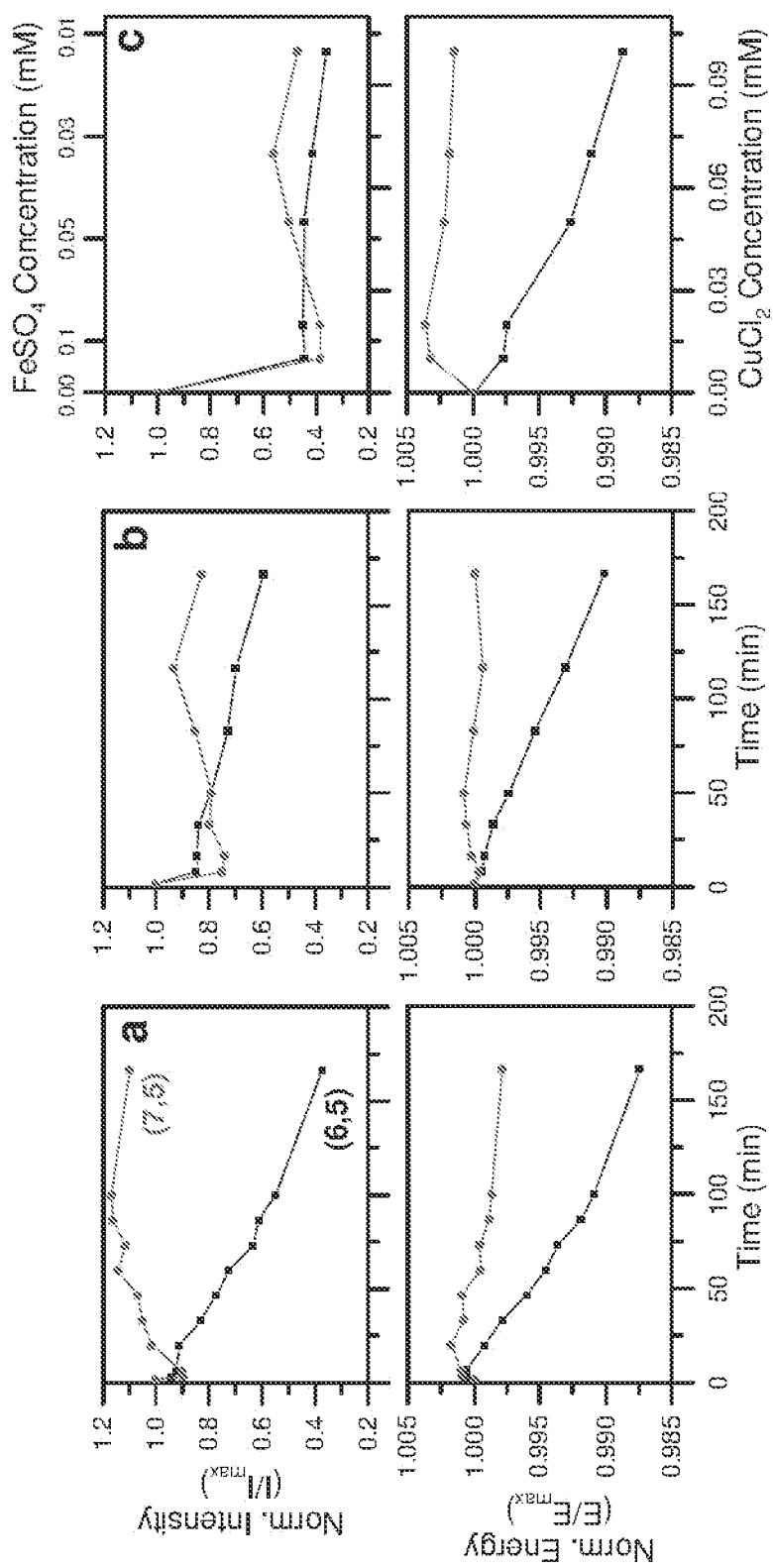
FIG. 27A-27C are graphs summarizing spectral changes of DNA-SWNT complexes over time (27A, 27B) or in the presence of varying concentrations of DNA damaging agents (27C).

Exposing DNA-SWNT to several analytes simultaneously can achieve signal multiplexing. Concomitant generation of hydroxyl radicals and singlet oxygen can elicit a precipitous initial intensity drop and pronounced (6,5) band intensity shifts, corresponding to the production of both analytes (FIG. 27). Subsequent analysis described below confirms multiplexed detection.

Figures 22F, 22G, 22H, 22I, 22J:
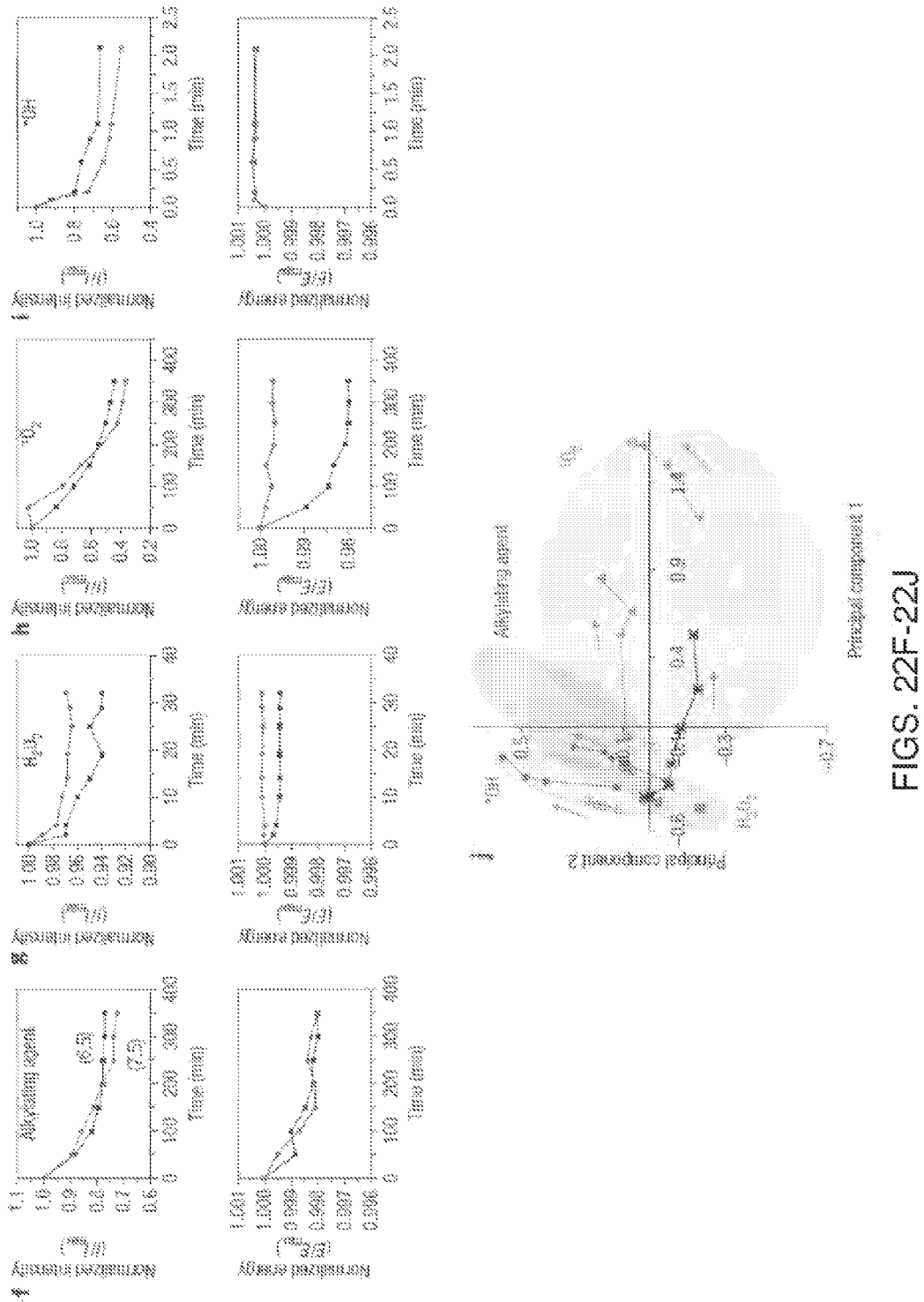
FIGS. 22F-22I summarize the spectral changes as a function of time.
FIG. 22J is a graph presenting results of principal components analysis of the spectral changes measured in FIGS. 22B-22I.

Principal components analysis (PCA) validated analyte fingerprinting. The subspace determined by the first two principal component scores of all transient and concentration-dependent (6,5) and (7,5) response data exhibited segregation by analyte (FIG. 22J). (PCA scores are listed in Supplementary Table 1.) This confirmed analyte identification based on the four signal transduction modes. Analysis of simultaneous reagent detection (from FIG. 27) verified multiplexed detection, as early time points cluster in the hydroxyl radical and $H_2O_2$ zones, while later points situated in the singlet oxygen region. The nature of all analyte responses were investigated as described below.

SUPPLEMENTARY TABLE S1

Principal components analysis scores for all reagents.

| | | Conc. (mM) or Time (min) | PC 1 | PC 2 | PC 3 | PC 4 |
|---|---|---|---|---|---|---|
| Concentration (mM) | Mechlorethamine | 1 | −0.3115 | −0.0642 | 0.0983 | −0.0605 |
| | | 5 | −0.181 | 0.1469 | 0.1418 | −0.074 |
| | | 10 | −0.1482 | 0.1752 | 0.1193 | −0.061 |
| | | 20 | −0.1131 | 0.2966 | 0.1573 | −0.0263 |
| | $H_2O_2$ | 0.2 | −0.4365 | −0.0335 | −0.037 | −0.104 |
| | | 0.6 | −0.4252 | 0.0201 | −0.0584 | −0.0776 |
| | | 0.8 | −0.4264 | −0.0428 | 0.0127 | −0.0196 |
| | | 1 | −0.4064 | 0.0167 | −0.0231 | −0.0225 |
| | Singlet oxygen | 0.02 | −0.0582 | 0.0894 | −0.0842 | 0.0442 |
| | | 0.05 | 0.5275 | 0.1143 | −0.0423 | −0.0078 |
| | | 0.07 | 0.6579 | 0.068 | −0.1408 | 0.0598 |
| | | 0.1 | 0.8483 | 0.1908 | −0.1707 | −0.0127 |
| | Hydroxyl radicals | 0.02 | −0.3469 | 0.1276 | −0.0801 | −0.0359 |
| | | 0.05 | −0.3103 | 0.404 | −0.2477 | 0.06 |
| | | 0.07 | −0.2878 | 0.4868 | −0.2543 | 0.0473 |
| | | 0.1 | −0.1743 | 0.5756 | −0.3574 | 0.0877 |
| | Multiplexed | 0.01 | −0.1296 | 0.2705 | −0.5133 | 0.0585 |
| | | 0.02 | −0.1101 | 0.2433 | −0.5492 | 0.0592 |
| | | 0.05 | 0.3464 | 0.0957 | −0.3726 | 0.0578 |
| | | 0.07 | 0.4967 | 0.0458 | −0.3126 | 0.0915 |
| | | 0.1 | 0.7541 | 0.0867 | −0.332 | 0.0594 |
| Time (min) | Mechlorethamine | 200 | −0.258 | 0.0654 | 0.1541 | −0.0811 |
| | | 250 | −0.2546 | 0.0829 | 0.1117 | −0.0992 |
| | | 300 | −0.2339 | 0.086 | 0.1217 | −0.0969 |
| | | 350 | −0.2303 | 0.1072 | 0.137 | −0.1092 |
| | $H_2O_2$ | 10 | −0.4671 | −0.2114 | 0.0914 | −0.0799 |
| | | 14 | −0.4641 | −0.2078 | 0.0877 | −0.0799 |
| | | 19 | −0.4633 | −0.2014 | 0.089 | −0.0725 |
| | | 25 | −0.4633 | −0.198 | 0.0893 | −0.0752 |
| | | 29 | −0.4617 | −0.2021 | 0.0847 | −0.073 |
| | | 32 | −0.4621 | −0.2032 | 0.0865 | −0.0701 |
| | Singlet oxygen | 150 | 1.1962 | −0.1937 | 0.0388 | −0.1394 |
| | | 200 | 1.4986 | −0.0674 | 0.1048 | −0.2139 |
| | | 250 | 1.5992 | 0.0166 | 0.0704 | −0.2432 |
| | | 300 | 1.6098 | 0.0338 | 0.005 | −0.2247 |

SUPPLEMENTARY TABLE S1-continued

Principal components analysis scores for all reagents.

| | | Conc. (mM) or Time (min) | PC 1 | PC 2 | PC 3 | PC 4 |
|---|---|---|---|---|---|---|
| | | 350 | 1.618 | 0.0698 | 0.0003 | −0.2176 |
| | | 400 | 1.6362 | 0.0724 | 0.0088 | −0.2097 |
| | Hydroxyl radicals | 0.6 | −0.4731 | 0.1206 | −0.1155 | −0.0795 |
| | | 0.9 | −0.4532 | 0.1754 | −0.125 | −0.0607 |
| | | 1.1 | −0.4447 | 0.2027 | −0.1335 | −0.0343 |
| | | 2.1 | −0.4254 | 0.2387 | −0.1629 | −0.0497 |
| | Multiplexed 0.06 mM $CuCl_2$ and 0.04 mM $FeSO_4$ | 8.3 | −0.4028 | 0.0176 | 0.0157 | −0.1169 |
| | | 16.7 | −0.3958 | −0.003 | −0.0462 | −0.111 |
| | | 33.3 | −0.3365 | −0.0776 | −0.0517 | −0.0774 |
| | | 50.0 | −0.2138 | −0.0879 | −0.0769 | −0.0512 |
| | | 83.3 | −0.0093 | −0.1223 | 0.0081 | 0.0034 |
| | | 116.7 | 0.2114 | −0.1922 | 0.1038 | 0.0365 |
| | | 166.7 | 0.5266 | −0.1759 | −0.0105 | 0.0495 |
| | | 250.0 | 0.8633 | −0.2135 | 0.0797 | 0.0736 |
| | Multiplexed 0.08 mM $CuCl_2$ and 0.02 mM $FeSO_4$ | 3.3 | −0.5679 | −0.1537 | −0.014 | −0.0853 |
| | | 6.7 | −0.5666 | −0.1488 | −0.0226 | −0.0674 |
| | | 20.0 | −0.4569 | −0.2969 | −0.0395 | 0.0069 |
| | | 33.3 | −0.3007 | −0.2752 | 0.054 | 0.0633 |
| | | 46.7 | −0.1198 | −0.3125 | 0.0435 | 0.104 |
| | | 60.0 | 0.0373 | −0.3173 | 0.1939 | 0.146 |
| | | 73.3 | 0.1471 | −0.281 | 0.1634 | 0.1981 |
| | | 86.7 | 0.3241 | −0.3199 | 0.2481 | 0.212 |
| | | 100.0 | 0.4315 | −0.3093 | 0.2589 | 0.2532 |
| | | 166.7 | 0.8192 | −0.2291 | 0.279 | 0.315 |
| In Vivo | Mechlorethamine | 35 | −0.0198 | 0.4806 | 0.304 | 0.2008 |
| | | 40 | 0.1889 | 0.5068 | 0.2353 | 0.1775 |
| | | 50 | 0.4151 | 0.5037 | 0.2844 | 0.2169 |
| | | 60 | 0.4448 | 0.5714 | 0.3703 | 0.1673 |
| | $H_2O_2$ | 5 | −0.5231 | −0.2088 | 0.0941 | −0.0569 |
| | | 6 | −0.2878 | −0.032 | 0.1025 | −0.0258 |
| | | 7 | −0.3114 | −0.0179 | 0.1011 | −0.0114 |
| | | 8 | −0.3675 | −0.0875 | 0.0481 | −0.0279 |
| | | 9 | −0.4438 | −0.1663 | 0.0577 | −0.0636 |
| | | 10 | −0.5076 | −0.2598 | 0.0146 | −0.0853 |
| | | 11 | −0.4535 | −0.2647 | 0.0844 | −0.0863 |
| | | 12 | −0.4963 | −0.2964 | 0.1076 | −0.0641 |
| | Singlet oxygen | 11.7 | −0.0765 | −0.1321 | −0.3959 | 0.1042 |
| | | 16.7 | 0.0659 | −0.1515 | −0.2195 | 0.0714 |
| | | 30.0 | 0.1345 | −0.2305 | −0.093 | 0.0804 |
| | | 43.3 | 0.1714 | −0.3517 | −0.299 | 0.1306 |
| | | 58.3 | 0.2181 | −0.3444 | −0.1915 | 0.1224 |
| | | 70.0 | 0.2438 | −0.4168 | −0.1874 | 0.1378 |
| | | 83.3 | 0.2461 | −0.5589 | −0.212 | 0.2212 |
| | Hydroxyl radicals | 3 | −0.4632 | −0.0685 | −0.0172 | −0.1283 |
| | | 4 | −0.3465 | 0.1997 | 0.0733 | −0.018 |
| | | 5 | −0.3044 | 0.3222 | 0.1587 | 0.0185 |
| | | 6 | −0.2921 | 0.3311 | 0.1472 | 0.0406 |
| | | 7 | −0.2168 | 0.3361 | 0.2032 | 0.0435 |
| | | 8 | −0.1834 | 0.3718 | 0.1813 | 0.0333 |
| | | 9 | −0.194 | 0.3631 | 0.1632 | 0.0354 |

Chemotherapeutic alkylating agents were detected immediately upon exposure to the DNA-SWNT complex. Emission red shifts of up to 6 meV and concomitant attenuation were observed via n-IR spectrofluorimetry (FIGS. 23A-23C and FIG. 28). The red shifting rates caused by nitrogen mustards melphalan and mechlorethamine were similar (first order $k_{obs}$=0.014 min$^{-1}$ and 0.012 min$^{-1}$ respectively), while cisplatin promoted three-fold lower shift rate ($k_{obs}$=0.0047 min$^{-1}$). The rate of drug alkylation to an unbound test oligonucleotide containing one guanine nucleobase, analyzed by polyacrylamide gel electrophoresis, was similar to the rate of drug-induced DNA-SWNT shift ($k_{obs}$=0.0083 min$^{-1}$ for mechlorethamine and $k_{obs}$=0.0058 min$^{-1}$ for cisplatin; direct comparison to d(GT)$_{15}$ (SEQ ID NO: 10) is provided in FIG. 29). The DNA-SWNT response of melphalan was slower than the unbound DNA alkylation ($k_{obs}$=0.028 min$^{-1}$), which may have been due to the steric bulk of this larger molecule as it interacts with the nanotube-bound DNA. The rates of SWNT emission shifting were highly sequence-dependent, proportional to the abundance of guanine in the bound oligonucleotide sequence (FIG. 30), which was consistent with the known preference of melphalan for alkylating purine nucleobases. The DNA-SWNT complex emission may have responded to the alkylation of the bound oligonucleotide via a solvatochromic shift mechanism, perhaps due to the introduction of the drug adduct into the immediate vicinity of the nanotube, resulting in conformational changes of the encapsulating DNA.

Hydrogen peroxide was detected by the DNA-SWNT complex via attenuation of both (6,5) and (7,5) fluorescence bands to similar extents with slight shifting of peak wavelengths (FIG. 22C). Reversible charge-transfer quenching upon H$_2$O$_2$-SWNT contact, caused by peroxide's high reduction potential, may have been responsible for this behavior. While (6,5) and (7,5) nanotubes signals showed similar attenuation, small bandgap nanotubes attenuate to a greater extent, in agreement with absorption spectroscopy studies (data provided in FIG. 31). This provides additional basis for fingerprinting hydrogen peroxide for studies involving small-bandgap SWNT species.

Figure 23A:
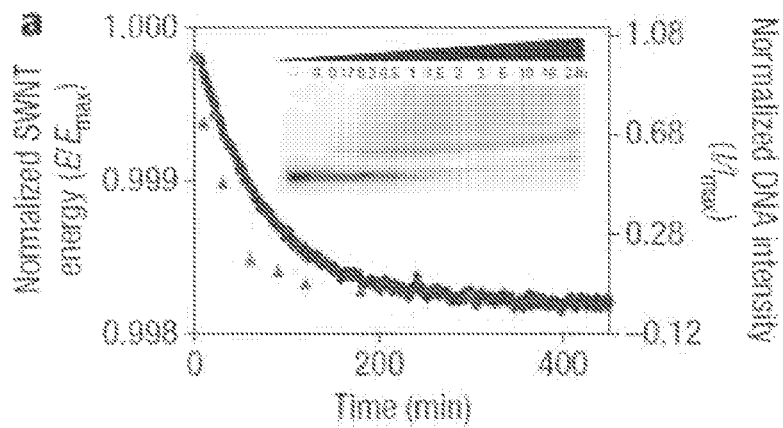
FIGS. 23A-23C show time dependent spectral changes of DNA-SWNT complexes and corresponding gel electrophoresis results.
Figure 23B:
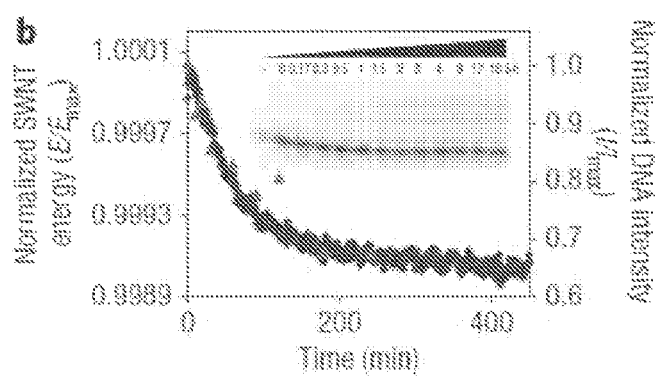
Figure 23C:
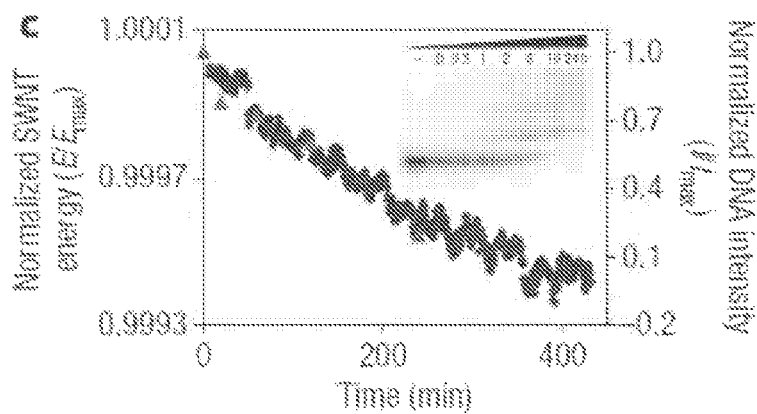
Figures 23D, 23E, 23F:
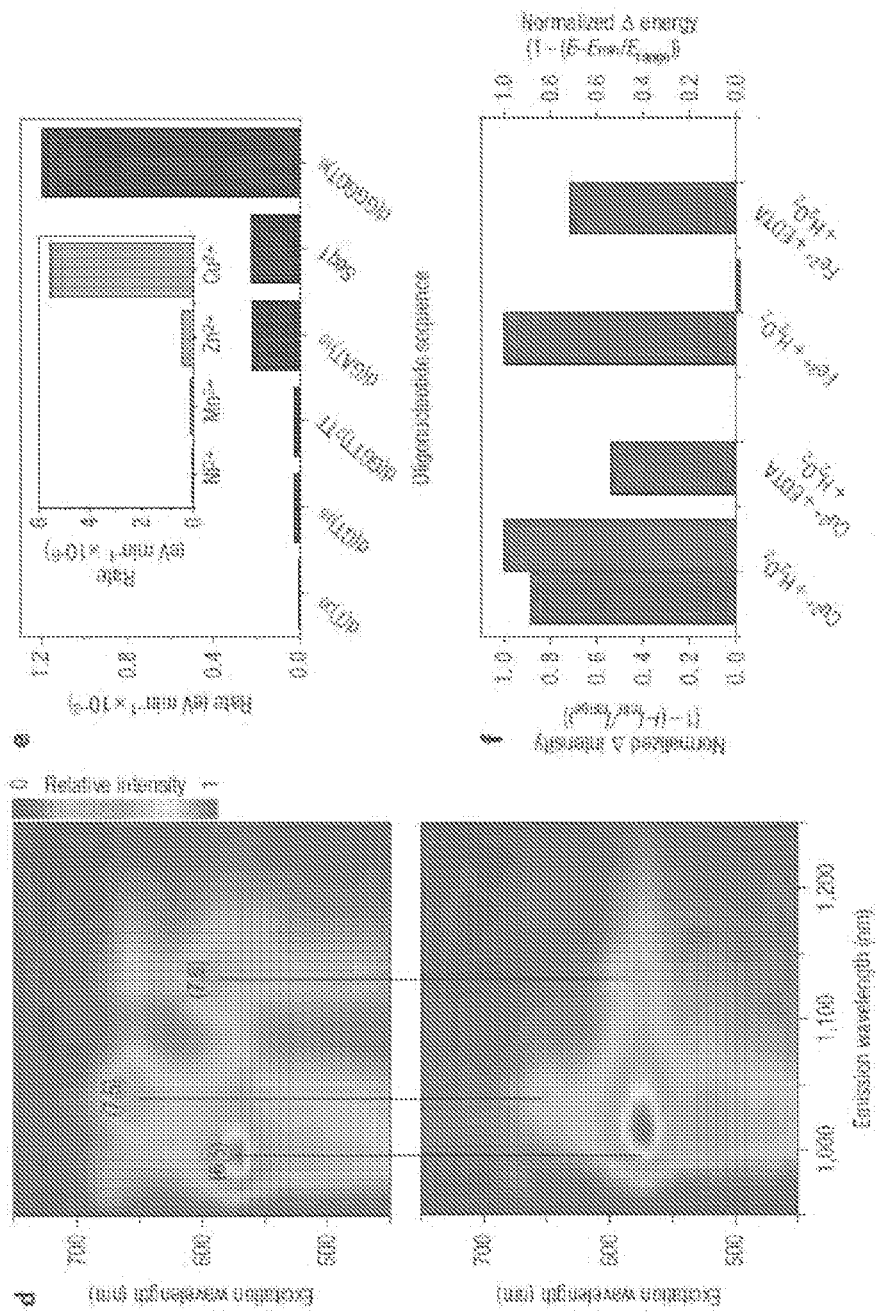
FIG. 23D is a 3D photoluminescence profile. FIG. E23E illustrates the rates of change in spectral properties for DNA-SWNT complexes with different sequences (or in the presence of different metal ions, inset).
FIGS. 23F-H is a graph demonstrating the effect of different inhibitors on singlet oxygen-induced spectral changes of DNA-SWNT complexes.
Figure 23G:
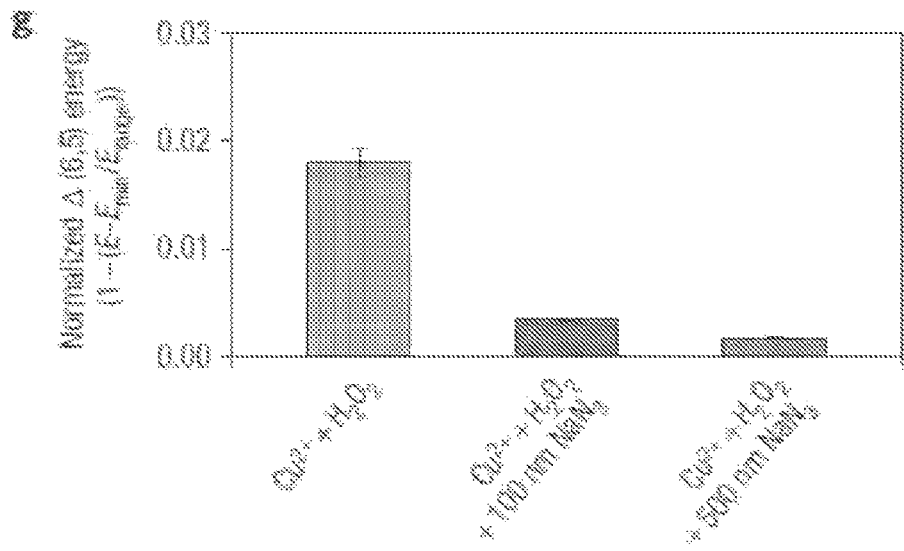
Figure 32:
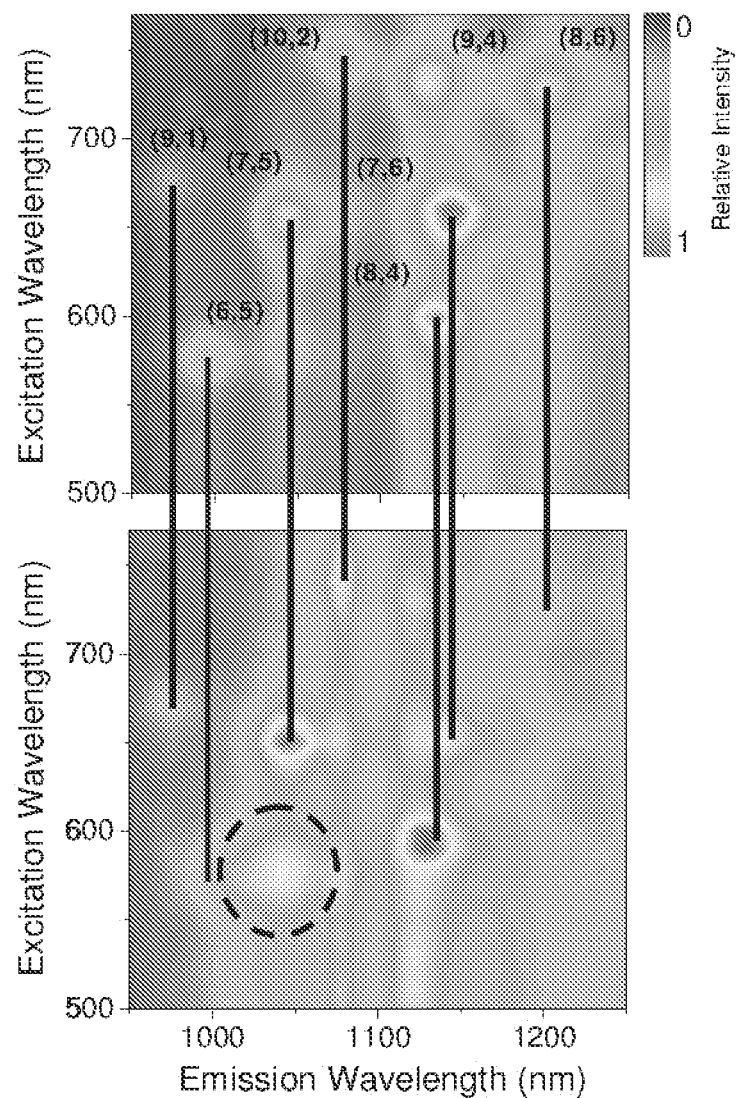
FIG. 32 is a 3D photoluminescence profile of DNA-SWNT before (top) and after (bottom) exposure to $CuCl_2$ and hydrogen peroxide.
Figure 33:
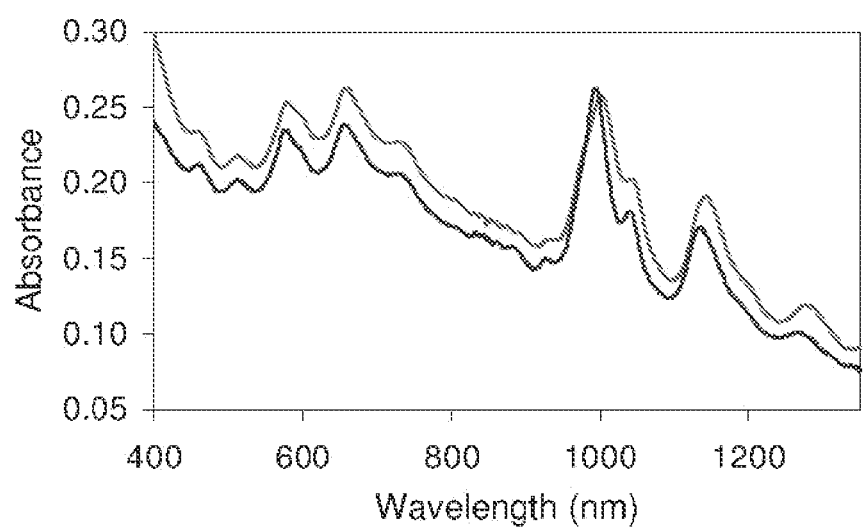
FIG. 33 presents spectra of DNA-SWNT before and after exposure to single oxygen.

Singlet oxygen formed in the direct vicinity of the DNA-nanotube complex induces a pronounced red-shift in the (6,5) nanotube emission with virtually no (7,5) nanotube shift (FIG. 22D), as confirmed by the 3D photoluminescence profile (FIG. 22D). Shifts of over 60 meV (50 nm) have been observed, as well as small red and blue shifts of other SWNT species along with relative attenuation of large bandgap species (FIG. 32). Similar trends are seen in absorption spectra (FIG. 33). The effect of singlet oxygen on the DNA-SWNT signal was sequence-dependent, as various strands used to encapsulate the nanotube in place of d(GT)$_{15}$ (SEQ ID NO: 10) promote shift rates roughly proportional to the abundance of purine nucleobases in the sequence (FIG. 23E); purines can be fairly easily oxidized. The rate measured among several metal ion catalysts (FIG. 23E inset) was greater for ions that demonstrated higher binding affinity to nucleobases, suggesting that singlet oxygen may have caused the red shift when produced in the vicinity of the nucleobases. By preventing singlet oxygen generation in the nanotube's immediate vicinity, via chelating all available Cu$^{2+}$ ions with EDTA, the wavelength shift was completely inhibited and signal attenuation was reduced (FIG. 23F). Exposure to the singlet oxygen scavenger, sodium azide, significantly reduced the magnitude of the (6,5) band shift (FIG. 23G); however, its introduction after shifting did not cause a reversal. These experiments suggest that this unique SWNT response is due to a singlet oxygen-induced DNA adduct resulting from nucleobase oxidation, such as 8-oxo-deoxyguanosine. The oxidized nucleobase increases the polarity of the nanotube's microenvironment, causing a solvatochromic red-shift. Response variations between nanotubes may have resulted from SWNT structural and electronic differences which may have caused DNA-nanotube interactions to vary across species, resulting in diverse responses to DNA adduct formation.

Figure 23H:
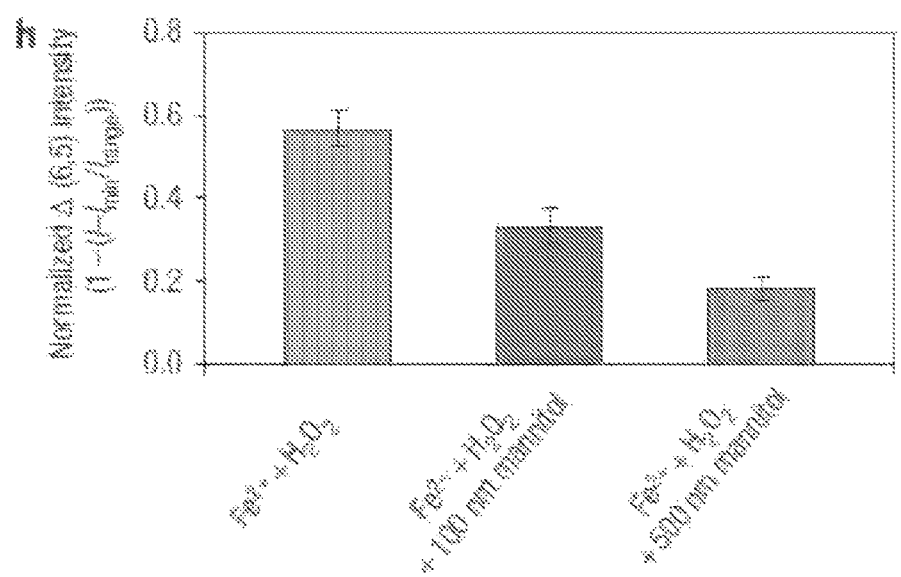
Figure 34:
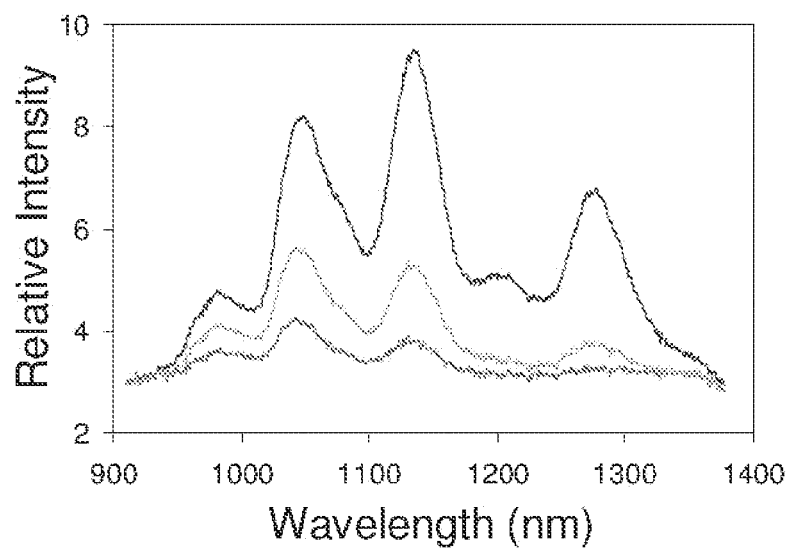
FIG. 34 relates to hydroxyl radical detection by DNA-SWNT.

Generation of the hydroxyl radical by the Fenton reaction was detected by the DNA-SWNT complex via attenuation of the nanotube's photoluminescence. The Fe$^{2+}$ ion catalyzes hydroxyl radical formation in the presence of H$_2$O$_2$, which, in the vicinity of DNA-SWNT, greatly attenuates both (6,5) and (7,5) fluorescence bands without shifting the peak wavelengths and generally attenuates the (7,5) nanotube emission to a greater extent (FIG. 22E). Chelation of all available Fe$^{2+}$ with EDTA reduced, but did not eliminate, signal attenuation, suggesting that damage can be detected without close association of Fe$^{2+}$ to the nucleobases (FIG. 23F). Mannitol, a hydroxyl radical quencher, prevented signal attenuation when added before initiating the reaction (FIG. 23H). Hydroxyl radical interaction with DNA-SWNT exhibits highly disproportional attenuation of small-bandgap species emission (FIG. 34). Not wishing to be bound by any theory, the DNA-SWNT complex may have detected the hydroxyl radical by induced DNA damage. The resulting DNA adduct includes a species which induces photoluminescence attenuation by a charge-transfer mechanism.

Figure 24A:
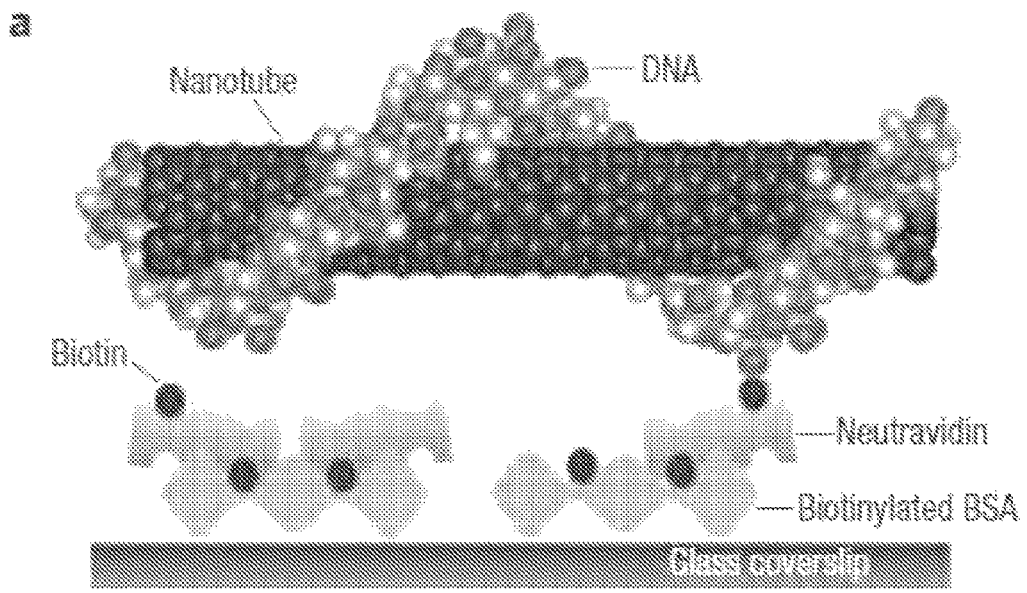
FIG. 24A is a schematic diagram of neutravidin mediated DNA-SWNT immobilization on a surface.
Figure 24B:
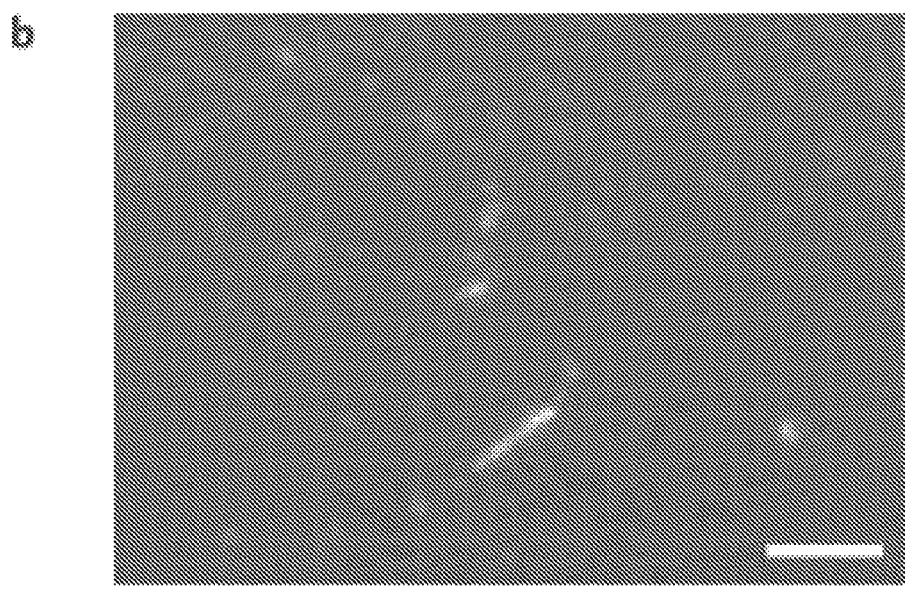
FIG. 24B is a NIR photoluminescence image of a surface so modified.
Figure 24C:
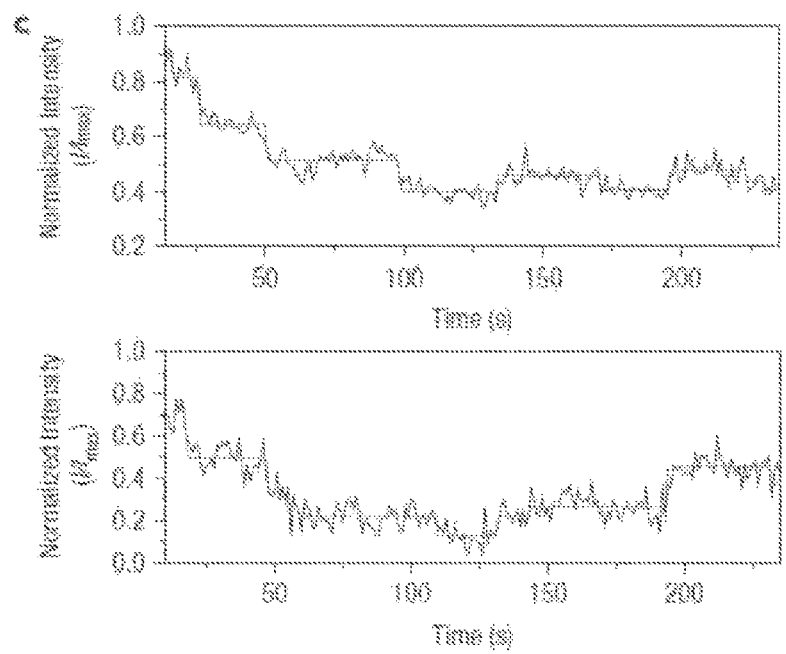
FIG. 24C show time traces of SWNT quenching.
Figure 24D:
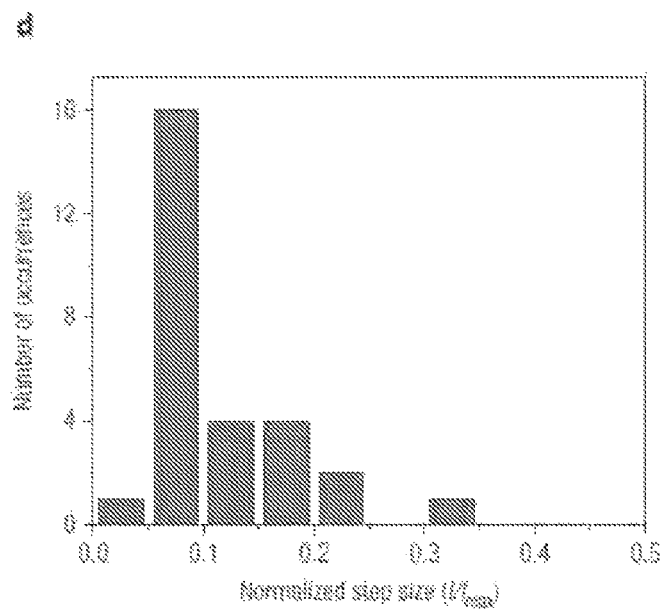
FIG. 24D is a histogram of normalized quantized intensity changes after regression with a stochastic step-fitting algorithm.

Stepwise n-IR photoluminescence quenching of surface-tethered DNA-SWNT complexes demonstrate single-molecule detection of hydrogen peroxide. Recent work has shown that analyte-SWNT interactions can be studied at the single-molecule level via immobilization of surfactant-suspended nanotubes in agarose. We encapsulated nanotubes with a 1:4 ratio of biotinylated to non-biotinylated d(GT)$_{15}$ (SEQ ID NO: 10), allowing Neutravidin-specific binding of DNA-SWNT to a BSA-biotin treated surface (FIG. 24A). (See Supplementary Methods) Immobilized DNA-SWNT complexes were imaged via their n-IR photoluminescence signal upon laser excitation (FIG. 24B). Time traces of SWNT quenching (FIG. 24C) were obtained by measuring the intensity of 4-pixel spots in movies recorded at 1 frame/s, resulting in multiple traces which exhibit single-step attenuation upon perfusion of hydrogen peroxide. The traces yielded a narrow histogram of normalized quantized intensity changes after regression with a stochastic step-fitting algorithm, confirming the discrete nature of the interaction (FIG. 24D). The average normalized step height of 0.05-0.1 is consistent with a 90 nm exciton excursion range and spot size of 900 nm, confirming a quantized single-step magnitude of 0.1. These measurements demonstrate single-molecule detection of hydrogen peroxide, providing promise for new classes of biosensors with this level of sensitivity.

Figure 25A:
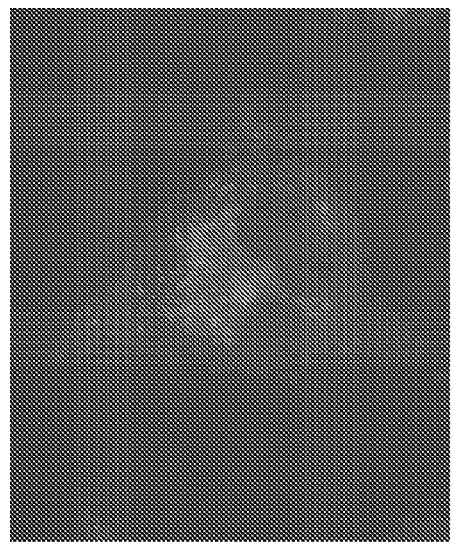
FIGS. 25A-25D are microscope images of murine 3T3 cells after exposure to DNA-SWNT complexes.
Figure 25B:
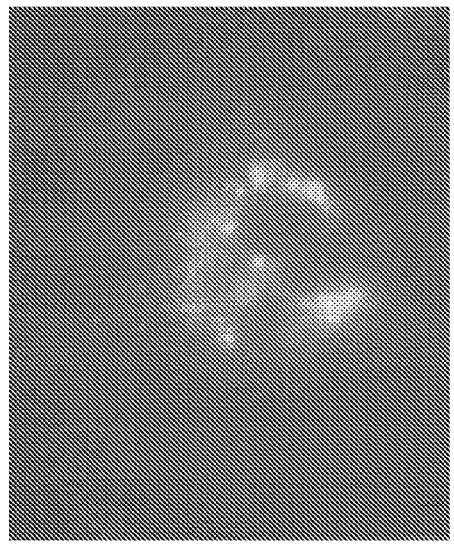
Figure 25C:
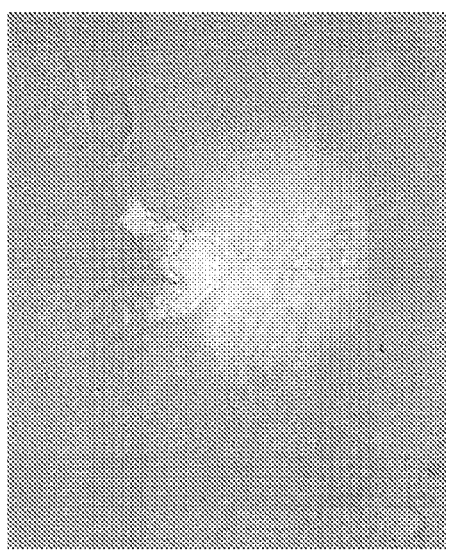
Figure 25D:
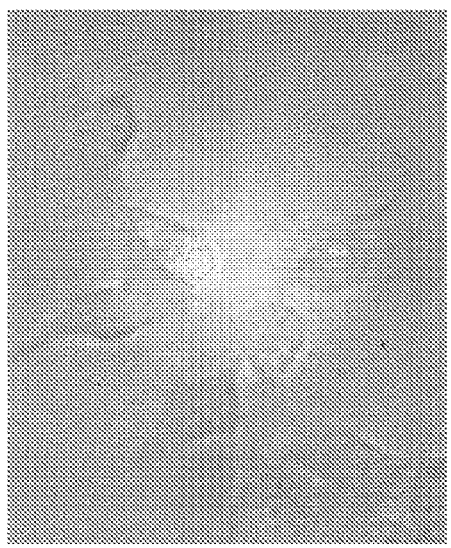

Nucleic acid encapsulated SWNT enter cells via endocytosis without exhibiting cytotoxic effects at doses of at least 5 mg/L while maintaining their photoluminescence properties, which can be perturbed in situ. Colocalization images of nanotube fluorescence in murine 3T3 cells with a lysosomal stain showed partial overlap, suggesting DNA-SWNT presence in both lysosomes and the cytoplasm (FIG. 25A-B). Perfused chemotherapeutic drugs and ROS induce SWNT spectral changes in real time within live cells, allowing detection in situ using this multi-modal technique. The photoluminescence intensity changes of DNA-SWNT, upon interaction with genotoxins, can be spatially resolved within single cells, as shown in images before and after inducing hydroxyl radical formation (FIG. 25C-D).

Figures 25E, 25F, 25G, 25H:
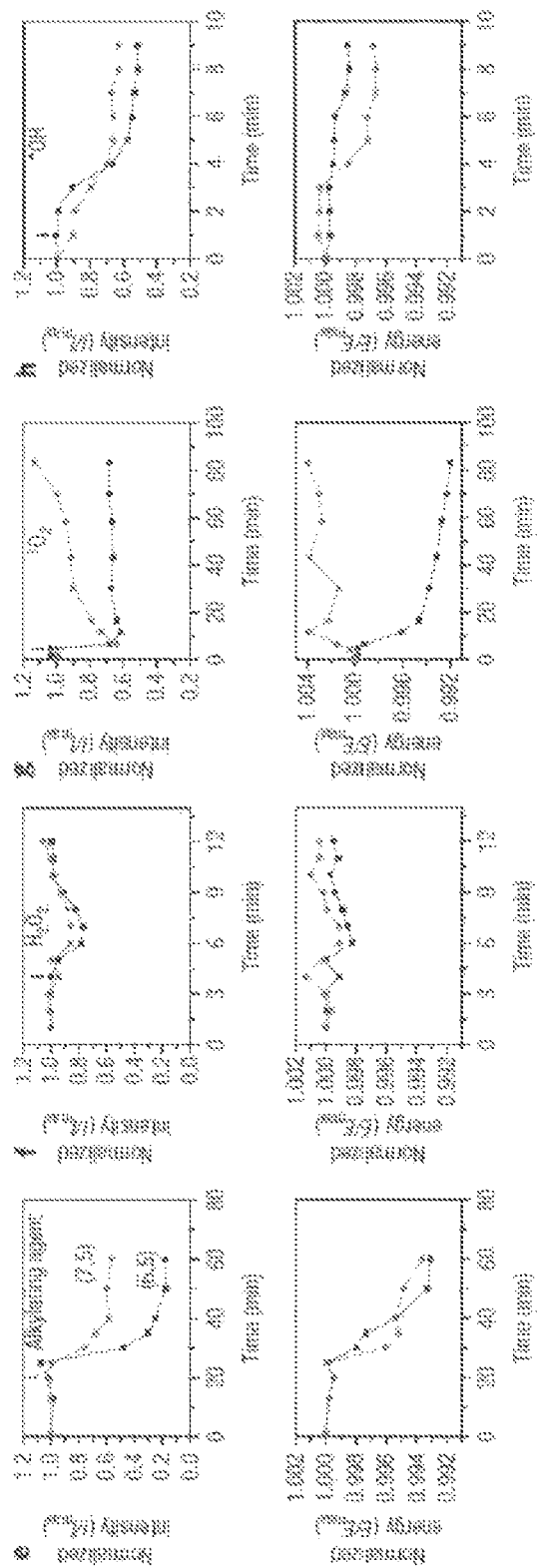
FIGS. 25E-25H show time dependent changes in DNA-SWNT spectral properties after the cells are exposed to a variety of DNA-damaging agents.
Figure 25I:
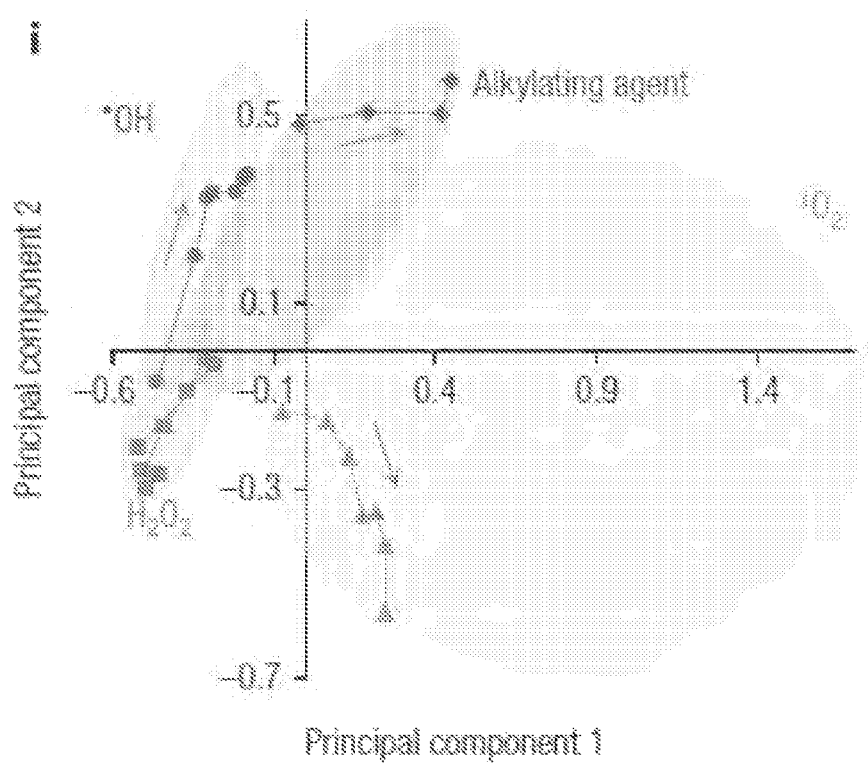
FIG. 25I shows results of principal components analysis of the spectral changes.
Figure 35:
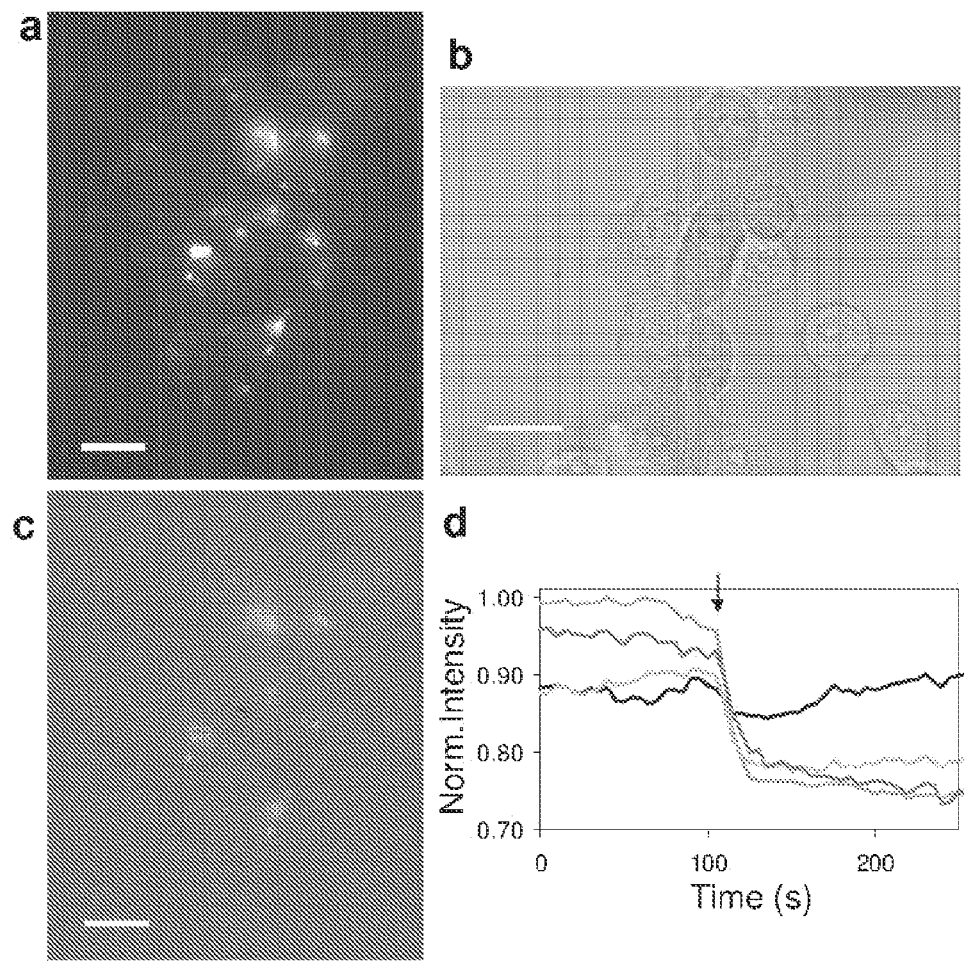
FIGS. 35A-35C are microscope images taken during real-time imaging of hydrogen peroxide quenching in live cells.
FIG. 35D are traces of individual emitting particles demonstrate various degrees of signal attenuation.

Four genotoxins are demonstrably detected and identified in live cells spectroscopically. Real-time measurements reveal that the alkylating agent mechlorethamine induces a detectable attenuation and peak shift of both (6,5) and (7,5) nanotube bands following perfusion of the drug into cell media, similar to in vitro behavior (FIG. 25E). Perfusion with hydrogen peroxide alone induces a temporary attenuation of both nanotube bands, with minimal shifting, that reverses within 5-10 minutes (FIG. 25F). The reversibility is expected due to cellular enzymes which decompose hydrogen peroxide. Movies of SWNT emission in cells elucidate spatially heterogeneous quenching observed upon H$_2$O$_2$ perfusion (FIG. 35). Singlet oxygen (FIG. 25G) and hydroxyl radicals (FIG. 25H), generated in vivo by perfusion of their respective catalytic reagents, producing trends generally consistent with the DNA-SWNT response in vitro, although intensities exhibit some deviation. Such events are expected during detection in single cells, as cell movement can cause intensity fluctuations. Additionally, endosomal localization and the DNA coating may lower the detection limit due to aggregation caused by endosome fusion and protein binding to DNA-SWNT. Analysis via PCA reveals that cellular responses uniquely fingerprint each genotoxin. A principal components plot (FIG. 25I) shows analyte data separated into distinct regions, consistent with in vitro data (FIG. 25J).

Methods

SWNT Preparation

Raw HiPC® SWNT (Rice University) were suspended via bath sonication for 1 hour in a 1:1 mass ratio with the d(GT)$_{15}$ oligonucleotide (SEQ ID NO: 10). The resulting solution was centrifuged at 16,300 g for 90 minutes and the pellet was discarded. Raw CoMoCAT SWNT (Southwest Nanotechnologies) were suspended via probe-tip sonication at 10 W for 10 minutes in a 4:1 ratio with d(GT)$_{15}$ (SEQ ID NO: 10) in 0.1 M NaCl cooled by an ice bath. The resulting GT-CoMoCAT solution was centrifuged at 16,300 g for 90 minutes and the pellet was discarded.

Spectroscopy and Microscopy

Near-infrared photoluminescence spectra were acquired using 785 nm excitation and an Acton SP-150 spectrograph coupled to a Princeton Instruments OMA V InGaAs detector or with a Kaiser Holospec f/1.8 Imaging Spectrograph (Kaiser Optical). Absorption measurements were taken with a Shimadzu UV-3101 PC UV-VIS-NIR Scanning Spectrophotometer. Photoluminescence 3D profiles were acquired with an in-house built spectrofluorometer incorporating a xenon arc lamp, Kratos GM-252 monochromators, and E1-L Germanium Detector (Edinburgh Instruments). Single-molecule and cell microscopy studies used a Carl Zeiss Axiovert 200 fluorescence microscope coupled to a Princeton Instruments 2D-OMA V InGaAs camera with a 256×320 pixel array and Acton spectrograph. Visible fluorescence images were acquired with an AxioCam MRm CCD camera. Spectra were processed by fitting to a Gaussian lineshape to determine peak center wavelength.

Chemotherapeutic Agent Kinetics

To elucidate drug-induced shifting (FIG. 22), a solution of 5 mg/L of GT-CoMoCAT SWNT in 100 mM Tris buffer (pH 7.4) was exposed to 20 mM mechlorethamine, and spectra were acquired at room temperature. For kinetic measurements, 5 mg/L of GT-HiPC® in 100 mM Tris buffer (pH 7.4) was exposed to the alkylating agent melphalan, mechlorethamine, or cisplatin at a concentration of 0.5 mM. Photoluminescence spectra were taken over 400-600 minutes at 37° C. Unbound oligonucleotide kinetics were measured via polyacrylamide gel electrophoresis (PAGE) on the test sequence: 5'-TTT TTG TTT T-3' (SEQ ID NO: 13). The sequence was labelled with $^{32}$P at the 5' end and exposed to 0.5 mM of alkylating agent in 100 mM Tris (pH 7.5) at 37° C. Aliquots were removed at each time point and held at −80° C. before 20% PAGE.

Reactive Oxygen Species

Transient photoluminescence measurements were conducted by exposing GT-CoMoCAT SWNT in 20 mM Tris (pH 7.3) and 0.1 M NaCl (henceforth "buffer") to 10 mM $H_2O_2$ in the case of hydrogen peroxide experiments. Singlet oxygen was induced with 0.1 mM $CuCl_2$ and 10 mM $H_2O_2$; hydroxyl radicals with 0.05 mM $FeSO_4$ and 10 mM $H_2O_2$. Cations were added to DNA-SWNT in buffer one hour prior to the addition of $H_2O_2$ to rule out cation-induced effects[33]. Spectra were acquired over 10-400 minutes. Photoluminescence 3D profiles were taken using 5 mg/L GT-CoMoCAT SWNT in buffer with $CuCl_2$. The second profile was taken 24 hours after exposure to 3.6 mM $H_2O_2$. All ROS experiments were conducted at room temperature.

ROS Measurements After Cation Chelation

Solutions of 5 mg/L of GT-CoMoCAT SWNT in buffer plus 0.1 mM $CuCl_2$ or 0.1 mM $FeSO_4$ and 2 mM EDTA were made prior to reacting with 1 mM $H_2O_2$. Photoluminescence measurements were taken 24 hours later.

ROS Measurements Using Different DNA Sequences/cations

Solutions of 5 mg/L HiPC® SWNT encapsulated by five different DNA sequences were made using the bath sonication method described above. Sequences were d(T)$_{30}$ (SEQ ID NO: 14), d(GGTT)$_7$TT (SEQ ID NO: 15), d(GAT)$_{10}$ (SEQ ID NO: 16), d(GGGGT)$_6$ (SEQ ID NO: 17) and an oligonucleotide denoted Seq 1 containing the 27-nucleotide sequence 5'-ACC TGG GGG AGT ATT GCG GAG GAA GTT-3' (SEQ ID NO: 18) (purinic content=67%). All other sequences were 30 nucleotides long. Photoluminescence of each sequence was measured upon reaction with 0.1 mM $CuCl_2$ and 3.6 mM $H_2O_2$ in buffer. Photoluminescence of GT-HiPC® was measured 24 hours after reaction of 0.1 mM of various metallic cations with 3.6 mM $H_2O_2$ after 24 hours to determine cation dependence on shift.

Cell Culture

Murine NIH/3T3 cells were cultured with HEPES-buffered Dulbecco's Minimal Essential Media (Sigma) supplemented with 10% fetal bovine serum (Biomeda, Foster City, Calif.). The cells were incubated with 2 mg/L of GT-CoMoCAT SWNT for 6-8 hours before trypsin digestion and transferring to a separate container. Cells were plated on glass-bottom petri dishes (MatTek) for microscopy.

Lysosomal Imaging and Photoluminescence/Visible Overlays

Lysosomal dye colocalization images were taken two hours after exposing cells containing GT-CoMoCAT SWNT to 70 nM of LysoTracker Red (Invitrogen). Cells were alternately exposed to white light excitation passed through a rhodamine dye filter cube for dye excitation and a 785 nm laser for SWNT imaging. Nanotube photoluminescence overlays on visible cell images were acquired by exposing the cells alternately to halogen epi-illumination and 785 nm excitation with detection by 2D InGaAs camera.

Live Cell Drug/ROS Perfusion

Cells adhered to glass-bottom Petri dishes were imaged inside a micro-incubation platform (Model DH-40i, Warner Instruments, Inc). Alkylating drugs and other reagents were perfused via syringe. Cells were bathed in media with FBS during chemotherapeutics experiments. Mechlorethamine dissolved in DMEM media with FBS was perfused to reach a final concentration of 50 mM. Media was exchanged for saline solution just before ROS experiments to prevent cation precipitation and hydrogen peroxide degradation. The salts $CuCl_2$ or $FeSO_4$ were perfused approximately 30 minutes before measurements, at 1 mM and 0.1 mM, respectively, while 30 mM $H_2O_2$ was perfused during data acquisition. Laser power was limited to 1.1 mW.

Supplementary Methods

Single-Molecule Studies

DNA-SWNT was suspended via probe-tip sonication in a 4:1 DNA:HiPC® SWNT ratio for 2 min. A ratio of 1:4 biotinylated:non-biotinylated d(GT)$_{15}$ DNA (SEQ ID NO: 10) was used to produce complexes with multiple biotinylated oligonucleotides per SWNT. Solutions were centrifuged at 16,000 g for 90 minutes and the pellet was discarded. A sample chamber for single-molecule experiments was created as described. The surface was successively treated with 1 mg/ml biotinylated-BSA in T100 (10 mM Tris [pH 8.0] and 0.1 M NaCl) and 0.2 mg/ml Neutravidin in T100. Biotinylated DNA-SWNT of concentration approximately 1 mg/L in T100 was added to the sample chamber and incubated for at least 30 minutes before imaging. Channels were flushed with deionized water before imaging. Near-IR movies were captured at 1 frame/s using 633 nm excitation. An aliquot of 10 µM $H_2O_2$ was dropped on the inlet hole of the slide and allowed to diffuse into the sample chamber during data acquisition.

Concentration-Dependent Genotoxin Responses

Buffered solutions of 5 mg/L GT-CoMoCAT SWNT were prepared to expose the SWNT complexes to six different concentrations of each genotoxin: mechlorethamine, $H_2O_2$, singlet oxygen, and hydroxyl radicals. The latter two were prepared by first adding several concentrations of $CuCl_2$ for singlet oxygen or $FeSO_4$ for hydroxyl radicals one hour before initiating the reactions with 10 mM $H_2O_2$. Spectra were acquired at a single time point for each genotoxin.

Multiplexed Detection Experiments

Solutions of 5 mg/L of GT-CoMoCAT SWNT in buffer were exposed to mixtures of $CuCl_2$ and $FeSO_4$ in several ratios. Cations were introduced to the solutions one hour before starting the reactions with 10 mM $H_2O_2$. Multiple near-infrared spectra were recorded on samples over a five-hour period for transient spectra, or after 1 hour of reaction time for concentration-dependent studies.

Chemotherapeutic Drug Detection Using SWNT Encapsulated in Multiple DNA Sequences Solutions of 5 mg/L HiPC® SWNT were encapsulated by $d(T)_{30}$ (SEQ ID NO: 14), $d(GT)_{15}$ (SEQ ID NO: 10), and $d(GGGGT)_6$ (SEQ ID NO: 17) via bath sonication for 1 hour in a 1:1 SWNT:DNA mass ratio. The resulting solution was centrifuged at 16,300 g for 90 minutes and the pellet was discarded. The near-infrared photoluminescence of each DNA-SWNT complex was measured upon addition of 0.9 mM melphalan in 100 mM Tris buffer (pH 7.4).

FIGURE DESCRIPTIONS

FIG. 22. Multi-modal detection of four reaction pathways. (a) Scheme of interactions on the DNA-SWNT complex: alkylating agent reaction with guanine, hydrogen peroxide (H2O2) adsorption on the nanotube sidewall, singlet oxygen (1O2) reaction with DNA, and hydroxyl radical (•OH) damage to DNA. (b) DNA-SWNT photoluminescence spectra before (blue) and after (green): introducing mechlorethamine (blue border), (c) hydrogen peroxide (magenta border), (d) singlet oxygen (orange border), and (e) hydroxyl radicals (green border). (f) Transient responses of photoluminescence intensity (top) and energy (bottom) of the (6,5) nanotube (black) and (7,5) nanotube (red) upon introducing mechlorethamine, (g) hydrogen peroxide, (h) singlet oxygen, and (i) hydroxyl radicals. Borders are color-coded as above. (j) Plot of first two principal component scores of transient (closed points) and concentration-dependent (open points) detection data (from FIG. 26). Black crosses represent simultaneous singlet oxygen and hydroxyl radical generation (from FIG. 27B). Area-minimized ovals encompass all data sets taken for each analyte, including those not shown. Arrows denote direction of increasing concentration or time.

FIG. 23. Mechanistic studies of SWNT-genotoxin reactions. (a) Photoluminescence shift of (6,5) nanotube (blue curve) upon DNA-SWNT exposure to melphalan. Kinetics trace of unreacted oligonucleotide band intensity (red curve) from 20% PAGE (inset) upon melphalan-induced alkylation of an unbound test sequence. (b) Mechlorethamine-induced response. (c) Cisplatin response. (d) 3D photoluminescence profiles of DNA-SWNT before (top) and after (bottom) inducing singlet oxygen generation. (e) Rate of singlet oxygen-induced (6,5) band red-shifting of SWNT encapsuled by oligonucleotide sequences of increasing purinic character (from left to right; see Methods for Seq 1-67% purines). Rate of (6,5) band red shift induced by singlet oxygen generated by H2O2 and cations with increasing nucleobase-binding capability (from left to right). (f) Chelation of Cu2+ with EDTA prevents all (6,5) peak shifting (red) upon introduction of H2O2. Chelating either Fe2+ or Cu2+ reduces (6,5) signal attenuation (blue) upon introducing H2O2. (g) Sodium azide diminishes (6,5) nanotube energy shift triggered by Cu2+/H2O2. (h) Mannitol reduces Fe2+/H2O2 induced signal attenuation.

FIG. 24. Single-molecule hydrogen peroxide detection. (a) Schematic of biotinylated DNA-SWNT binding to a glass surface via BSA-biotin and Neutravidin. (b) Single near-infrared movie frame showing photoluminescence from several DNA-SWNT complexes (scale bar measures 10 μm). (c) Fitted traces from movie showing single-step SWNT emission quenching upon perfusion of hydrogen peroxide. (d) Histogram of fitted step sizes from five traces taken from one n-IR movie.

FIG. 25. Real-time multiplexed detection of genotoxins in live mammalian cells. (a) Fluorescence of lysosomal stain Lysotracker in 3T3 cells. (b) DNA-SWNT photoluminescence (green) showing partial colocalization with Lysotracker emission. (c) Photoluminescence of DNA-SWNT (green) overlaying visible 3T3 cell images (grey) in the presence of Fe2+ before and (d) after introduction of H2O2. All scale bars measure 20 μm. (e) Photoluminescence intensity (top graph) and energy (bottom graph) of the (6,5) nanotube (black trace) and (7,5) nanotube (red trace) after introducing mecholorethamine (blue borders), (f) hydrogen peroxide (magenta borders), (g) singlet oxygen (orange borders), and (h) hydroxyl radicals (green borders). Arrows denote time of agent addition. (i) Principal components analysis of in vivo data showing segregation of data into discrete regions. Area-minimized ovals encompass regions defined by all available data for each analyte. Arrows denote direction of increasing time.

FIG. 26: Concentration Dependence of SWNT Response to Genotoxins.

Plots of (6,5) and (7,5) SWNT energy and intensity upon varying genotoxin concentrations in buffered 5 mg/L CoMoCAT SWNT solution. (a) Mechlorethamine response acquired 7 hours after addition. (b) Hydrogen peroxide response acquired 24 hours after addition. (c) Singlet oxygen response acquired 1 hour after addition of hydrogen peroxide. (d) Hydroxyl radical response acquired 10.5 hours after addition of hydrogen peroxide. Data acquisition times were chosen when reagent approximately reaches steady-state, with the exception of singlet oxygen due to difficulty of deconvolution of overlapping (6,5) and (7,5) bands over long reaction times at high $CuCl_2$ concentrations.

FIG. 27: Multiplexed Detection of Singlet Oxygen and Hydroxyl Radicals.

Plots of (6,5) and (7,5) intensity and energy upon inducing both singlet oxygen and hydroxyl radical production in the presence of 5 mg/L CoMoCAT DNA-SWNT show characteristics of both agents. With increasing $FeSO_4$/decreasing $CuCl_2$ concentration, the initial intensity drop of the (7,5) nanotube is more pronounced and remains for a longer duration. Concomitantly, the rate of (6,5) energy shift decreases. (a) Intensity (top) and energy (bottom) with 0.02 mM $FeSO_4$, 0.08 mM $CuCl_2$ and 10 mM $H_2O_2$. (b) 0.04 mM $FeSO_4$, 0.06 mM $CuCl_2$ and 10 mM $H_2O_2$. (c) Plots showing concentration dependence of spectral changes. Data was acquired 60 minutes after introduction of reagents. $FeSO_4$ and $CuCl_2$ concentrations were varied in compensatory fashion (with the exception of the 0,0 data point), while $H_2O_2$ concentration remained at 10 mM.

Figure 28:
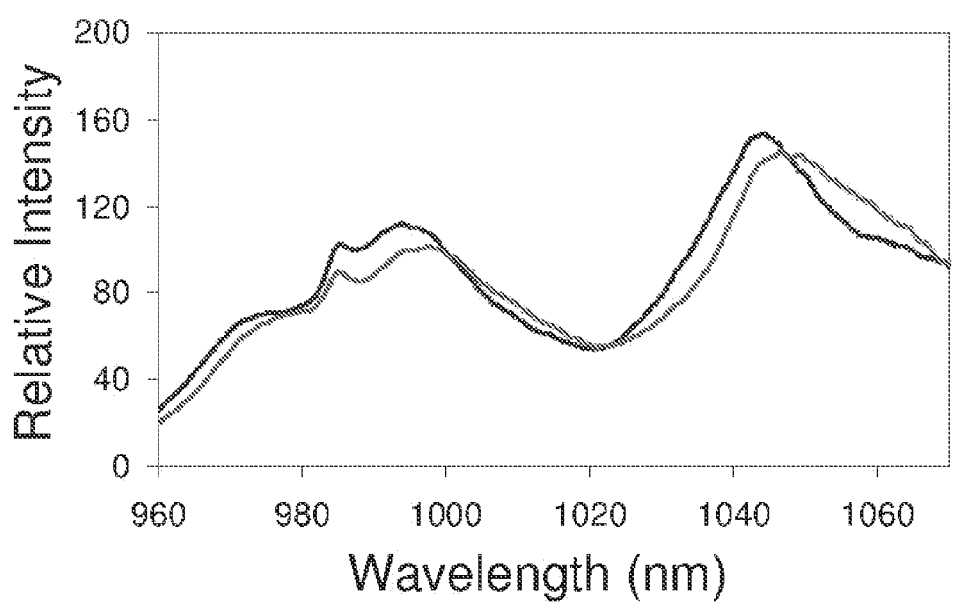
FIG. 28 shows spectra of DNA-SWNT before and after exposure to melphalan.

FIG. 28: Detection of Chemotherapeutic Drugs Using HiPCO SWNT.

The DNA-SWNT complex prepared using HiPCO SWNT (blue) behaved in a qualitatively similar manner to the complex fabricated with CoMoCAT SWNT. Red-shifting of both (6,5) and (7,5) SWNT species is observed upon introduction of melphalan (red).

Figure 29:
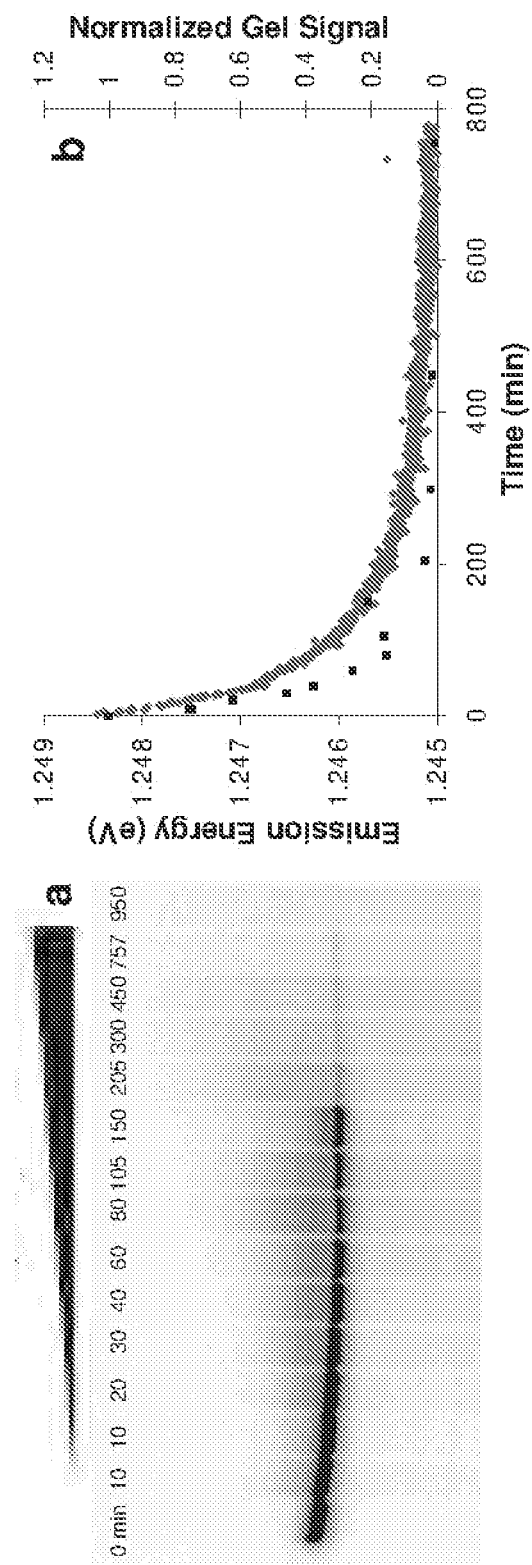
FIGS. 29A-29B compare between damage to free $d(GT)_{15}$ DNA (SEQ ID NO: 10) and DNA-SWNT fluorescence redshift from alkylating agent activity.

FIG. 29: Comparison Between Damage to Free $d(GT)_{15}$ DNA and DNA-SWNT Fluorescence Red-Shift from Alkylating Agent Activity.

(a) PAGE kinetic study of 0.9 mM melphalan reaction on the d(GT)$_{15}$ oligonucleotide sequence (SEQ ID NO: 10). (b) Normalized intensity of the remaining d(GT)$_{15}$ (SEQ ID NO: 10) band from PAGE (black squares) plotted against the red-shift of d(GT)$_{15}$ (SEQ ID NO: 10) encapsulated SWNT exposed to melphalan under the same conditions. The d(GT)$_{15}$ oligonucleotide (SEQ ID NO: 10) did not produce distinct bands in the gel due to multiple G damage sites, prompting the use of a test sequence containing only one guanine base. The test sequence exhibits the same kinetics as shown above upon exposure to melphalan.

Figure 30:
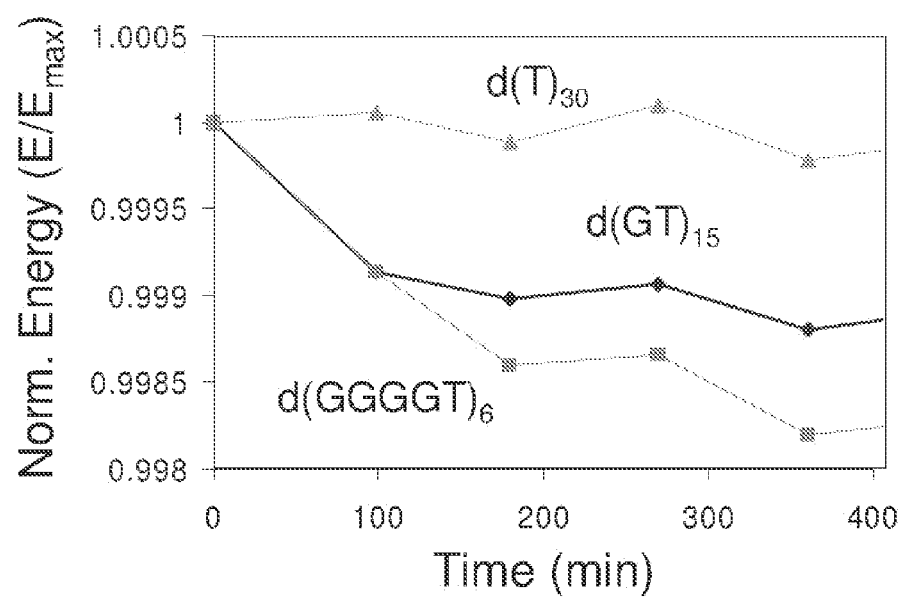
FIG. 30 is a graph illustrating sequence dependence of alkylating agent detection by DNA-SWNT.

FIG. 30: Sequence Dependence of Alkylating Agent Detection by DNA-SWNT.

Rate of (6,5) nanotube photoluminescence red-shift upon melphalan exposure to nanotubes encapsulated by sequences of varying G/T ratios. Nanotube-DNA complexes with sequences containing a higher fraction of guanine display higher reactivity to alkylating drugs, consistent with the observed behavior of nitrogen mustard agents.

Figure 31:
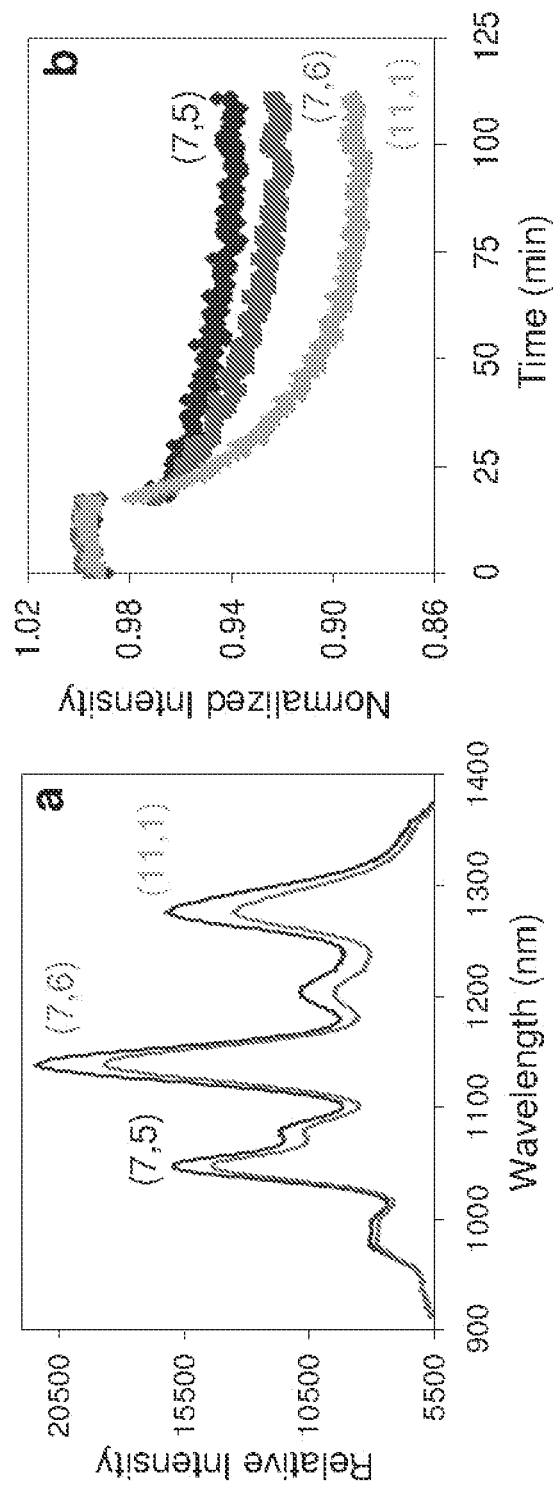
FIGS. 31A-31B are graphs relating to hydrogen peroxide photoluminescence quenching of DNA-SWNT.

FIG. 31: Hydrogen Peroxide Photoluminescence Quenching of DNA-SWNT.

The hydrogen peroxide response of DNA-SWNT using HiPCO nanotubes excited at 633 nm demonstrates a nanotube species dependence. (a) The spectrum taken after exposure to 10 mM H$_2$O$_2$ for 24 hours (red curve) shows greater attenuation of small bandgap nanotubes (emitting at longer wavelengths) compared to the control spectrum (blue curve). Large bandgap nanotubes (such as the (6,5) and (7,5) species) show negligible attenuation differences. Reaction was conducted in 20 mM Tris at a pH of 7.3 with 0.1 M NaCl. (b) Attenuation of three SWNT species showing higher rates for smaller bandgap semiconducting species.

FIG. 32: Singlet Oxygen Reaction on HiPCO DNA-SWNT.

A 3D photoluminescence profile of 5 mg/L DNA-SWNT using HiPCO nanotubes before (top) and 24 hours after (bottom) exposure to CuCl$_2$ and hydrogen peroxide in 20 mM Tris buffer with a pH of 7.3 and 0.1 M NaCl. The (6,5) nanotube undergoes a large red shift (circled in bottom trace), relative intensity changes of nanotube species occur, and total intensity of all peaks fall, demonstrating similar behavior to the CoMoCAT prepared SWNT. Plot intensities were normalized independently. The CoMoCAT SWNT preparation, whose (6,5) and (7,5) relative abundances are approximately 2:1, and whose (6,5) concentration is near 40% of the total SWNT content, was chosen for most of the sensing work in this paper over the HiPCO preparation, whose (6,5) and (7,5) fractional intensities are 3.7% and 4.9% respectively of the total photoluminescence in HiPCO SWNT.

FIG. 33: Singlet Oxygen Shifts SWNT Absorption Bands.

Absorption spectra of 5 mg/L d(GT)$_{15}$ (SEQ ID NO: 10) encapsulated CoMoCAT SWNT before (blue) and 24 hours after (red) inducing singlet oxygen production. The (6,5) band exhibits a red-shift while the (7,5) band shows little change in wavelength. The E$_{22}$ bands exhibit shifting to a lesser degree than E$_{11}$ bands. The samples were buffered in 20 mM Tris at a pH of 7.3 with 0.1 M NaCl.

FIG. 34: Hydroxyl Radical Detection by DNA-SWNT.

DNA-SWNT detects hydroxyl radicals by species-specific quenching. The photoluminescence of smaller bandgap SWNT is quenched disproportionately upon exposure of Fenton reagents to DNA-encapsulated HiPCO-SWNT (633 nm excitation).

FIG. 35: Real-Time Imaging of Hydrogen Peroxide Quenching in Live Cells.

DNA-SWNT emission from 3T3 cells upon introduction of hydrogen peroxide shows inhomogeneous signal attenuation across the cell sample. (a) Near-infrared image of SWNT photoluminescence in 3T3 cells. (b) Visible image. (c) Subtracted near-infrared image (intensity before minus after reagent addition) shows locations where the intensity decreased after addition. Scale bars are 20 µm. (d) Traces of individual emitting particles demonstrate various degrees of signal attenuation. Arrow denotes time of H$_2$O$_2$ introduction. Cells were excited at 785 nm through a 63× microscope objective.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

---

What is claimed is:

1. A nanosensor for determining an analyte, comprising:
   a photoluminescent nanostructure; and
   a polymer comprising a polypeptide associated with the photoluminescent nanostructure, wherein
      the nanosensor emits a first emission of electromagnetic radiation in the absence of the analyte;
      the nanosensor emits a second emission of electromagnetic radiation, distinguishable from the first emission, upon the polypeptide interacting with the analyte; and
      the polymer comprises a polypeptide sequence, or derivative thereof, observed in the venom of a member of the Insecta class; a member of the Hymenoptera order; or a member of the Vespidae or Apidae families.

2. The nanosensor of claim 1, wherein the polymer comprises a polypeptide selected from the group consisting of: an amphiphilic helical polypeptide; a polypeptide including between about 5 and about 50 amino acid residues; and a polypeptide with a molecular weight of between about 400 g/mol and about 10,000 g/mol.

3. The nanosensor of claim 1, wherein the polymer comprises a polypeptide, or derivative thereof, from the Mastoparan or Bombolitin peptide families.

4. The nanosensor of claim 1, wherein the polymer comprises a polypeptide comprising at least one of KKAAAVLLPVLLAAP (SEQ ID NO: 1), EEEECCCCHSSYWYAFNNKT (SEQ ID NO: 2), INLKALAALAKKIL (SEQ ID NO: 3), INLKALAALAKALL (SEQ ID NO: 4), INWKGIAAMAKKLL (SEQ ID NO: 5), IKIMDILAKLGKVLAHV (SEQ ID NO: 6), INIKDILAKLVKVLGHV (SEQ ID NO: 7), IKITTMLAKLGKVLAHV (SEQ ID NO: 8), or SKITDILAKLGKVLAHV (SEQ ID NO: 9).

5. The nanosensor of claim 1, wherein the nanosensor emits a third emission of electromagnetic radiation, distinguishable from the first emission and the second emission, upon interacting with a second analyte.

6. The nanosensor of claim 1, wherein the photoluminescent nanostructure comprises a carbon nanotube.

7. The nanosensor of claim 6, wherein the photoluminescent nanostructure comprises a single-walled carbon nanotube.

8. The nanosensor of claim 7, wherein the photoluminescent nanostructure comprises a semiconducting single-walled carbon nanotube.

9. A nanosensor for determining a nitroaryl group, a pesticide, an explosive, a 2,4-dinitrophenol, a 4-nitro-3-(trifluoromethyl)phenol, a picric acid, a trinitrotoluene, or a cyclotrimethylenetrinitramine, comprising:
   a photoluminescent nanostructure; and
   a polymer comprising a polypeptide associated with the photoluminescent nanostructure, wherein
      the nanosensor emits a first emission of electromagnetic radiation in the absence of the nitroaryl group, the pesticide, the explosive, the 2,4-dinitrophenol, the 4-nitro-3-(trifluoromethyl)phenol, the picric acid, the trinitrotoluene, and the cyclotrimethylenetrinitramine;
      the nanosensor emits a second emission of electromagnetic radiation, distinguishable from the first emission, upon the polypeptide interacting with the nitroaryl group, the pesticide, the explosive, the 2,4-dinitrophenol, the 4-nitro-3-(trifluoromethyl)phenol, the picric acid, the trinitrotoluene, or the cyclotrimethylenetrinitramine; and
      the polymer comprises a polypeptide sequence, or derivative thereof, observed in the venom of a member of the Insecta class; a member of the Hymenoptera order; or a member of the Vespidae or Apidae families.

10. The nanosensor of claim 9, wherein the polymer comprises a polypeptide selected from the group consisting of: an amphiphilic helical polypeptide; a polypeptide including between about 5 and about 50 amino acid residues; and a polypeptide with a molecular weight of between about 400 g/mol and about 10,000 g/mol.

11. The nanosensor of claim 9, wherein the polymer comprises a polypeptide, or derivative thereof, from the Mastoparan or Bombolitin peptide families.

12. The nanosensor of claim 9, wherein the polymer comprises a polypeptide comprising at least one of KKAAAVLL-PVLLAAP (SEQ ID NO: 1), EEEECCCCHSSYW-YAFNNKT (SEQ ID NO: 2), INLKALAALAKKIL (SEQ ID NO: 3), INLKALAALAKALL (SEQ ID NO: 4), INWK-GIAAMAKKLL (SEQ ID NO: 5), IKIMDILAKLGKV-LAHV (SEQ ID NO: 6), INIKDILAKLVKVLGHV (SEQ ID NO: 7), IKITTMLAKLGKVLAHV (SEQ ID NO: 8), or SKITDILAKLGKVLAHV (SEQ ID NO: 9).

13. The nanosensor of claim 9, wherein the nanosensor emits a third emission of electromagnetic radiation, distinguishable from the first emission and the second emission, upon interacting with a second nitroaryl group, a second pesticide, a second explosive, a second 2,4-dinitrophenol, a second 4-nitro-3-(trifluoromethyl)phenol, a second picric acid, a second trinitrotoluene, or a second cyclotrimethylenetrinitramine.

14. The nanosensor of claim 9, wherein the photoluminescent nanostructure comprises a carbon nanotube.

15. The nanosensor of claim 14, wherein the photoluminescent nanostructure comprises a single-walled carbon nanotube.

16. The nanosensor of claim 15, wherein the photoluminescent nanostructure comprises a semiconducting single-walled carbon nanotube.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Ala Ala Ala Val Leu Leu Pro Val Leu Leu Ala Ala Pro
 1               5                  10                  15

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Glu Glu Cys Cys Cys Cys His Ser Ser Tyr Trp Tyr Ala Phe Asn Asn
 1               5                  10                  15

Lys Thr
     20

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide variant of the mastoparan peptide family

<400> SEQUENCE: 3

Ile Asn Leu Lys Ala Leu Ala Ala Leu Ala Lys Lys Ile Leu
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide variant of the mastoparan peptide family
```

```
<400> SEQUENCE: 4

Ile Asn Leu Lys Ala Leu Ala Ala Leu Ala Lys Ala Leu Leu
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide variant of the mastoparan peptide family

<400> SEQUENCE: 5

Ile Asn Trp Lys Glu Ile Ala Ala Met Ala Lys Lys Leu Leu
 1               5                  10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide variant of the Bombolitin peptide family

<400> SEQUENCE: 6

Ile Lys Ile Met Asp Ile Leu Ala Lys Leu Glu Lys Val Leu Ala His Val
 1               5                  10                  15

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide variant of the Bombolitin peptide family

<400> SEQUENCE: 7

Ile Asn Ile Lys Asp Ile Leu Ala Lys Leu Val Lys Val Leu Glu His Val
 1               5                  10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide variant of the Bombolitin peptide family

<400> SEQUENCE: 8

Ile Lys Ile Thr Thr Met Leu Ala Lys Leu Glu Lys Val Leu Ala His Val
 1               5                  10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide variant of the Bombolitin peptide family

<400> SEQUENCE: 9

Ser Lys Ile Thr Asp Ile Leu Ala Lys Leu Glu Lys Val Leu Ala His Val
 1               5                  10                  15

<210> SEQ ID NO 10
<211> LENGTH: 30
<212> TYPE: DNA
<213> ORGANISM: Artificial Sequence
```

<220> FEATURE:
<223> OTHER INFORMATION: Description of Artificial Sequence: Synthetic
      nucleic acid sequence

<400> SEQUENCE: 10
gtgtgtgtgt gtgtgtgtgt gtgtgtgtgt                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 11
atatatatat atatatatat atatatatat                                    30

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 12
ggggtggggt ggggtggggt ggggt                                         25

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 13
tttttgtttt                                                          10

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 14
tttttttttt tttttttttt tttttttttt                                    30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 15
ggttggttgg ttggttggtt ggttggtttt                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic

```
nucleic acid sequence

<400> SEQUENCE: 16
gatgatgatg atgatgatga tgatgatgat                                          30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 17
aaaataaaat aaaataaaat aaaat                                               25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 18
acctggggga gtattgcgga ggaagtt                                             27

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 19
aaaataaaat aaaataaaat aaaataaaat                                          30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleic acid sequence

<400> SEQUENCE: 20
ggggtggggt ggggtggggt ggggtggggt                                          30
```